(12) United States Patent
Decarlo et al.

(10) Patent No.: US 7,666,852 B2
(45) Date of Patent: *Feb. 23, 2010

(54) WOUND AND CUTANEOUS INJURY HEALING WITH A NUCLEIC ACID ENCODING A PROTEOGLYCAN POLYPEPTIDE

(75) Inventors: Arthur A. Decarlo, Vestavia Hills, AL (US); John Whitelock, Strath Field (AU); April L. Ellis, Pinson, AL (US)

(73) Assignee: Agenta Biotechnologies, Inc., Birmingham, AL (US)

( * ) Notice: Subject to any disclaimer, the term of this patent is extended or adjusted under 35 U.S.C. 154(b) by 234 days.

This patent is subject to a terminal disclaimer.

(21) Appl. No.: 11/803,404

(22) Filed: May 14, 2007

(65) Prior Publication Data
US 2008/0247995 A1    Oct. 9, 2008

Related U.S. Application Data

(63) Continuation-in-part of application No. 11/604,633, filed on Nov. 27, 2006, now Pat. No. 7,488,719, which is a continuation of application No. 10/420,270, filed on Apr. 22, 2003, now Pat. No. 7,141,551.

(60) Provisional application No. 60/374,553, filed on Apr. 22, 2002.

(51) Int. Cl.
*A01K 63/00* (2006.01)
*A61K 48/00* (2006.01)

(52) U.S. Cl. .................. 514/44; 424/93.2; 424/93.21
(58) Field of Classification Search ................ 514/44
See application file for complete search history.

(56) References Cited

U.S. PATENT DOCUMENTS 6,524,573 B1    2/2003  Iozzo 7,029,668 B2    4/2006  Simons
7,141,551 B1    11/2006 DeCarlo

FOREIGN PATENT DOCUMENTS

WO    9906054    2/1999
WO    0217955    3/2002

OTHER PUBLICATIONS

Crombleholme, 2008, Wound Repair and Regeneration, 8:460-472.*
International Search Report, PCT/US2008/006139, May 14, 2008.
Groffen et al., Expression and Characterization of Human Perlecan Domains I and II Synthesized by Baculovirus-Infected Insect Cells. Eur. J. Biochem. 241, pp. 827-834.
Nugent et al., Fibroblast Growth Factor-2. International J. Biochem. Cell Viol. 2000, vol. 32 pp. 115-120.
Zhao et al., Adenovirus-Mediated Decorin Gene Transfer Prevents TGF-Beta Induced Inhibition of Lung Morphogenesis. American Physiological Society. vol. 277 (Lung Cell. Mol. Phys.21) pp. L412-L422.

* cited by examiner

*Primary Examiner*—Valarie Bertoglio
(74) *Attorney, Agent, or Firm*—Bradley Arant Boult Cummings, LLP.; T. Gregory Peterson

(57) ABSTRACT

The present disclosure provides nucleic acid constructs encoding one or more polypeptides containing at least one glycosaminoglycan chain, such as, but not limited to, a proteoglycan polypeptide, and methods for delivering to the site of a wound or cutaneous injury at least one nucleic acid construct encoding one or more such polypeptides, such that the expressed polypeptide is glycated by glycosaminoglycan chains through the normal physiological processes of the subject at the site of administration to produce a functional proteoglycan polypeptide for the healing of the wound or other cutaneous injury. The delivered nucleic acid construct is transcribed, translated and post-translationally modified by the addition of glycosaminoglycan chains (referred herein as "decoration" or "glycation") to produce a decorated polypeptide. The decorated polypeptide is then secreted from the cell in which it was produced to provide treatment of wounds and/or cutaneous injury in the subject and/or prevention of cutaneous injury in a subject.

18 Claims, 6 Drawing Sheets

1                    2

| HEP-SS1 | 2Q546 | CS56 | Control |
|---------|-------|------|---------|
| A | B | C | D |

SEQUENCE LISTING

<160> NUMBER OF SEQ ID NOS: 27

<210> SEQ ID NO 1
<211> LENGTH: 7249
<212> TYPE: DNA
<213> ORGANISM: Homo sapiens

<400> SEQUENCE: 1

| | | | | | |
|---|---|---|---|---|---|
| atgaccactt | tactctgggt | tttcgtgact | ctgagggtca | tcactgcagc | tgtcactgta    60 |
| gaaacttcag | accatgacaa | ctcgctgagt | gtcagcatcc | cccaaccgtc | cccgctgagg   120 |
| gtcctcctgg | ggacctccct | caccatcccc | tgctatttca | tcgacccccat | gcaccctgtg   180 |
| accaccgccc | cttctaccgc | cccactggcc | ccaagaatca | agtggagccg | tgtgtccaag   240 |
| gagaaggagg | tagtgctgct | ggtggccact | gaagggcgcg | tgcgggtcaa | cagtgcctat   300 |
| caggacaagg | tctcactgcc | caactacccg | gccatcccca | gtgacgccac | cttggaagtc   360 |
| cagagcctgc | gctccaatga | ctctggggtc | taccgctgcg | aggtgatgca | tggcatcgag   420 |
| gacagcgagg | ccaccctgga | agtcgtggtg | aaaggcatcg | tgttccatta | cagagccatc   480 |
| tctacacgct | acacccctcga | ctttgacagg | gcgcagcggg | cctgcctgca | gaacagtgcc   540 |
| atcattgcca | cgcctgagca | gctgcaggcc | gcctacgaag | acggcttcca | ccagtgtgac   600 |
| gccggctggc | tggctgacca | gactgtcaga | tacccccatcc | acactccccg | ggaaggctgc   660 |
| tatggagaca | aggatgagtt | tcctggtgtg | aggacgtatg | gcatccgaga | caccaacgag   720 |
| acctatgatg | tgtactgctt | cgccgaggag | atggagggtg | aggtctttta | tgcaacatct   780 |
| ccagagaagt | tcaccttcca | ggaagcagcc | aatgagtgcc | ggcggctggg | tgcccggctg   840 |
| gccaccacgg | gccacgtcta | cctggcctgg | caggctggca | tggacatgtg | cagcgccggc   900 |
| tggctggccg | accgcagcgt | gcgctacccc | atctccaagg | cccggcccaa | ctgcggtggc   960 |
| aacctcctgg | gcgtgaggac | cgtctacgtg | catgccaacc | agacgggcta | ccccgacccc  1020 |
| tcatcccgct | acgacgccat | ctgctacaca | ggtgaagact | ttgtggacat | cccagaaaac  1080 |
| ttcttggag | tggggggtga | ggaggacatc | accgtccaga | cagtgacctg | gcctgacatg  1140 |
| gagctgccac | tgcctcgaaa | catcactgag | ggtgaagccc | gaggcagcgt | gatccttacc  1200 |
| gtaaagccca | tcttcgaggt | ctcccccagt | cccctggaac | ccgaggagcc | cttcacgttt  1260 |
| gcccctgaaa | tagggggccac | tgccttcgct | gaggttgaga | atgagactgg | agaggccacc  1320 |
| aggccctggg | gctttcccac | acctggcctg | ggccctgcca | cggcattcac | cagtgaggac  1380 |
| ctcgtcgtgc | aggtgaccgc | tgtccctggg | cagccgcatt | gccaggggg | ggtcgtcttc  1440 |
| cactaccgcc | cgggacccac | ccgctactcg | ctgaccttg | aggaggcaca | gcaggcctgc  1500 |
| cctggcacgg | gggcggtcat | tgcctcgccg | gagcagctcc | aggccgccta | cgaagcaggc  1560 |
| tatgagcagt | gtgacgccgg | ctggctgcgg | gaccagaccc | tcagatacccc | cattgtgagc  1620 |
| ccacggaccc | catgcgtggg | tgacaaggac | agcagcccag | gggtcaggac | ctatggcgtg  1680 |
| cgcccatcaa | cagagaccta | cgatgtctac | tgctttgtag | acagacttga | gggggaggtg  1740 |
| ttcttcgcca | cacgccttga | gcagttcacc | ttccaggaag | cactggagtt | ctgtgaatct  1800 |
| cacaatgcca | ctgccaccac | gggccagctc | tacgccgcct | ggagccgcgg | cctggacaag  1860 |

```
tgctatgccg gctggctggc cgacggcagc ctccgctacc ccatcgtcac cccaaggcct    1920
gcctgcggtg gggacaagcc aggcgtgaga acggtctacc tctaccctaa ccagacgggc    1980
ctcccagacc cactgtcccg gcaccatgcc ttctgcttcc gaggcatttc agcggttcct    2040
tctccaggag aagaagaggg tggcacaccc acatcaccct ctggtgtgga ggagtggatc    2100
gtgacccaag tggttcctgg tgtggctgct gtccccgtag aagaggagac aactgctgta    2160
ccctcagggg agactactgc catcctagag ttcaccaccg agccagaaaa ccagacagaa    2220
tgggaaccag cctataccc agtgggcaca tccccgctgc cagggatcct tcctacttgg      2280
cctcctactg gcgccgaaac agaggaaagt acagaaggcc cttctgcaac tgaagtgccc    2340
tctgcctcag aggaaccatc cccctcagag gtgccattcc cctcagagga gccatccccc    2400
tcagaggaac cattcccctc agtgaggcca ttcccctcag tggagctgtt cccctcagag    2460
gagccattcc cctccaagga gccatccccc tcagaggaac catcagcctc agaagagccg    2520
tatacacctt cacccccga gcccagctgg actgagctgc ccagctctgg ggaggaatct     2580
ggggcccctg atgtcagtgg tgacttcaca ggcagtggag atgtttcagg acaccttgac    2640
ttcagtgggc agctgtcagg ggacagggca agtggactgc cctctggaga cctggactcc    2700
agtggtctta cttccacagt gggctcaggc ctgactgtgg aaagtggact accctcaggg    2760
gatgaagaga gaattgagtg gcccagcact cctacggttg gtgaactgcc ctctggagct    2820
gagatcctag agggctctgc ctctggagtt ggggatctca gtggacttcc ttctggagaa    2880
gttctagaga ccctctgcct ctggagtagga gacctcagtg gcttccttc tggagaagtt    2940 ctagagacca ctgccctgg agtagaggac atcagcgggc ttccttctgg agaagttcta    3000
gagaccactg cccctggagt agaggacatc agcgggcttc cttctggaga agttctagag    3060
accactgccc ctggagtaga ggacatcagc gggcttcctt ctggagaagt tctagagacc    3120
actgcccctg gagtagagga catcagcggg cttccttctg gagaagttct agagaccact    3180
gcccctggag tagaggacat cagcgggctt ccttctggag aagttctaga gaccgctgcc    3240
cctggagtag aggacatcag cgggcttcct tctggagaag ttctagagac cgctgccct    3300 ggagtagagg acatcagcgg gcttccttct ggagaagttc tagagaccgc tgcccctgga    3360
gtagaggaca tcagcgggct tccttctgga gaagttctag agaccgctgc ccctggagta    3420
gaggacatca gcgggcttcc ttctggagaa gttctagaga ccgctgcccc tggagtagag    3480
gacatcagcg gcttccttc tggagaagtt ctagagaccg ctgcccctgg agtagaggac    3540
atcagcgggc ttccttctgg agaagttcta gagaccgctg cccctggagt agaggacatc    3600
agcgggcttc cttctggaga agttctagag actgctgccc ctggagtaga ggacatcagc    3660
gggcttcctt ctgagaagt tctagagact gctgcccctg gagtagagga catcagcggg    3720
cttccttctg gagaagttct agagactgct gcccctggag tagaggacat cagcgggctt    3780
ccttctggag aagttctaga gactgctgcc cctggagtag aggacatcag cgggcttcct    3840
tctggagaag ttctagagac tactgcccct ggagtagagg agatcagcgg gcttccttct    3900
ggagaagttc tagagactac tgcccctgga gtagatgaga tcagtgggct tccttctgga    3960
gaagttctag agactactgc ccctggagta gaggagatca gcgggcttcc ttctggagaa    4020
gttctagaga cttctacctc tgcggtaggg gacctcagtg gacttccttc tggaggagaa    4080
gttctagaga tttctgtctc tggagtagag gacatcagtg gcttccttc tggagaggtt     4140 gtagagactt ctgcctctgg aatagaggat gtcagtgaac ttccttcagg agaaggtcta    4200
```

```
gagacctctg cttctggagt agaggacctc agcaggctcc cttctggaga agaagttcta   4260
gagatttctg cctctggatt tggggacctc agtggagttc cttctggagg agaaggtcta   4320
gagacctctg cttctgaagt agggactgac ctcagtgggc ttccttctgg aagggagggt   4380
ctagagactt cagcttctgg agctgaggac ctcagtgggt tgccttctgg aaaagaagac   4440
ttggtggggt cagcttctgg agacttggac ttgggcaaac tgccttctgg aactctagga   4500
agtgggcaag ctccagaaac aagtggtctt ccctctggat ttagtggtga gtattctggg   4560
gtggaccttg gaagtggccc accctctggc ctgcctgact ttagtggact tccatctgga   4620
ttcccaactg tttccctagt ggattctaca ttggtggaag tggtcacagc ctccactgca   4680
agtgaactgg aagggagggg aaccattggc atcagtggtg caggagaaat atctggactg   4740
ccctccagtg agctggacat tagtgggaga gctagtggac tcccttcagg aactgaactc   4800
agtggccaag catctgggtc tcctgatgtc agtggggaaa tacctggact ctttggtgtc   4860
agtggacagc catcagggtt tcctgacact agtggggaaa catctggagt gactgagctt   4920
agcgggctgt cctctggaca accaggtgtt agtggagaag catctggagt tctttatggc   4980
actagtcaac cctttggcat aactgatctg agtggagaaa catctggggt ccctgatctc   5040
agtgggcagc cttcagggtt accagggttc agtggggcaa catcaggagt ccctgacctg   5100
gtttctggta ccacgagtgg cagcggtgaa tcttctggga ttacatttgt ggacaccagt   5160
ttggttgaag tggcccctac tacatttaaa gaagaagaag cttagggtc tgtggaactc    5220
agtggcctcc cttccggaga ggcagatctg tcaggcaaat ctgggatggt ggatgtcagt   5280
ggacagtttt ctggaacagt cgattccagt gggtttacat cccagactcc ggaattcagt   5340
ggcctaccaa gtggcatagc tgaggtcagt ggagaatcct ccagagctga gattgggagc   5400
agcctgccct cgggagcata ttatggcagt ggaactccat ctagtttccc cacggtctct   5460
cttgtagaca aactttggt ggaatctgta acccaggctc caacagccca agaggcagga   5520
gaagggcctt ctggcatttt agaactcagt ggtgctcatt ctggagcacc agacatgtct   5580
ggggagcatt ctggatttct ggacctaagt gggctgcagt ccgggctgat agagcccagc   5640
ggagagccac caggtactcc atattttagt ggggattttg ccagcaccac caatgtaagt   5700
ggagaatcct ctgtagccat gggcaccagt ggagaggcct caggacttcc agaagttact   5760
ttaatcactt ctgagttcgt ggagggtgtt actgaaccaa ctatttctca ggaactaggc   5820
caaaggcccc ctgtgacaca cacccccag cttttttgagt ccagtggaaa agtctccaca   5880
gctggggacg ttagtggagc taccccagtg ctccctgggt ctggagtaga agtatcatca   5940
gtcccagaat ctagcagtga gacgtccgcc tatcctgaag ctgggttcgg ggcatctgcc   6000
gcccctgagg ccagcagaga agattctggg tcccctgatc tgagtgaaac cacctctgca   6060
ttccacgaag ctaacctcga gagatcctct ggcctaggag tgagcggcag cactttgaca   6120
tttcaagaag gcgaggcgtc cgctgcccca gaagtgagtg agaatccac caccaccagt    6180
gatgtgggga cagaggcacc aggcttggct tcagccactc ccacggcttc tggagacagg   6240
actgaaatca gcgagacct gtctggtcac acctcgcagc tgggcgttgt catcagcacc    6300
agcatcccag agtctgagtg acccagcag acccagcgcc ctgcagagac gcatctagaa   6360
attgagtcct caagcctcct gtactcagga gaagagactc acacagtcga acagccacc   6420
tccccaacag atgcgtccat cccagcttct ccggaatgga aacgtgaatc agaatcaact   6480
gctgcagccc ccgccaggtc ctgtgcagag gagccctgtg gagctgggac ctgcaaggag   6540
acagagggac acgtcatatg cctgtgcccc cctggctaca ctggcgagca ctgtaacata   6600
```

| | |
|---|---:|
| gaccaggagg tatgtgagga gggctggaac aagtaccagg gccactgtta ccgccacttc | 6660 |
| ccggaccgcg agacctgggt ggatgctgag cgccggtgtc gggagcagca gtcacacctg | 6720 |
| agcagcatcg tcaccccga ggagcaggag tttgtcaaca caatgccca agactaccag | 6780 |
| tggatcggcc tgaacgacag gaccatcgaa ggggacttcc gctggtcaga tggacacccc | 6840 |
| atgcaatttg agaactggcg ccccaaccag cctgacaact tttttgccgc tggagaggac | 6900 |
| tgtgtggtga tgatctggca cgagaagggc gagtggaatg atgttccctg caattaccac | 6960 |
| ctccccttca cgtgtaaaaa gggcacagtg gcctgcggag agcccctgt ggtggagcat | 7020 |
| gccaggacct tcgggcagaa gaaggaccgg tatgagatca attccctggt gcggtaccag | 7080 |
| tgcacagagg ggtttgtcca cgccacatg cccaccatcc ggtgccagcc cagcgggcac | 7140 |
| tgggaggagc ctcggatcac ctgcacagac cccaccacct acaaacgcag actacagaag | 7200 |
| cggagctcac ggcaccctcg gaggagccgc cccagcacag cccactgag | 7249 |

<210> SEQ ID NO 2
<211> LENGTH: 10191
<212> TYPE: DNA
<213> ORGANISM: Homo sapiens

<400> SEQUENCE: 2

| | |
|---|---:|
| atgttcataa atataaagag catcttatgg atgtgttcaa ccttaatagt aacccatgcg | 60 |
| ctacataaag tcaaagtggg aaaaagccca ccggtgaggg gctccctctc tggaaaagtc | 120 |
| agcctacctt gtcattttc aacgatgcct actttgccac ccagttacaa caccagtgaa | 180 |
| tttctccgca tcaaatggtc taagattgaa gtggacaaaa atggaaaaga tttgaaagag | 240 |
| actactgtcc ttgtggccca aaatggaaat atcaagattg tcaggacta caagggagaa | 300 |
| gtgtctgtgc ccacacatcc cgaggctgtg ggcgatgcct ccctcactgt ggtcaagctg | 360 |
| ctggcaagtg atgcgggtct ttaccgctgt gacgtcatgt acgggattga agacacacaa | 420 |
| gacacggtgt cactgactgt ggatgggtt tgtttcact acagggcggc aaccagcagg | 480 |
| tacacactga atttgaggc tgctcagaag gcttgtttgg acgttggggc agtcatagca | 540 |
| actccagagc agctctttgc tgcctatgaa gatggatttg agcagtgtga cgcaggctgg | 600 |
| ctggctgatc agactgtcag atatccatc cgggctccca gagtaggctg ttatggagat | 660 |
| aagatgggaa aggcaggagt caggacttat ggattccgtt ctccccagga aacttacgat | 720 |
| gtgtattgtt atgtggatca tctggatggt gatgtgttcc acctcactgt ccccagtaaa | 780 |
| ttcaccttcg aggaggctgc aaaagagtgt gaaaaccagg atgccaggct ggcaacagtg | 840 |
| ggggaactcc aggcggcatg gaggaacggc tttgaccagt gcgattacgg gtggctgtcg | 900 |
| gatgccagcg tgcgccaccc tgtgactgtg gccagggccc agtgtggagg tggtctactt | 960 |
| ggggtgagaa ccctgtatcg ttttgagaac cagacaggct ccctcccccc tgatagcaga | 1020 |
| tttgatgcct actgctttaa acctaaagag gctacaacca tcgatttgag tatcctcgca | 1080 |
| gaaactgcat cacccagttt atccaaagaa ccacaaatgg tttctgatag aactacacca | 1140 |
| atcatccctt tagttgatga attacctgtc attccaacag agttccctcc cgtgggaaat | 1200 |
| attgtcagtt tgaacagaa agccacagtc aacctcagg ctatcacaga tagtttagcc | 1260 |
| accaaattac ccacacctac tggcagtacc aagaagccct gggatatgga tgactactca | 1320 |
| ccttctgctt caggacctct tggaaagcta gacatatcag aaattaagga agaagtgctc | 1380 |
| cagagtacaa ctggcgtctc tcattatgct acggattcat gggatggtgt cgtggaagat | 1440 |

```
aaacaaacac aagaatcggt tacacagatt gaacaaatag aagtgggtcc tttggtaaca    1500
tctatggaaa tcttaaagca cattccttcc aaggaattcc ctgtaactga acaccattg    1560 gtaactgcaa gaatgatcct ggaatccaaa actgaaaaga aaatggtaag cactgtttct    1620
gaattggtaa ccacaggtca ctatggattc accttgggag aagaggatga tgaagacaga    1680
acacttacag ttggatctga tgagagcacc ttgatctttg accaaattcc tgaagtcatt    1740
acggtgtcaa agacttcaga agacaccatc cacactcatt tagaagactt ggagtcagtc    1800
tcagcatcca caactgtttc ccctttaatt atgcctgata taatggatc atccatggat     1860 gactgggaag agagacaaac tagtggtagg ataacggaag agtttcttgg caaatatctg    1920
tctactacac cttttccatc acagcatcgt acagaaatag aattgtttcc ttattctggt    1980
gataaaatat tagtagaggg aatttccaca gttatttatc cttctctaca aacagaaatg    2040
acacatagaa gagaaagaac agaaacacta ataccagaga tgagaacaga tacttataca    2100
gatgaaatac aagaagagat cactaaaagt ccatttatgg gaaaaacaga gaagaagtc    2160 ttctctggga tgaaactctc tacatctctc tcagagccaa ttcatgttac agagtcttct    2220
gtggaaatga ccaagtcttt tgatttccca acattgataa caaagttaag tgcagagcca    2280
acagaagtaa gagatatgga ggaagacttt acagcaactc caggtactac aaaatatgat    2340
gaaaatatta caacagtgct tttggcccat ggtactttaa gtgttgaagc agccactgta    2400
tcaaaatggt catgggatga agataataca acatccaagc ctttagagtc tacagaacct    2460
tcagcctctt caaaattgcc ccctgcctta ctcacaactg tggggatgaa tggaaaggat    2520
aaagacatcc caagtttcac tgaagatgga gcagatgaat ttactcttat tccagatagt    2580
actcaaaagc agttgagga ggttactgat gaagacatag cagcccatgg aaaattcaca    2640
attagatttc agccaactac atcaactggt attgcagaaa agtcaacttt gagagattct    2700
acaactgaag aaaaagttcc acctatcaca agcactgaag gccaagttta tgcaaccatg    2760
gaaggaagtg ctttgggtga agtagaagat gtggacctct ctaagccagt atctactgtt    2820
ccccaatttg cacacacttc agaggtggaa ggattagcat tgttagtta tagtagcacc    2880 caagagccta ctacttatgt agactcttcc cataccattc ctctttctgt aattcccaag    2940
acagactggg gagtgttagt accttctgtt ccatcagaag atgaagttct aggtgaaccc    3000
tctcaagaca tacttgtcat tgatcagact cgccttgaag cgactatttc tccagaaact    3060
atgagaacaa caaaaatcac agagggaaca actcaggaag aattcccttg gaaagaacag    3120
actgcagaga aaccagttcc tgctctcagt tctacagctt ggactcccaa ggaggcagta    3180
acaccactgg atgaacaaga gggcgatgga tcagcatata cagtctctga agatgaattg    3240
ttgacaggtt ctgagagggt cccagtttta gaaacaactc cagttggaaa aattgatcac    3300
agtgtgtctt atccaccagg tgctgtaact gagcacaaag tgaaaacaga tgaagtggta    3360
acactaacac cacgcattgg gccaaaagta tctttaagtc cagggcctga acaaaaatat    3420
gaaacagaag gtagtagtac aacaggattt acatcatctt tgagtccttt tagtacccac    3480
attacccagc ttatggaaga aaccactact gagaaaacat ccctagagga tattgattta    3540
ggctcaggat tatttgaaaa gcccaaagcc acagaactca tagaattttc aacaatcaaa    3600
gtcacagttc caagtgatat taccactgcc ttcagttcag tagacagact tcacacaact    3660
tcagcattca agccatcttc cgcgatcact aagaaaccac ctctcatcga cagggaacct    3720
ggtgaagaaa caaccagtga catggtaatc attggagaat caacatctca tgttcctccc    3780
actacccttg aagatattgt agccaaggaa acagaaaccg atattgatag agagtatttc    3840
```

```
acgacttcaa gtcctcctgc tacacagcca acaagaccac ccactgtgga agacaaagag    3900
gcctttggac ctcaggcgct ttctacgcca cagcccccag caagcacaaa atttcaccct    3960
gacattaatg tttatattat tgaggtcaga gaaaataaga caggtcgaat gagtgatttg    4020
agtgtaattg gtcatccaat agattcagaa tctaaagaag atgaaccttg tagtgaagaa    4080
acagatccag tgcatgatct aatggctgaa attttacctg aattccctga cataattgaa    4140
atagacctat accacagtga agaaaatgaa gaagaagaag aagagtgtgc aaatgctact    4200
gatgtgacaa ccaccccatc tgtgcagtac ataaatggga agcatctcgt taccactgtg    4260
cccaaggacc agaagctgc agaagctagg cgtggccagt ttgaaagtgt tgcaccttct    4320
cagaatttct cggacagctc tgaaagtgat actcatccat ttgtaatagc caaaacggaa    4380
ttgtctactg ctgtgcaacc taatgaatct acagaaacaa ctgagtctct tgaagttaca    4440
tggaagcctg agacttaccc tgaaacatca gaacattttt caggtggtga gcctgatgtt    4500
ttccccacag tcccattcca tgaggaattt gaaagtggaa cagccaaaaa aggggcagaa    4560
tcagtcacag agagagatac tgaagttggt catcaggcac atgaacatac tgaacctgta    4620
tctctgtttc ctgaagagtc ttcaggagag attgccattg accaagaatc tcagaaaata    4680
gcctttgcaa gggctacaga agtaacattt ggtgaagagg tagaaaaaag tacttctgtc    4740
acatacactc ccactatagt tccaagttct gcatcagcat atgtttcaga ggaagaagca    4800
gttaccctaa taggaaatcc ttggccagat gacctgttgt ctaccaaaga aagctgggta    4860
gaagcaactc ctagacaagt tgtagagctc tcagggagtc cttcgattcc aattacagaa    4920
ggctctggag aagcagaaga agatgaagat acaatgttca ccatggtaac tgatttatca    4980
cagagaaata ctactgatac actcattact ttagacacta gcaggataat cacagaaagc    5040 tttttttgagg ttcctgcaac caccatttat ccagtttctg aacaaccttc tgcaaaagtg    5100
gtgcctacca agtttgtaag tgaaacagac acttctgagt ggatttccag taccactgtt    5160
gaggaaaaga aaggaagga ggaggaggga actacaggta cggcttctac atttgaggta    5220
tattcatcta cacagagatc ggatcaatta atttacccct ttgaattaga aagtccaaat    5280
gtagctacat ctagtgattc aggtaccagg aaaagtttta tgtccttgac aacaccaaca    5340
cagtctgaaa gggaaatgac agattctact cctgtctta cagaaacaaa tacattagaa    5400
aatttggggg cacagaccac tgagcacagc agtatccatc aacctggggt tcaggaaggg    5460
ctgaccactc tcccacgtag tcctgcctct gtctttatgg agcagggctc tggagaagct    5520
gctgccgacc cagaaccac cactgtttct tcattttcat taaacgtaga gtatgcaatt    5580
caagccgaaa aggaagtagc tggcactttg tctccgcatg tggaaactac attctccact    5640
gagccaacag gactggtttt gagtacagta atggacagag tagttgctga aaatataacc    5700
caaacatcca gggaaatagt gatttcagag cgattaggag aaccaaatta ggggcagaa    5760 ataagggct tttccacagg ttttcctttg gaggaagatt tcagtggtga ctttagagaa    5820
tactcaacag tgtctcatcc catagcaaaa gaagaaacgg taatgatgga aggctctgga    5880
gatgcagcat ttagggacac ccagacttca ccatctacag tacctacttc agttcacatc    5940
agtcacatat ctgactcaga aggacccagt agcaccatgg tcagcacttc agccttcccc    6000
tgggaagagt ttacatcctc agctgagggc tcaggtgagc aactggtcac agtcagcagc    6060
tctgttgttc cagtgcttcc cagtgctgtg caaaagtttt ctggtacagc ttcctccatt    6120
atcgacgaag gattgggaga agtgggtact gtcaatgaaa ttgatagaag atccaccatt    6180
```

```
ttaccaacag cagaagtgga aggtacgaaa gctccagtag agaaggagga agtaaaggtc   6240
agtggcacag tttcaacaaa ctttcccaa  actatagagc cagccaaatt atggtctagg   6300
caagaagtca accctgtaag acaagaaatt gaaagtgaaa caacatcaga ggaacaaatt   6360
caagaagaaa agtcatttga atcccctcaa aactctcctg caacagaaca aacaatcttt   6420
gattcacaga catttactga aactgaactc aaaaccacag attattctgt actaacaaca   6480
aagaaaactt acagtgatga taaagaaatg aaggaggaag cacttctttt agttaacatg   6540
tctactccag atccagatgc aaatggcttg gaatcttaca caactctccc tgaagctact   6600
gaaaagtcac attttttctt agctactgca ttagtaactg aatctatacc agctgaacat   6660
gtagtcacag attcaccaat caaaaaggaa gaaagtacaa acatttttcc gaaaggcatg   6720
agaccaacaa ttcaagagtc agatactgag ctcttattct ctggactggg atcaggagaa   6780
gaagttttac ctactctacc aacagagtca gtgaatttta ctgaagtgga acaaatcaat   6840
aacacattat atccccacac ttctcaagtg gaaagtacct caagtgacaa aattgaagac   6900
tttaacagaa tggaaaatgt ggcaaaagaa gttggaccac tcgtatctca aacagacatc   6960
tttgaaggta gtgggtcagt aaccagcaca acattaatag aaattttaag tgacactgga   7020
gcagaaggac ccacggtggc acctctccct ttctccacgg acatcggaca tcctcaaaat   7080
cagactgtca ggtgggcaga agaaatccag actagtagac cacaaaccat aactgaacaa   7140
gactctaaca agaattcttc aacagcagaa attaacgaaa caacaacctc atctactgat   7200
tttctggcta gagcttatgg ttttgaaatg gccaaagaat tgttacatc  agcaccaaaa   7260 ccatctgact tgtattatga accttctgga gaaggatctg gagaagtgga tattgttgat   7320
tcatttcaca cttctgcaac tactcaggca accagacaag aaagcagcac acatttgtt   7380 tctgatgggt ccctggaaaa acatcctgag gtgccaagcg ctaaagctgt tactgctgat   7440
ggattcccaa cagtttcagt gatgctgcct cttcattcag agcagaacaa aagctcccct   7500
gatccaacta gcacactgtc aaatacagtg tcatatgaga ggtccacaga cggtagtttc   7560
caagaccgtt tcagggaatt cgaggattcc accttaaaac ctaacagaaa aaaacccact   7620
gaaaatatta tcatagacct ggacaaagag gacaaggatt taatattgac aattacagag   7680
agtaccatcc ttgaaattct acctgagctg acatcggata aaaatactat catagatatt   7740
gatcatacta aacctgtgta tgaagacatt cttggaatgc aaacagatat agatacagag   7800
gtaccatcag aaccacatga cagtaatgat gaaagtaatg atgacagcac tcaagttcaa   7860
gagatctatg aggcagctgt caacctttct ttaactgagg aaacatttga gggctctgct   7920
gatgttctgg ctagctacac tcaggcaaca catgatgaat caatgactta tgaagataga   7980
agccaactag atcacatggg ctttcacttc acaactggga tccctgctcc tagcacagaa   8040
acagaattag acgttttact tcccacggca acatccctgc caattcctcg taagtctgcc   8100
acagttattc cagagattga aggaataaaa gctgaagcaa aagccctgga tgacatgttt   8160
gaatcaagca ctttgtctga tggtcaagct attgcagacc aaagtgaaat aataccaaca   8220
ttgggccaat ttgaaaggac tcaggaggag tatgaagaca aaaacatgc  tggtccttct   8280 tttcagccag aattctcttc aggagctgag gaggcattag tagaccatac tccctatcta   8340
agtattgcta ctacccacct tatggatcag agtgtaacag aggtgcctga tgtgatggaa   8400
ggatccaatc cccatatatt cactgataca acattagcag tttcaacatt tgcgaagttg   8460
tcttctcaga caccatcatc tccctcact  atctactcag gcagtgaagc ctctggacac   8520
acagagatcc cccagcccag tgctctgcca ggaatagacg tcggctcatc tgtaatgtcc   8580
```

```
ccacaggatt cttttaagga aattcatgta aatattgaag caactttcaa accatcaagt    8640
gaggaatacc ttcacataac tgagcctccc tctttatctc ctgacacaaa attagaacct    8700
tcagaagatg atggtaaacc tgagttatta gaagaaatgg aagcttctcc cacagaactt    8760
attgctgtgg aaggaactga gattctccaa gatttccaaa acaaaaccga tggtcaagtt    8820
tctggagaag caatcaagat gtttcccacc attaaaacac ctgaggctgg aactgttatt    8880
acaactgccg atgaaattga attagaaggt gctacacagt ggccacactc tacttctgct    8940
tctgccacct atggggtcga ggcaggtgtg gtgccttggc taagtccaca gacttctgag    9000
aggcccacgc tttcttcttc tccagaaata aaccctgaaa ctcaagcagc tttaatcaga    9060
gggcaggatt ccacgatagc agcatcagaa cagcaagtgg cagcgagaat tcttgattcc    9120
aatgatcagg caacagtaaa ccctgtggaa tttaatactg aggttgcaac accaccattt    9180
tcccttctgg agacttctaa tgaaacagat ttcctgattg cattaatgaa agagtcagtg    9240
gaaggcacgg caatctattt accaggacct gatcgctgca aaatgaaccc gtgccttaac    9300
ggaggcacct gttatcctac tgaaacttcc tacgtatgca cctgtgtgcc aggatacagc    9360
ggagaccagt gtgaacttga ttttgatgaa tgtcactcta atccctgtcg taatggagcc    9420
acttgtgttg atggttttaa cacattcagg tgcctctgcc ttccaagtta tgttggtgca    9480 cttttgtgagc aagataccga gacatgtgac tatggctgga caaaattcca agggcagtgc    9540
tacaaatact ttgcccatcg acgcacatgg gatgcagctg aacgggaatg ccgtctgcag    9600
ggtgcccatc tcacaagcat cctgtctcac gaagaacaaa tgtttgttaa tcgtgtgggc    9660
catgattatc agtggatagg cctcaatgac aagatgtttg agcatgactt ccgttggact    9720
gatggcagca cactgcaata cgagaattgg agacccaacc agccagacag cttcttttct    9780
gctggagaag actgtgttgt aatcatttgg catgagaatg ccagtggaaa tgatgttccc    9840
tgcaattacc atctcacccta tacgtgcaag aaaggaacga ttgcttgcgg ccagcccccct    9900 gttgtagaaa atgccaagac ctttggaaag atgaaacctc gttatgaaat caactccctg    9960
attagatacc actgcaaaga tggtttcatt caacgtcacc ttccaactat ccggtgctta   10020
ggaaatggaa gatgggctat acctaaaatt acctgcatga acccatctgc ataccaaagg   10080
acttattcta tgaaatactt taaaaattcc tcatcagcaa aggacaattc aataaataca   10140
tccaaacatg atcatcgttg gagccggagg tggcaggagt cgaggcgctg a           10191
```

<210> SEQ ID NO 3
<211> LENGTH: 1017
<212> TYPE: DNA
<213> ORGANISM: Homo sapiens

<400> SEQUENCE: 3

```
atgagtctaa gtgcatttac tctcttcctg gcattgattg gtggtaccag tggccagtac      60
tatgattatg attttcccct atcaatttat gggcaatcat caccaaactg tgcaccagaa     120
tgtaactgcc ctgaaagcta cccagtgccc atgtactgtg atgagctgaa attgaaaagt     180
gtaccaatgg tgcctcctgg aatcaagtat ctttaccttag gaataaccca gattgaccat     240
attgatgaaa aggcctttga gaatgtaact gatctgcagt ggctcattct agatcacaac     300
cttctagaaa actccaagat aaaagggaga gttttctcta aattgaaaca actgaagaag     360
ctgcatataa accacaacaa cctgacagag tctgtgggcc cacttcccaa atctctggag     420
gatctgcagc ttactcataa caagatcaca aagctgggct cttttgaagg attggtaaac     480
```

| | |
|---|---|
| ctgaccttca tccatctcca gcacaatcgg ctgaaagagg atgctgtttc agctgctttt | 540 |
| aaaggtctta aatcactcga ataccttgac ttgagcttca atcagatagc cagactgcct | 600 |
| tctggtctcc ctgtctctct tctaactctc tacttagaca acaataagat cagcaacatc | 660 |
| cctgatgagt atttcaagcg ttttaatgca ttgcagtatc tgcgtttatc tcacaacgaa | 720 |
| ctggctgata gtggaatacc tggaaattct ttcaatgtgt catccctggt tgagctggat | 780 |
| ctgtcctata acaagcttaa aaacatacca actgtcaatg aaaaccttga aaactattac | 840 |
| ctggaggtca atcaacttga aagtttgac ataaagagct tctgcaagat cctggggcca | 900 |
| ttatcctact ccaagatcaa gcatttgcgt ttggatggca atcgcatctc agaaaccagt | 960 |
| cttccaccgg atatgtatga atgtctacgt gttgctaacg aagtcactct taattaa | 1017 |

<210> SEQ ID NO 4
<211> LENGTH: 933
<212> TYPE: DNA
<213> ORGANISM: Homo sapiens

<400> SEQUENCE: 4

| | |
|---|---|
| atgaggcgcg cggcgctctg gctctggctg tgcgcgctgg cgctgagcct gcagccggcc | 60 |
| ctgccgcaaa ttgtggctac taatttgccc cctgaagatc aagatggctc tggggatgac | 120 |
| tctgacaact ctccggctc aggtgcaggt gctttgcaag atatcacctt gtcacagcag | 180 |
| acccctcca cttggaagga cacgcagctc ctgacggcta ttcccacgtc tccagaaccc | 240 |
| accggcctgg aggctacagc tgcctccacc tccaccctgc cggctggaga ggggcccaag | 300 |
| gagggagagg ctgtagtcct gccagaagtg gagcctggcc tcaccgcccg ggagcaggag | 360 |
| gccaccccc gacccaggga gaccacacag ctcccgacca ctcatcaggc ctcaacgacc | 420 |
| acagccacca cggcccagga gcccgccacc tcccacccc acagggacat gcagcctggc | 480 |
| caccatgaga cctcaacccc tgcaggacc agccaagctg accttcacac tccccacaca | 540 |
| gaggatggag gtccttctgc caccgagagg gctgctgagg atggagcctc cagtcagctc | 600 |
| ccagcagcag agggctctgg ggagcaggac ttcacctttg aaacctcggg ggagaatacg | 660 |
| gctgtagtgg ccgtggagcc tgaccgccgg aaccagtccc cagtggatca gggggccacg | 720 |
| ggggcctcac agggcctcct ggacaggaaa gaggtgctgg gagggggtcat gccggaggc | 780 |
| ctcgtggggc tcatctttgc tgtgtgcctg gtgggtttca tgctgtaccg catgaagaag | 840 |
| aaggacgaag gcagctactc cttggaggag ccgaaacaag ccaacggcgg ggcctaccag | 900 |
| aagcccacca acaggagga attctatgcc tga | 933 |

<210> SEQ ID NO 5
<211> LENGTH: 606
<212> TYPE: DNA
<213> ORGANISM: Homo sapiens

<400> SEQUENCE: 5

| | |
|---|---|
| atgcggcgcg cgtggatcct gctcaccttg gcttggtgg cctgcgtgtc ggcggagtcg | 60 |
| agagcagagc tgcatctcga taaagacatg taccttgaca acagctccat gaagaagct | 120 |
| tcaggagtgt atcctattga tgacgatgac tacgcttctg cgtctggctc gggagctgat | 180 |
| gaggatgtag agagtccaga gctgacaaca tctcgaccac ttccaaagat actgttgact | 240 |
| agtgctgctc caaaagtgga aaccacgacg ctgaatatac agaacaagat acctgctcag | 300 |
| acaaagtcac ctgaagaaac tgataaagag aaagttcacc tctctgactc agaaaggaaa | 360 |
| atggacccag ccgaagagga tacaaatgtg tatactgaga acactcgaga cagtctgttt | 420 |

-continued

```
aaacggacag aagtcctagc agctgtcatt gctggtggag ttattggctt tctctttgca      480 attttctta tcctgctgtt ggtgtatcgc atgagaaaga aggatgaagg aagctatgac      540
cttggagaac gcaaaccatc cagtgctgct tatcagaagg cacctactaa ggagttttat     600
gcgtaa                                                                606
```

<210> SEQ ID NO 6
<211> LENGTH: 1329
<212> TYPE: DNA
<213> ORGANISM: Homo sapiens

<400> SEQUENCE: 6

```
atgaagccgg ggccgccgca ccgtgccggg gccgcccacg gggccggcgc cggggccggg      60
gccgcggccg ggcccggggc ccgcgggctg ctcctgccac cgctgctgct gctgctgctg     120
gcggggcgcg ccgcggggc ccagcgctgg cgcagtgaga acttcgagag acccgtggac      180
ctggagggct ctggggatga tgactccttt cccgatgatg aactggatga cctctactcg     240
gggtcgggct cgggctactt cgagcaggag tcgggcattg agacagccat gcgcttcagc     300
ccagatgtag ccctggcggt gtccaccaca cctgcggtgc tgcccaccac gaacatccag     360
cctgtgggca caccatttga agagctcccc tctgagcgcc ccaccctgga gccagccacc     420 agcccctgg tggtgacaga agtcccggaa gagcccagcc agagagccac caccgtctcc     480
actaccatgg ctaccactgc tgccacaagc acaggggacc cgactgtggc cacagtgcct     540
gccacagtgg ccaccgccac ccccagcacc cctgcagcac cccttttac ggccaccact     600 gctgttataa ggaccactgg cgtacggagg cttctgcctc tcccactgac cacagtggct     660
acggcacggg ccactacccc cgaggcgccc tccccgccca ccacgcggc tgtcttggac     720 accgaggccc caacacccag gctggtcagc acagctacct cccggccaag agcccttccc     780
aggccggcca ccacccagga gcctgacatc cctgagagga gcaccctgcc cctggggacc     840
actgcccctg gacccacaga ggtggctcag accccaactc cagagacctt cctgaccaca     900
atccggaatg agccagaggt tccggtgagt ggggggcccca gtggagactt cgagctgcca     960
gaagaagaga ccacacaacc agacacagcc aatgaggtgg tagctgtggg aggggctgcg    1020
gccaaggcat catctccacc tgggacactg cccaagggtg cccgcccggg ccctggcctc    1080
ctggacaatg ccatcgactc gggcagctca gctgctcagc tgcctcagaa gagtatcctg    1140
gagcggaagg aggtgctcgt agctgtgatt gtgggcgggg tggtgggcgc cctcttgct    1200 gccttcttgg tcacactgct catctatcgt atgaagaaaa aggatgaggg cagctacacg    1260
ctggaggaac ccaagcaggc gagcgtcaca taccagaagc tgacaagca ggaggagttc    1320 tatgcctag                                                            1329
```

<210> SEQ ID NO 7
<211> LENGTH: 597
<212> TYPE: DNA
<213> ORGANISM: Homo sapiens

<400> SEQUENCE: 7

```
atggccccg cccgtctgtt cgcgctgctg ctgttcttcg taggcggagt cgccgagtcg       60
atccgagaga ctgaggtcat cgaccccag gacctcctag aaggccgata cttctccgga     120
gccctaccag acgatgagga tgtagtgggg cccgggcagg aatctgatga ctttgagctg     180
tctggctctg gagatctgga tgacttggaa gactccatga tcggccctga agttgtccat     240
```

-continued

```
cccttggtgc ctctagataa ccatatccct gagagggcag ggtctgggag ccaagtcccc        300
accgaaccca agaaactaga ggagaatgag gttatcccca agagaatctc acccgttgaa        360
gagagtgagg atgtgtccaa caaggtgtca atgtccagca ctgtgcaggg cagcaacatc        420
tttgagagaa cggaggtcct ggcagctctg attgtgggtg gcatcgtggg catcctcttt        480
gccgtcttcc tgatcctact gctcatgtac cgtatgaaga agaaggatga aggcagctat        540
gacctgggca agaaacccat ctacaagaaa gcccccacca atgagttcta cgcgtga         597
```

<210> SEQ ID NO 8
<211> LENGTH: 1677
<212> TYPE: DNA
<213> ORGANISM: Homo sapiens

<400> SEQUENCE: 8

```
atggagctcc gggcccgagg ctggtggctg ctatgtgcgg ccgcagcgct ggtcgcctgc         60
gcccgcgggg acccgccag caagagccgg agctgcggcg aggtccgcca gatctacgga        120
gccaagggct tcagcctgag cgacgtgccc caggcggaga tctcgggtga gcacctgcgg        180
atctgtcccc agggctacac ctgctgcacc agcgagatgg aggagaacct ggccaaccgc        240
agccatgccg agctggagac cgcgctccgg gacagcagcc gcgtcctgca ggccatgctt        300
gccacccagc tgcgcagctt cgatgaccac ttccagcacc tgctgaacga ctcggagcgg        360
acgctgcagg ccaccttccc cggcgccttc ggagagctgt acacgcagaa cgcgagggcc        420
ttccgggacc tgtactcaga gctgcgcctg tactaccgcg tgccaacct gcacctggag        480 gagacgctgg ccgagttctg ggcccgcctg ctcgagcgcc tcttcaagca gctgcacccc        540
cagctgctgc tgcctgatga ctacctggac tgcctgggca gcaggccga ggcgctgcgg        600 cccttcgggg aggccccgag agagctgcgc ctgcgggcca cccgtgcctt cgtggctgct        660
cgctcctttg tgcagggcct gggcgtggcc agcgacgtgg tccggaaagt ggctcaggtc        720
cccctgggcc cggagtgctc gagagctgtc atgaagctgg tctactgtgc tcactgcctg        780
ggagtccccg cgccaggcc ctgccctgac tattgccgaa atgtgctcaa gggctgcctt        840
gccaaccagg ccgacctgga cgccgagtgg aggaacctcc tggactccat ggtgctcatc        900
accgacaagt ctggggtac atcgggtgtg gagagtgtca tcggcagcgt gcacgtgg        960 ctggcggagg ccatcaacgc cctccaggac aacagggaca cgctcacggc caaggtcatc       1020
cagggctgcg ggaaccccaa ggtcaacccc cagggccctg ggcctgagga aagcggcgc       1080 cggggcaagc tggccccgcg ggagaggcca ccttcaggca cgctggagaa gctggtctct       1140
gaagccaagg cccagctccg cgacgtccag gacttctgga tcagcctccc agggacactg       1200
tgcagtgaga agatggccct gagcactgcc agtgatgacc gctgctggaa cgggatggcc       1260
agaggccggt acctccccga ggtcatgggt gacggcctgg ccaaccagat caacaaccc       1320 gaggtggagg tggacatcac caagccggac atgaccatcc ggcagcagat catgcagctg       1380
aagatcatga ccaaccggct gcgcagcgcc tacaacggca cgacgtgga cttccaggac       1440 gccagtgacg acgcagcgg ctcgggcagc ggtgatggct gtctggatga cctctgcggc       1500
cggaaggtca gcaggaagag ctccagctcc cggacgccct tgacccatgc cctcccaggc       1560
ctgtcagagc aggaaggaca gaagacctcg gctgccagct gccccagcc ccgaccttc       1620 ctcctgcccc tcctcctctt cctggccctt acagtagcca ggccccggtg gcggtaa       1677
```

<210> SEQ ID NO 9
<211> LENGTH: 2124

<212> TYPE: DNA
<213> ORGANISM: Homo sapiens

<400> SEQUENCE: 9

```
atgccgcctg gtccagctat cgtgctcggt attcagtttt ccggagcagc gctctttctc      60
tggcccgcgg agcggtcccg cggccgagta ccggattccc gagtttggga ggctctgctt     120
tcctccttag gacccacttt gccgtcctgg ggtggctgca gttatgtccg cgctgcgacc     180
tctcctgctt ctgctgctgc ctctgtgtcc cggtcctggt cccggacccg ggagcgaggc     240
aaaggtcacc cggagttgtg cagagacccg gcaggtgctg ggggcccggg gatatagctt     300
aaacctaatc cctcccgccc tgatctcagg tgagcacctc cgggtctgtc cccaggagta     360
cacctgctgt tccagtgaga cagagcagag gctgatcagg gagactgagg ccaccttccg     420
aggcctggtg gaggacagcg gctcctttct ggttcacaca ctggctgcca ggcacagaaa     480
atttgatgag ttttttctgg agatgctctc agtagcccag cactctctga cccagctctt     540
ctcccactcc tacggccgcc tgtatgccca gcacgccctc atattcaatg cctgttctc      600
tcggctgcga gacttctatg gggaatctgg tgaggggttg gatgacaccc tggcggattt     660
ctgggcacag ctcctggaga gagtgttccc gctgctgcac ccacagtaca gctttccccc     720
tgactacctg ctctgcctct cacgcttggc ctcatctacc gatggctctc tgcagccctt     780
tggggactca ccccgccgcc tccgcctgca gataacccgg accctggtgg ctgcccgagc     840
ctttgtgcag ggcctggaga ctggaagaaa tgtggtcagc gaagcgctta aggttggagg     900
gggcctgagt atgggcaggg cccagggagg gagaggtgga agtgagagag accccacaag     960
gaagaaacag ccaccagcca gcaggacagg ccttgggctc tgtctgcctc caggccctgg    1020
tgtcctagga tgaattagga aggaggggc tggagtgaaa cctccaatgg tccacgatcc    1080
atgatctctg acccctcct ccctctgtg gacccatacc ctcctcagtc cccaagggcc    1140
tgctcatctc catagcaagt aggagattgg atactgcccc cgcccaaccc cccaggatcc    1200
ctcaatgact ccacttccct gctgctgaag gccagatgcc tggcttggcc tctctgactg    1260
cccatcctct acctgacctc ccagcctcac cttctgcctc ctgaccgcct cctccctccc    1320
cagctgtgat gggctcactc ttgtccttga acgttccctc caccctaac tgcctctcta    1380
tttccaccc tccacgaat cagagtcagc aacctggaac ctccctcctc agatctgtga    1440
caatctcacc tgctgccacg tggggtcacc aaccctaggt gtagggtggg gtatgtgatt    1500
tctgtctgtg cccagcacca agtcaggctg agagcagcca cagcgtttgt ggaggacaca    1560
gccccactct ctgcccccag gtgccggtgt ctgaaggctg cagccaggct ctgatgcgtc    1620
tcatcggctg tccctgtgc cggggggtcc cctcacttat gccctgccag ggcttctgcc    1680
tcaacgtggt tcgtggctgt ctcagcagca ggggactgga gcctgactgg ggcaactatc    1740
tgggtgaggg gattcaagaa agcctggagc caggcatggt ggctcacacc tgtaatcaca    1800
gcactttgag aggctgaggc aggaggatca cttgaggcca ggagttggag cccagctggg    1860
gcaacatagc tagacgtcat ctcaagaaag aaagaaagag agagagagaa agaaagagag    1920
agagagagac agagaaagaa agaaggaaag aaggaaggaa agaaagaaaa agaaagaaag    1980
aaagaaagaa aagaaagaaa tcagccaggc atggtagcgc ccgcgcctgt agtcccagtt    2040
actcctgagg ctgaggcagg aggatcactt gaggccagga gttggaggcc agcctgggca    2100
acgtagctag accgcatctc tacc                                             2124
```

<210> SEQ ID NO 10

<211> LENGTH: 1743
<212> TYPE: DNA
<213> ORGANISM: Homo sapiens

<400> SEQUENCE: 10

| | | | | | |
|---|---|---|---|---|---|
| atggccggga | ccgtgcgcac | cgcgtgcttg | gtggtggcga | tgctgctcag | cttggacttc | 60 |
| ccgggacagg | cgcagccccc | gccgccgccg | ccggacgcca | cctgtcacca | agtccgctcc | 120 |
| ttcttccaga | gactgcagcc | cggactcaag | tgggtgccag | aaactcccgt | gccaggatca | 180 |
| gatttgcaag | tatgtctccc | taagggccca | acatgctgct | caagaaagat | ggaagaaaaa | 240 |
| taccaactaa | cagcacgatt | gaacatggaa | cagctgcttc | agtctgcaag | tatggagctc | 300 |
| aagttcttaa | ttattcagaa | tgctgcggtt | ttccaagagg | cctttgaaat | tgttgttcgc | 360 |
| catgccaaga | actacaccaa | tgccatgttc | aagaacaact | acccaagcct | gactccacaa | 420 |
| gcttttgagt | tgtgggtga | atttttcaca | gatgtgtctc | tctacatctt | gggttctgac | 480 |
| atcaatgtag | atgacatggt | caatgaattg | tttgacagcc | tgtttccagt | catctatacc | 540 |
| cagctaatga | acccaggcct | gcctgattca | gccttggaca | tcaatgagtg | cctccgagga | 600 |
| gcaagacgtg | acctgaaagt | atttgggaat | tcccccaagc | ttattatgac | ccaggttttcc | 660 |
| aagtcactgc | aagtcactag | gatcttcctt | caggctctga | atcttggaat | tgaagtgatc | 720 |
| aacacaactg | atcacctgaa | gttcagtaag | gactgtggcc | gaatgctcac | cagaatgtgg | 780 |
| tactgctctt | actgccaggg | actgatgatg | gttaaaccct | gtggcggtta | ctgcaatgtg | 840 |
| gtcatgcaag | ctgtatggc | aggtgtggtg | gagattgaca | gtactgcgag | agaatacatt | 900 |
| ctgtcccttg | aagaacttgt | gaatggcatg | tacagaatct | atgacatgga | gaacgtactg | 960 |
| cttggtctct | tttcaacaat | ccatgattct | atccagtatg | tccagaagaa | tgcaggaaag | 1020 |
| ctgaccacca | ctattggcaa | gttatgtgcc | cattctcaac | aacgccaata | tagatctgct | 1080 |
| tattatcctg | aagatctctt | tattgacaag | aaagtattaa | agttgctca | tgtagaacat | 1140 |
| gaagaaaccct | tatccagccg | aagaagggaa | ctaattcaga | agttgaagtc | tttcatcagc | 1200 |
| ttctatagtg | ctttgcctgg | ctacatctgc | agccatagcc | ctgtggcgga | aaacgacacc | 1260 |
| ctttgctgga | atggacaaga | actcgtggag | agatacagcc | aaaaggcagc | aaggaatgga | 1320 |
| atgaaaaacc | agttcaatct | ccatgagctg | aaaatgaagg | gccctgagcc | agtggtcagt | 1380 |
| caaattattg | acaaactgaa | gcacattaac | cagctcctga | gaaccatgtc | tatgcccaaa | 1440 |
| ggtagagttc | tggataaaaa | cctggatgag | gaagggtttg | aaagtggaga | ctgcggtgat | 1500 |
| gatgaagatg | agtgcattgg | aggctctggt | gatggaatga | taaaagtgaa | gaatcagctc | 1560 |
| cgcttccttg | cagaactggc | ctatgatctg | gatgtggatg | atgcgcctgg | aaacagtcag | 1620 |
| caggcaactc | cgaaggacaa | cgagataagc | acctttcaca | acctcgggaa | cgttcattcc | 1680 |
| ccgctgaagc | ttctcaccag | catggccatc | tcggtggtgt | gcttcttctt | cctggtgcac | 1740 |
| tga | | | | | | 1743 |

<210> SEQ ID NO 11
<211> LENGTH: 1671
<212> TYPE: DNA
<213> ORGANISM: Homo sapiens

<400> SEQUENCE: 11

| | | | | | |
|---|---|---|---|---|---|
| atggcacggt | tcggcttgcc | cgcgcttctc | tgcaccctgg | cagtgctcag | cgccgcgctg | 60 |
| ctggctgccg | agctcaagtc | gaaaagttgc | tcggaagtgc | gacgtcttta | cgtgtccaaa | 120 |
| ggcttcaaca | agaacgatgc | ccccctccac | gagatcaacg | tgatcatttt | gaagatctgt | 180 |

```
cccagggtt ctacctgctg ctctcaagag atggaggaga agtacagcct gcaaagtaaa    240
gatgatttca aaagtgtggt cagcgaacag tgcaatcatt tgcaagctgt ctttgcttca    300
cgttacaaga agtttgatga attcttcaaa gaactacttg aaaatgcaga gaaatccctg    360
aatgatatgt ttgtgaagac atatggccat ttatacatgc aaaattctga gctatttaaa    420
gatctcttcg tagagttgaa acgttactac gtggtgggaa atgtgaacct ggaagaaatg    480
ctaaatgact tctgggctcg cctcctggag cggatgttcc gcctggtgaa ctcccagtac    540
cactttacag atgagtatct ggaatgtgtg agcaagtata cggagcagct gaagcccttc    600
ggagatgtcc ctcgcaaatt gaagctccag gttactcgtg cttttgtagc agcccgtact    660
ttcgctcaag gcttagcggt tgcgggagat gtcgtgagca aggtctccgt ggtaaacccc    720
acagcccagt gtacccatgc cctgttgaag atgatctact gctcccactg ccggggtctc    780
gtgactgtga agccatgtta caactactgc tcaaacatca tgagaggctg tttggccaac    840
caagggatc tcgattttga atggaacaat ttcatagatg ctatgctgat ggtggcagag    900
aggctagagg gtcctttcaa cattgaatcg tcatggatcc catcgatgt gaagatttct    960
gatgctatta tgaacatgca ggataatagt gttcaagtgt ctcagaaggt tttccaggga   1020
tgtggacccc ccaagcccct cccagctgga cgaatttctc gttccatctc tgaaagtgcc   1080
ttcagtgctc gcttcagacc acatcacccc gaggaacgcc caaccacagc agctggcact   1140
agtttggacc gactggttac tgatgtcaag gagaaactga acaggccaa gaaattctgg   1200
tcctcccttc cgagcaacgt ttgcaacgat gagaggatgc tgcaggaaa cggcaatgag   1260
gatgactgtt ggaatgggaa aggcaaaagc aggtacctgt ttgcagtgac aggaaatgga   1320
ttagccaacc agggcaacaa cccagaggtc caggttgaca ccagcaaacc agacatactg   1380
atccttcgtc aaatcatggc tcttcgagtg atgaccagca agatgaagaa tgcatacaat   1440
gggaacgacg tggacttctt tgatatcagt gatgaaagta gtggagaagg aagtggaagt   1500
ggctgtgagt atcagcagtg cccttcagag tttgactaca atgccactga ccatgctggg   1560
aagagtgcca atgagaaagc cgacagtgct ggtgtccgtc ctggggcaca ggcctacctc   1620
ctcactgtct tctgcatctt gttcctggtt atgcagagag agtggagata a            1671
```

<210> SEQ ID NO 12  
<211> LENGTH: 1719  
<212> TYPE: DNA  
<213> ORGANISM: Homo sapiens

<400> SEQUENCE: 12

```
atggacgcac agacctggcc cgtgggcttt cgctgcctcc tccttctggc cctggttggg     60
tccgcccgca gcgagggcgt gcagacctgc gaagaagttc ggaaactttt ccagtggcgg    120
ctgctgggag ctgtcagggg gctgccggat tcgccgcggg caggacctga tcttcaggtt    180
tgcatatcca aaaagcctac atgttgcacc aggaagatgg aggagagata tcagattgcg    240
gctcgccagg atatgcagca gtttcttcaa acgtccagct ctacattaaa gtttctaata    300
tctcgaaatg cggctgcttt tcaagaaacc cttgaaactc tcatcaaaca agcagaaaat    360
tacaccagta tacttttttg cagtacctac aggaacatgg ccttgaggc tgctgcttcg    420
gttcaggagt tcttcactga tgtggggctg tatttatttg gtgcggatgt taatcctgaa    480
gaatttgtaa acagattttt tgacagtctt tttcctctgg tctacaacca cctcattaac    540
cctggtgtga ctgacagttc cctggaatac tcagaatgca tccggatggc tcgccgggat    600
```

```
gtgagtccat tggtaatat tccccaaaga gtaatgggac agatgggggag gtccctgctg    660 cccagccgca cttttctgca ggcactcaat ctgggcattg aagtcatcaa caccacagac    720
tatctgcact tctccaaaga gtgcagcaga gccctcctga agatgcaata ctgcccgcac    780
tgccaaggcc tggcgctcac taagccttgt atgggatact gcctcaatgt catgcgaggc    840
tgcctggcgc acatggcgga gcttaatcca cactggcatg catatatccg gtcgttggaa    900
gaactctcgg atgcaatgca tggaacatac gacattggac acgtgctgct gaactttcac    960
ttgcttgtta atgatgctgt gttacaggct cacctcaatg acaaaaatt attggaacag   1020 gtaaatagga tttgtggccg ccctgtaaga cacccacac aaagcccccg ttgttctttt   1080
gatcagagca aagagaagca tggaatgaag accaccacaa ggaacagtga agagacgctt   1140
gccaacagaa gaaaagaatt tatcaacagc cttcgactgt acaggtcatt ctatggaggt   1200
ctagctgatc agctttgtgc taatgaatta gctgctgcag atggacttcc ctgctggaat   1260
ggagaagata tagtaaaaag ttatactcag cgtgtggttg gaaatggaat caaagcccag   1320
tctggaaatc ctgaagtcaa gtcaaagga attgatcctg tgataaatca gattattgat   1380
aaactgaagc atgttgttca gttgttacag ggtagatcac ccaaacctga caagtgggaa   1440
cttcttcagc tgggcagtgg tggaggcatg gttgaacaag tcagtgggga ctgtgatgat   1500
gaagatggtt gcgggggatc aggaagtgga gaagtcaaga ggacactgaa gatcacagac   1560
tggatgccag atgatatgaa cttcagtgat gtaaagcaaa tccatcaaac agacactggc   1620
agtactttag acacaacagg agcaggatgt gcagtggcga ctgaatctat gacattcact   1680
ctgataagtg tggtgatgtt acttcccggg atttggtaa                          1719

<210> SEQ ID NO 13
<211> LENGTH: 2556
<212> TYPE: DNA
<213> ORGANISM: Homo sapiens

<400> SEQUENCE: 13
atgacttccc attatgtgat tgccatcttt gccctgatga gctcctgttt agccactgca     60
ggtccagagc ctggtgcact gtgtgaactg tcacctgtca gtgcctccca tcctgtccag    120
gccttgatgg agagcttcac tgttttgtca ggctgtgcca gcagaggcac aactgggctg    180
ccacaggagg tgcatgtcct gaatctccgc actgcgggcc agggggctgg ccagctacag    240
agagaggtca cacttcacct gaatcccatc tcctcagtcc acatccacca caagtctgtt    300
gtgttcctgc tcaactcccc acaccccctg tgtggcatc tgaagacaga gagacttgcc    360
actggggtct ccagactgtt tttggtgtct gagggttctg tggtccagtt ttcatcagca    420
aacttctcct tgacagcaga aacagaagaa aggaacttcc cccatggaaa tgaacatctg    480
ttaaattggg cccgaaaaga gtatggagca gttacttcat tcaccgaact caagatagca    540
agaaacattt atattaaagt gggggaagat caagtgttcc ctccaaagtg caacataggg    600
aagaattttc tctcactcaa ttaccttgct gagtaccttc aacccaaagc agcagaaggg    660
tgtgtgatgt ccagccagcc ccagaatgag gaagtacaca tcatcgagct aatcaccccc    720
aactctaacc cctacagtgc tttccaggtg gatataacaa ttgatataag accttctcaa    780
gaggatcttg aagtggtcaa aaatctcatc ctgatcttga gtgcaaaaa gtctgtcaac    840 tgggtgatca atctttttga tgttaaggga agcctgaaaa ttattgctcc taacagtatt    900
ggctttggaa aagagagtga agatctctat acaatgacca aatcaataag agatgacatt    960
ccttcaaccc aagggaatct ggtgaagtgg gctttggaca atggctatag tccaataact   1020
```

-continued

| | |
|---|---|
| tcatacacaa tggctcctgt ggctaataga tttcatcttc ggcttgaaaa taatgcagag | 1080 |
| gagatgggag atgaggaagt ccacactatt cctcctgagc tacggatcct gctggaccct | 1140 |
| ggtgccctgc ctgccctgca gaacccgccc atccggggag gggaaggcca aaatggaggc | 1200 |
| cttccgtttc cttcccaga tatttccagg agagtctgga atgaagaggg agaagatggg | 1260 |
| ctccctcggc caaaggaccc tgtcattccc agcatacaac tgtttcctgg tctcagagag | 1320 |
| ccagaagagg tgcaagggag cgtggatatt gccctgtctg tcaaatgtga caatgagaag | 1380 |
| atgatcgtgg ctgtagaaaa agattctttt caggccagtg gctactcggg gatggacgtc | 1440 |
| accctgttgg atcctacctg caaggccaag atgaatggca cacactttgt tttggagtct | 1500 |
| cctctgaatg gctgcggtac tcggcccegg tggtcagccc ttgatggtgt ggtctactat | 1560 |
| aactccattg tgatacaggt tccagcccct ggggacagta gtggttggcc agatggttat | 1620 |
| gaagatctgg agtcaggtga taatggattt ccgggagata tggatgaagg agatgcttcc | 1680 |
| ctgttcaccc gacctgaaat cgtggtgttt aattgcagcc ttcagcaggt gaggaacccc | 1740 |
| agcagcttcc aggaacagcc ccacggaaac atcaccttca acatggagct atacaacact | 1800 |
| gacctctttt tggtgccctc ccagggcgtc ttctctgtgc cagagaatgg acacgtttat | 1860 |
| gttgaggtat ctgttactaa ggctgaacaa gaactgggat tgccatcca acgtgctttt | 1920 |
| atctctccat attcgaaccc tgataggatg tctcattaca ccattattga gaatatttgt | 1980 |
| cctaaagatg aatctgtgaa attctacagt cccaagagag tgcacttccc tatcccgcaa | 2040 |
| gctgacatgg ataagaagcg attcagcttt gtcttcaagc ctgtcttcaa cacctcactg | 2100 |
| ctctttctac agtgtgagct gacgctgtgt acgaagatgg agaagcaccc ccagaagttg | 2160 |
| cctaagtgtg tgcctcctga cgaagcctgc acctcgctgg acgcctcgat aatctgggcc | 2220 |
| atgatgcaga ataagaagac gttcaccaag ccccttgctg tgatccacca tgaagcagaa | 2280 |
| tctaaagaaa aggtccaag catgaaggaa ccaaatccaa tttctccacc aattttccat | 2340 |
| ggtctggaca ccctaaccgt gatgggcatt gcgtttgcag cctttgtgat cggagcactc | 2400 |
| ctgacggggg ccttgtggta catctattct cacacagggg agacagcagg aaggcagcaa | 2460 |
| gtccccacct ccccgccagc ctcggaaaac agcagtgctg cccacagcat cggcagcacg | 2520 |
| cagagcacgc cttgctccag cagcagcacg gcctag | 2556 |

<210> SEQ ID NO 14
<211> LENGTH: 6969
<212> TYPE: DNA
<213> ORGANISM: Homo sapiens

<400> SEQUENCE: 14

| | |
|---|---|
| atgcagtccg ggccgcggcc cccacttcca gcccccggcc tggccttggc tttgaccctg | 60 |
| actatgttgg ccagacttgc atccgcggct tccttcttcg gtgagaacca cctgaggtg | 120 |
| cctgtggcca cggctctgac cgacatagac ctgcagctgc agttctccac gtcccagccc | 180 |
| gaagccctcc ttctcctggc agcaggccca gctgaccacc tcctgctgca gctctactct | 240 |
| ggacgcctgc aggtcagact tgttctgggc caggaggagc tgaggctgca gactccagca | 300 |
| gagacgctgc tgagtgactc catcccccac actgtggtgc tgactgtcgt agagggctgg | 360 |
| gccacgttgt cagtcgatgg gtttctgaac gcctcctcag cagtcccagg agcccccta | 420 |
| gaggtccccct atgggctctt tgttgggggc actgggaccc ttggcctgcc ctacctgagg | 480 |
| ggaaccagcc gaccctgag gggttgcctc catgcagcca ccctcaatgg ccgcagcctc | 540 |

```
ctccggcctc tgaccccga  tgtgcatgag ggctgtgctg aagagttttc tgccagtgat   600
gatgtggccc tgggcttctc tgggcccac  tctctggctg ccttccctgc ctggggcact   660
caggacgaag gaaccctaga gtttacactc accacacaga gccggcaggc acccttggcc   720
ttccaggcag ggggccggcg tggggacttc atctatgtgg acatatttga gggccacctg   780
cgggccgtgg tggagaaggg ccagggtacc gtattgctcc acaacagtgt gcctgtggcc   840
gatgggcagc cccatgaggt cagtgtccac atcaatgctc accggctgga aatctccgtg   900
gaccagtacc ctacgcatac ttcgaaccga ggagtcctca gctacctgga gccacggggc   960
agtctccttc tcgggggct  ggatgcagag gcctctcgtc acctccagga acaccgcctg  1020
ggcctgacac cagaggccac caatgcctcc ctgctgggct gcatggaaga cctcagtgtc  1080
aatggccaga ggcgggggct gcgggaagct ttgctgacgc gcaacatggc agccggctgc  1140
aggctggagg aggaggagta tgaggacgat gcctatggac attatgaagc tttctccacc  1200
ctggccctg  aggcttggcc agccatggag ctgcctgagc catgcgtgcc tgagccaggg  1260
ctgcctcctg tctttgccaa tttcacccag ctgctgacta tcagcccact ggtggtggcc  1320
gagggggca  cagcctggct tgagtggagg catgtgcagc ccacgctgga cctgatggag  1380
gctgagctgc gcaaatccca ggtgctgttc agcgtgaccc gaggggcacg ccatggcgag  1440
ctcgagctgg acatcccggg agcccaggca cgaaaaatgt tcaccctcct ggacgtggtg  1500
aaccgcaagg cccgcttcat ccacgatggc tctgaggaca cctccgacca gctggtgctg  1560
gaggtgtcgt tgacggctcg ggtgcccatg ccctcatgcc ttcggagggg ccaaacatac  1620
ctcctgccca tccaggtcaa ccctgtcaat gacccacccc acatcatctt cccacatggc  1680
agcctcatgg tgatcctgga cacacgcag  aagccgctgg ggcctgaggt tttccaggcc  1740
tatgacccgg actctgcctg tgagggcctc accttccagg tccttggcac ctcctctggc  1800
ctccccgtgg agcgccgaga ccagcctggg gagccggcga ccgagttctc ctgccgggag  1860
ttggaggccg gcagcctagt ctatgtccac cgcggtggtc ctgcacagga cttgacgttc  1920
cgggtcagcg atggactgca ggccagcccc ccggccacgc tgaaggtggt ggccatccgg  1980
ccggccatac agatccaccg cagcacaggg ttgcgactgg cccaaggctc tgccatgccc  2040
atcttgcccg ccaacctgtc ggtggagacc aatgccgtgg ggcaggatgt gagcgtgctg  2100
ttccgcgtca ctggggccct gcagtttggg gagctgcaga agcaggggc  aggtgggggtg  2160
gagggtgctg agtggtgggc cacacaggcg ttccaccagc gggatgtgga gcagggccgc  2220
gtgaggtacc tgagcactga cccacagcac cacgcttacg acaccgtgga gaacctggcc  2280
ctggaggtgc aggtgggcca ggagatcctg agcaatctgt ccttcccagt gaccatccag  2340
agagccactg tgtggatgct gcggctggag ccactgcaca ctcagaacac ccagcaggag  2400
accctcacca cagcccacct ggaggccacc ctggaggagg caggcccaag ccccccaacc  2460
ttccattatg aggtggttca ggctcccagg aaaggcaacc ttcaactaca gggcacaagg  2520
ctgtcagatg gccagggctt cacccaggat gacatacagg ctggccgggt gacctatggg  2580
gccacagcac gtgcctcaga ggcagtcgag gacaccttcc gtttccgtgt cacagctcca  2640
ccatatttct ccccactcta taccttcccc atccacattg gtggtgaccc agatgcgcct  2700
gtcctcacca atgtcctcct cgtggtgcct gagggtggtg agggtgtcct ctctgctgac  2760
cacctctttg tcaagagtct caacagtgcc agctacctct atgaggtcat ggagcggccc  2820
cgccatggga ggttggcttg gcgtgggaca caggacaaga ccactatggt gacatccttc  2880
accaatgaag acctgttgcg tggccggctg gtctaccagc atgatgactc cgagaccaca  2940
```

```
gaagatgata tcccatttgt tgctacccgc cagggcgaga gcagtggtga catggcctgg    3000
gaggaggtac ggggtgtctt ccgagtggcc atccagcccg tgaatgacca cgcccctgtg    3060
cagaccatca gccggatctt ccatgtggcc cggggtgggc ggcggctgct gactacagac    3120
gacgtggcct tcagcgatgc tgactcgggc tttgctgacg cccagctggt gcttacccgc    3180
aaggacctcc tctttggcag tatcgtggcc gtagatgagc ccacgcggcc catctaccgc    3240
ttcacccagg aggacctcag gaagaggcga gtactgttcg tgcactcagg ggctgaccgt    3300
ggctggatcc agctgcaggt gtccgacggg caacaccagg ccactgcgct gctggaggtg    3360
caggcctcgg aaccctacct ccgtgtggcc aacggctcca gccttgtggt ccctcaagga    3420
ggccagggca ccatcgacac ggccgtgctc cacctggaca ccaacctcga catccgcagt    3480
ggggatgagg tccactacca cgtcacagct ggccctcgct ggggacagct agtccgggct    3540
ggtcagccag ccacagcctt ctcccagcag gacctgctgg atggggccgt tctctatagc    3600
cacaatggca gcctcagccc ccgcgacacc atggccttct ccgtggaagc agggccagtg    3660 cacacgatg ccaccctaca agtgaccatt gccctagagg gcccactggc cccactgaag    3720
ctggtccggc acaagaagat ctacgtcttc cagggagagg cagctgagat cagaagggac    3780
cagctggagg cagcccagga ggcagtgcca cctgcagaca tcgtattctc agtgaagagc    3840
ccaccgagtg ccggctacct ggtgatggtg tcgcgtggcg ccttggcaga tgagccaccc    3900
agcctggacc ctgtgcagag cttctcccag gaggcagtgg acacaggcag ggtcctgtac    3960
ctgcactccc gccctgaggc ctggagcgat gccttctcgc tggatgtggc ctcaggcctg    4020
ggtgctcccc tcgagggcgt ccttgtggag ctggaggtgc tgcccgctgc catcccacta    4080
gaggcgcaaa acttcagcgt ccctgagggt ggcagcctca ccctggcccc tccactgctc    4140
cgtgtctccg ggccctactt ccccactctc ctgggcctca gctgcaggt gctggagcca    4200 ccccagcatg gagccctgca gaaggaggac ggacctcaag ccaggaccct cagcgccttc    4260
tcctggagaa tggtggaaga gcagctgatc cgctacgtgc atgacgggag cgagacactg    4320
acagacagtt ttgtcctgat ggctaatgcc tccgagatgg atcgcagag ccatcctgtg    4380 gccttcactg tcactgtcct gcctgtcaat gaccaacccc ccatcctcac tacaaacaca    4440
ggcctgcaga tgtgggaggg ggccactgcg cccatccctg cggaggctct gaggagcacg    4500
gacggcgact ctgggtctga ggatctggtc tacaccatcg agcagcccag caacgggcgg    4560
gtagtgctgc ggggggcgcc gggcactgag gtgcgcagct tcacgcaggc ccagctggac    4620
ggcgggctcg tgctgttctc acacagagga accctggatg gaggcttccg cttccgcctc    4680
tctgacggcg agcacacttc ccccggacac ttcttccgag tgacgcccca gaagcaagtg    4740
ctcctctcgc tgaagggcag ccagacactg actgtctgcc cagggtccgt ccagccactc    4800
agcagtcaga ccctcagggc cagctccagc gcaggcactg accccagct cctgctctac    4860 cgtgtggtgc ggggcccca gctaggccgg ctgttccacg cccagcagga cagcacaggg    4920
gaggccctgg tgaacttcac tcaggcagag gtctacgctg gaatattct gtatgagcat    4980 gagatgcccc ccgagcccct ttgggaggcc catgataccc tagagctcca gctgtcctcg    5040
ccgcctgccc gggacgtggc cgccaccctt gctgtggctg tgtcttttga ggctgcctgt    5100
ccccagcgcc ccagccacct ctggaagaac aaaggtctct gggtcccga gggccagcgg    5160 gccaggatca ccgtgctgc tctgatgcc tccaatctct tggccagcgt tccatcaccc    5220
cagcgctcag agcatgatgt gctcttccag gtcacacagt tccccagccg gggccagctg    5280
```

```
ttggtgtccg aggagcccct ccatgctggg cagccccact tcctgcagtc ccagctggct    5340
gcagggcagc tagtgtatgc ccacggcggt gggggcaccc agcaggatgg cttccacttt    5400
cgtgcccacc tccaggggcc agcagggggcc tccgtggctg accccaaac ctcagaggcc    5460 tttgccatca cggtgaggga tgtaaatgag cggccccctc agccacaggc ctctgtccca    5520
ctccggctca cccgaggctc tcgtgcccccc atctcccggg cccagctgag tgtggtggac    5580
ccagactcag ctcctgggga gattgagtac gaggtccagc gggcacccca caacggcttc    5640
ctcagcctgg tgggtggtgg cctggggccc gtgacccgct tcacgcaagc cgatgtggat    5700
tcagggcggc tggccttcgt ggccaacggg agcagcgtgg caggcatctt ccagctgagc    5760
atgtctgatg gggccagccc acccctgccc atgtccctgg ctgtggacat cctaccatcc    5820
gccatcgagg tgcagctgcg ggcacccctg gaggtgcccc aagctttggg gcgctcctca    5880
ctgagccagc agcagctccg ggtggtttca gatcgggagg agccagaggc agcataccgc    5940
ctcatccagg accccagta tgggcatctc tggtgggcg gcggccccac ctcggccttc    6000
agccaattcc agatagacca gggcgaggtg gtctttgcct tcaccaactt ctcctcctct    6060
catgaccact tcagagtcct ggcactggct agggtgtca atgcatcagc cgtagtgaac    6120
gtcactgtga gggctctgct gcatgtgtgg gcaggtgggc catggcccca gggtgccacc    6180
ctgcgcctgg accccaccgt cctagatgct ggcgagctgg ccaaccgcac aggcagtgtg    6240
ccgcgcttcc gcctcctgga gggaccccgg catggccgcg tggtccgcgt gccccgagcc    6300
aggacggagc ccggggcag ccagctggtg gagcagttca ctcagcagga ccttgaggac    6360
gggaggctgg ggctggaggt gggcaggcca gaggggaggg cccccggccc cgcaggtgac    6420
agtctcactc tggagctgtg gcacagggc gtcccgcctg ctgtggcctc cctggacttt    6480
gccactgagc cttacaatgc tgcccggccc tacagcgtgg ccctgctcag tgtccccgag    6540
gccgcccgga cggaagcagg gaagccgaga gcagcaccc cacaggcga gccaggcccc    6600 atggcatcca gccctgagcc cgctgtggcc aagggaggct tcctgagctt ccttgaggcc    6660
aacatgttca gcgtcatcat ccccatgtgc ctggtacttc tgctcctggc gctcatcctg    6720
cccctgctct tctacctccg aaaacgcaac aagacgggca agcatgacgt ccaggtcctg    6780
actgccaagc cccgcaacgg cctggctggt gacaccgaga cctttcgcaa ggtggagcca    6840
ggccaggcca tcccgctcac agctgtgcct ggccagggc cccctccagg aggccagcct    6900
gacccagagc tgctgcagtt ctgccggaca cccaaccctg cccttaagaa tggccagtac    6960
tgggtgtga                                                            6969

<210> SEQ ID NO 15
<211> LENGTH: 2232
<212> TYPE: DNA
<213> ORGANISM: Homo sapiens

<400> SEQUENCE: 15
accatggaca gttttggtg gcacgcagcc tggggactct gcctcgtgcc gctgagcctg      60
gcgcagatcg atttgaatat aacctgccgc tttgcaggtg tattccacgt ggagaaaaat     120
ggtcgctaca gcatctctcg gacggaggcc gctgacctct gcaaggcttt caatagcacc     180
ttgcccacaa tggcccagat ggagaaagct ctgagcatcg gatttgagac ctgcaggtat     240
gggttcatag aagggcacgt ggtgattccc cggatccacc ccaactccat ctgtgcagca     300
aacaacacag gggtgtacat cctcacatcc aacacctccc agtatgacac atattgcttc     360
aatgcttcag ctccacctga agaagattgt acatcagtca cagacctgcc caatgccttt     420
```

-continued

```
gatggaccaa ttaccataac tattgttaac cgtgatggca cccgctatgt ccagaaagga      480
gaatacagaa cgaatcctga agacatctac cccagcaacc ctactgatga tgacgtgagc      540
agcggctcct ccagtgaaag gagcagcact tcaggaggtt acatctttta cacctttcct      600
actgtacacc ccatcccaga cgaagacagt ccctggatca ccgacagcac agacagaatc      660
cctgctacca ctttgatgag cactagtgct acagcaactg agacagcaac caagaggcaa      720
gaaacctggg attggttttc atggttgttt ctaccatcag agtcaaagaa tcatcttcac      780
acaacaacac aaatggctgg tacgtcttca aataccatct cagcaggctg ggagccaaat      840
gaagaaaatg aagatgaaag agacagacac ctcagttttt ctggatcagg cattgatgat      900
gatgaagatt ttatctccag caccatttca accacaccac gggcttttga ccacacaaaa      960
cagaaccagg actggaccca gtggaaccca agccattcaa atccggaagt gctacttcag     1020
acaaccacaa ggatgactga tgtagacaga atggcacca ctgcttatga aggaaactgg      1080
aacccagaag cacaccctcc cctcattcac catgagcatc atgaggaaga agagaccccca    1140 cattctacaa gcacaatcca ggcaactcct agtagtacaa cggaagaaac agctacccag     1200
aaggaacagt ggtttggcaa cagatggcat gagggatatc gccaaacacc caagaagac     1260 tcccattcga caacagggac agctgcagcc tcagctcata ccagccatcc aatgcaagga     1320
aggacaacac caagcccaga ggacagttcc tggactgatt tcttcaaccc aatctcacac     1380
cccatgggac gaggtcatca agcaggaaga aggatggata tggactccag tcatagtata     1440
acgcttcagc ctactgcaaa tccaaacaca ggtttggtgg aagatttgga caggacagga     1500
cctctttcaa tgacaacgca gcagagtaat tctcagagct ctctacatc acatgaaggc      1560 ttggaagaag ataaagacca tccaacaact tctactctga catcaagcaa taggaatgat     1620
gtcacaggtg aagaagaga cccaaatcat tctgaaggct caactacttt actggaaggt      1680
tatacctctc attacccaca cacgaaggaa agcaggacct tcatcccagt gacctcagct     1740
aagactgggt cctttggagt tactgcagtt actgttggag attccaactc taatgtcaat     1800
cgttccttat caggagacca agacacattc cacccagtg gggggtccca taccactcat      1860
ggatctgaat cagatggaca ctcacatggg agtcaagaag gtggagcaaa cacaacctct     1920
ggtcctataa ggacacccca aattccgaaa tggctgatca tcttggcatc cctcttggcc     1980
ttggctttga ttcttgcagt ttgcattgca gtcaacagtc gaagaaggtg tgggcagaag     2040
aaaaagctag tgatcaacag tggcaatgga gctgtgagg acagaaagcc aagtggactc     2100
aacggagagg ccagcaagtc tcaggaaatg gtgcatttgg tgaacaagga gtcgtcagaa     2160
actccagacc agtttatgac agctgatgag acaaggaacc tgcagaatgt ggacatgaag     2220
attggggtgt aa                                                          2232
```

<210> SEQ ID NO 16
<211> LENGTH: 1137
<212> TYPE: DNA
<213> ORGANISM: Homo sapiens

<400> SEQUENCE: 16

```
gacaaaatgc agtggacctc cctcctgctg ctggcagggc tcttctccct ctcccaggcc       60
cagtatgaag atgaccctca ttggtggttc cactacctcc gcagccagca gtccacctac      120
tacgatccct atgaccctta cccgtatgag acctacgagc cttacccta tgggggtggat      180 gaagggccag cctacaccta cggctctcca tcccctccag atccccgcga ctgccccag       240
```

-continued

```
gagtgcgact gcccacccaa cttccccacg gccatgtact gtgacaatcg caacctcaag    300
tacctgccct tcgttccctc ccgcatgaag tatgtgtact tccagaacaa ccagatcacc    360
tccatccagg aaggcgtctt tgacaatgcc acagggctgc tctggattgc tctccacggc    420
aaccagatca ccagtgataa ggtgggcagg aaggtcttct ccaagctgag gcacctggag    480
aggctgtacc tggaccacaa caacctgacc cggatgcccg tcccctgcc tcgatccctg      540 agagagctcc atctcgacca caaccagatc tcacgggtcc ccaacaatgc tctggagggg    600
ctggagaacc tcacggcctt gtacctccaa cacaatgaga tccaggaagt gggcagttcc    660 atgagggcc tccggtcact gatcttgctg gacctgagtt ataaccacct tcggaaggtg      720
cctgatgggc tgccctcagc tcttgagcag ctgtacatgg agcacaacaa tgtctacacc    780
gtccccgata gctacttccg gggggcgccc aagctgctgt atgtgcggct gtcccacaac    840
agtctaacca acaatggcct ggcctccaac accttcaatt ccagcagcct ccttgagcta    900
gacctctcct acaaccagct gcagaagatc cccccagtca acaccaacct ggagaacctc    960
tacctccaag gcaataggat caatgagttc tccatcagca gcttctgcac cgtggtggac   1020
gtcgtgaact tctccaagct gcaggtgctg cgcctggacg ggaacgagat caagcgcagc   1080
gccatgcctg ccgacgcgcc cctctgcctg cgccttgcca gcctcatcga gatctga      1137
```

<210> SEQ ID NO 17
<211> LENGTH: 1149
<212> TYPE: DNA
<213> ORGANISM: Homo sapiens

<400> SEQUENCE: 17

```
atgaggtcac ccctctgctg gctcctccca cttctcatct tggcctcagt ggcccaaggc     60
cagccaacaa gacgaccaag acccgggact gggcccgggc gcagacccag gcccaggccc    120
aggcccacac ccagctttcc tcagcctgat gaaccagcag agccaacaga cctgcctcct    180 cccctcccc caggccctcc atctatcttc cctgactgtc cccgcgaatg ctactgcccc    240
cctgatttcc catctgccct ctactgtgat agccgcaacc tgcgaaaggt ccctgtcatc    300
ccgccccgca tccattacct ctatctccag aacaacttca tcactgagct cccggtggag    360
tccttccaga atgccacagg cctgcgatgg attaacctgg acaacaaccg aatccgcaag    420
atagaccaga gggtgctgga aaactgcccc ggcctggtgt cctctacat ggagaagaac     480 cagttggaag aggtccctc ggccctgccc cggaacctgg agcagctgag gctgagccag    540
aaccacatct ccagaatccc gcctggtgtc ttcagcaagc tggagaacct gctgctcctg    600
gatctccagc acaacaggct gagcgacggc gtcttcaagc ccgacacctt ccatggcctc    660
aagaacctca tgcagctcaa cctggcccac aacatcctga aaagatgcc gcccagggtc    720 cccaccgcca ttcaccagct ctacctggac agtaacaaga ttgagaccat ccctaacgga    780
tacttcaaga gctttcccaa tcttgccttc attcggctta actacaacaa gctgacagac    840
aggggactcc ccaagaactc ctttaatatc tccaacctgc ttgtgctcca cctgtcccac    900
aacaggatca gcagtgtgcc cgccatcaac aacaggctgg aacacctgta cctcaacaac    960
aatagcatcg agaaaatcaa cggaacccag atttgcccca cgacctagt ggcgttccat   1020 gacttctcct cggacctgga gaacgtgcca cacctgcgct acctgcggct ggatggaaac   1080
tacttgaagc cgcccatccc gctggacctc atgatgtgct tccgcctcct gcagtccgtg   1140
gtcatctag                                                           1149
```

<210> SEQ ID NO 18
<211> LENGTH: 1068
<212> TYPE: DNA
<213> ORGANISM: Homo sapiens

<400> SEQUENCE: 18

| | | | | | |
|---|---|---|---|---|---|
| ggtgctataa | tggcaggcac | aatctgtttc | atcatgtggg | tgttattcat | aacagacact | 60 |
| gtgtggtcta | gaagtgtgag | gcaggtctat | gaagtacatg | attcagatga | ttggactatt | 120 |
| catgacttcg | agtgtcccat | ggaatgtttc | tgcccaccca | gttttcctac | tgctttatat | 180 |
| tgtgaaaata | gaggtctcaa | agaaattcct | gctattcctt | caagaatttg | gtatctttat | 240 |
| cttcaaaaca | acctgataga | aaccattcct | gaaaagccat | ttgagaatgc | cacccagcta | 300 |
| agatggataa | atctaaacaa | gaacaaaata | accaactacg | gaattgaaaa | aggagcccta | 360 |
| agccagctga | agaagttgct | cttcttattt | ctggaagata | atgagctaga | ggaggtacct | 420 |
| tctccattgc | caagaagttt | agaacaatta | caattagcta | gaaataaggt | gtccagaatt | 480 |
| cctcaaggga | cctttagcaa | tctggagaac | ctgacccttc | ttgacctaca | gaacaacaaa | 540 |
| ttagtggaca | atgcctttca | aagagacact | tttaaaggac | tcaagaatct | catgcagcta | 600 |
| aacatggcca | agaatgccct | gaggaatatg | cctccaagat | accagccaa | tacaatgcag | 660 |
| ttgttttag | acaacaattc | cattgaagga | ataccagaaa | attatttaa | tgtgattcct | 720 |
| aaagtggcct | ttttgagact | aaatcacaac | aaactgtcag | atgagggtct | cccatcaaga | 780 |
| ggatttgatg | tatcatcaat | tctagatctt | caactgtcgc | acaatcaact | cacaaaggtt | 840 |
| ccccgaatca | gtgctcatct | gcagcacctt | caccttgatc | ataacaaaat | taaaagtgtg | 900 |
| aatgtctctg | taatatgtcc | cagcccatcc | atgctgcctg | cagaacgaga | ttccttcagt | 960 |
| tatgaccctc | atcttcgcta | cctccgtctg | gatggaaatg | aaatcaaacc | accaattcca | 1020 |
| atggctttaa | tgacctgctt | cagacttctg | caggctgtca | ttatttaa | | 1068 |

<210> SEQ ID NO 19
<211> LENGTH: 1266
<212> TYPE: DNA
<213> ORGANISM: Homo sapiens

<400> SEQUENCE: 19

| | | | | | |
|---|---|---|---|---|---|
| atgggttttt | taagtccaat | atatgttatt | ttcttctttt | ttggagtcaa | agtacattgc | 60 |
| caatatgaaa | cttatcagtg | ggatgaagac | tatgaccaag | agccagatga | tgattaccaa | 120 |
| acaggattcc | catttcgtca | aaatgtagac | tacggagttc | cttttcatca | gtatacttta | 180 |
| ggctgtgtca | gtgaatgctt | ctgtccaact | aactttccat | catcaatgta | ctgtgataat | 240 |
| cgcaaactca | agactatccc | aaatattccg | atgcacattc | agcaactcta | ccttcagttc | 300 |
| aatgaaattg | aggctgtgac | tgcaaattca | ttcatcaatg | caactcatct | taaagaaatt | 360 |
| aacctcagcc | acaacaaaat | taatctcaa | aagattgatt | atggtgtgtt | tgctaagctt | 420 |
| ccaaatctac | tacaacttca | tctagagcat | aataatttag | aagaatttcc | atttcctctt | 480 |
| cctaaatctc | tggaaagact | ccttcttggt | tacaatgaaa | tctccaaact | gcagacaaat | 540 |
| gctatggatg | ggctagtaaa | cttgaccatg | cttgatctct | gttataatta | tcttcatgat | 600 |
| tctctgctaa | aagacaaaat | ctttgccaaa | atggaaaaac | taatgcagct | caacctctgc | 660 |
| agtaacagat | tagaatcaat | gcctcctggt | ttgccttctt | cacttatgta | tctgtctta | 720 |
| gaaataatt | caatttcttc | tatacccgaa | aaatacttcg | acaaacttcc | aaaacttcat | 780 |
| actctaagaa | tgtcacacaa | caaactacaa | gacatcccat | ataatatttt | taatcttccc | 840 |

```
aacattgtag aactcagtgt tggacacaac aaattgaagc aagcattcta tattccaaga    900
aatttggaac acctatacct acaaaataat gaaatagaaa agatgaatct tacagtgatg    960
tgtccttcta ttgacccact acattaccac catttaacat acattcgtgt ggaccaaaat   1020
aaactaaaag aaccaataag ctcatacatc ttcttctgct tccctcatat acacactatt   1080
tattatggtg aacaacgaag cactaatggt caaacaatac aactaaagac acaagttttc   1140
aggagatttc cagatgatga tgatgaaagt gaagatcacg atgatcctga caatgctcat   1200
gagagcccag aacaagaagg agcagaaggg cactttgacc ttcattatta tgaaaatcaa   1260
gaatag                                                              1266

<210> SEQ ID NO 20
<211> LENGTH: 969
<212> TYPE: DNA
<213> ORGANISM: Homo sapiens

<400> SEQUENCE: 20
atgaagacat tagcaggact tgttctggga cttgtcatct ttgatgctgc tgtgactgcc     60
ccaactctag agtccatcaa ctatgactca gaaacctatg atgccacctt agaagacctg    120
gataatttgt acaactatga aaacatacct gttgataaag ttgagattga aatagccaca    180
gtgatgcctt cagggaacag agagctcctc actccacccc cacagcctga aaggcccag     240 gaagaggaag aggaggagga atctactccc aggctgattg atggctcttc tccccaggag    300
cctgaattca cagggttct ggggccacac acaaatgaag actttccaac ctgtcttttg    360
tgtacttgta taagtaccac cgtgtactgt gatgaccatg aacttgatgc tattcctccg    420
ctgccaaaga acaccgctta tttctattcc cgctttaaca gaattaaaaa gatcaacaaa    480
aatgactttg caagcctaag tgatttaaaa aggattgatc tgacatcaaa tttaatatct    540
gagattgatg aagatgcatt ccgaaaactg cctcaacttc gagagcttgt cctgcgtgac    600
aacaaaataa ggcagctccc agaattgcca accactttga catttattga tattagcaac    660
aatagacttg gaaggaaagg gataaagcaa gaagcattta aagacatgta tgatctccat    720
catctgtacc tcactgataa caacttggac cacatccctc tgccactccc agaaaatcta    780
cgagcccttc acctccagaa taacaacatt ctggaaatgc acgaagatac gttctgcaat    840
gttaaaaatt tgacttatat tcgtaaggca ctagaggaca ttcgattgga tggaaaccct    900
attaatctca gcaaaactcc tcaagcatac atgtgtctac ctcgtctgcc tgttgggagc    960
cttgtctaa                                                            969

<210> SEQ ID NO 21
<211> LENGTH: 897
<212> TYPE: DNA
<213> ORGANISM: Homo sapiens

<400> SEQUENCE: 21
atgaagactc tgcagtctac acttctcctg ttactgcttg tgcctctgat aaagccagca     60
ccaccaaccc agcaggactc acgcattatc tatgattatg aacagataa ttttgaagaa    120 tccatattta gccaagatta tgaggataaa tacctggatg aaaaaatat taaggaaaaa    180 gaaactgtga taatacccaa tgagaaaagt cttcaattac aaaaagatga ggcaataaca    240
ccattacctc ccaagaaaga aaatgatgaa atgcccacgt gtctgctgtg tgtttgttta    300
agtggctctg tatactgtga agaagttgac attgatgctg taccacccct accaaaggaa    360
tcagcctatc tttacgcacg attcaacaaa attaaaaagc tgactgccaa agattttgca    420
```

```
gacataccta acttaagaag actcgatttt acgggaaatt tgatagaaga tatagaagat       480 ggtactttt  caaaactttc tctgttagaa gaactttcac ttgctgaaaa tcaactacta      540
aaacttccag ttcttcctcc caagctcact ttatttaatg caaaatacaa caaaatcaag      600
agtaggggaa tcaaagcaaa tgcattcaaa aaactgaata acctcacctt cctctacttg      660
gaccataatg ccctggaatc cgtgcctctt aatttaccag aaagtctacg tgtaattcat      720
cttcagttca acaacatagc ttcaattaca gatgacacat tctgcaaggc taatgacacc      780
agttacatcc gggaccgcat tgaagagata cgcctggagg gcaatccaat cgtcctggga      840
aagcatccaa acagttttat ttgcttaaaa agattaccga tagggtcata cttttaa        897

<210> SEQ ID NO 22
<211> LENGTH: 3966
<212> TYPE: DNA
<213> ORGANISM: Homo sapiens

<400> SEQUENCE: 22
atgggggccc cgtttgtctg ggccttgggc cttttgatgc tgcagatgct gctctttgtg       60
gctggggaac agggcacaca ggatatcacc gatgccagcg aaaggggggct ccacatgcag     120 aagctggggt ctgggtcagt gcaggctgcg ctggcggagc tggtggccct gccctgtctc     180
tttaccctgc agccacggcc aagcgcagcc cgagatgccc ctcggataaa gtggaccaag     240
gtgcggactg cgtcgggcca gcgacaggac ttgcccatcc tggtggccaa ggacaatgtc     300
gtgagggtgg ccaaaagctg gcaggacga  gtgtcactgc cttcctaccc ccggcgccga     360
gccaacgcca cgctacttct ggggccactg agggccagtg actctgggct gtaccgctgc     420
caggtggtga gggcatcga  ggatgagcag gacctggtgc ccttggaggt gacaggtgtt     480
gtgttccact accgatcagc ccggaccgc  tatgcactga ccttcgctga ggcccaggag     540
gcctgccgtc tcagctcagc catcattgca gcccctcggc atctacaggc tgccttggag     600
gatggctttg acaactgtga tgctggctgg ctctctgacc gcactgttcg gtatcctatc     660
acccagtccc gtcctggttg ctatggcgac cgtagcagcc ttccaggggt tcggagctat     720
gggaggcgca acccacagga actctacgat gtgtattgct ttgcccggga gctgggggc     780 gaggtcttct acgtgggccc ggccgccgc  ctgacactgg ccggcgcgcg tgcacagtgc     840
cgccgccagg gtgccgcgct ggcctcggtg ggacagctgc acctggcctg gcatgagggc     900
ctggaccagt gcgacccggg ctggctggcc gacggcagcg tgcgctaccc gatccagacg     960
ccgcgccggc gctgcgggg  cccagccccg ggcgtgcgca ccgtctaccg cttcgctaac    1020
cggaccggct tcccctcacc cgccgagcgc ttcgacgcct actgcttccg agctcatcac    1080
cccacgtcac aacatggaga cctagagacc ccatcctctg gggatgaggg ggagattctg    1140
tcagcagagg ggcccccagt tagagaactg gagcccaccc tggaggagga agaggtggtc    1200 accccctgact tccaggagcc tctggtgtcc agtgggggaag aagaaaccct gatttttggag   1260 gagaagcagg agtctcaaca gaccctcagc cctacccctg ggacccccat gctggcctca    1320
tggcccactg gggaagtgtg gctaagcacg gtggccccca gccctagcga catggggggca   1380 ggcactgcag caagttcaca cacggaggtg gcccccaactg acctatgcc  taggagaagg    1440 gggcgcttca aagggttgaa tgggcgctac ttccagcagc aggaaccgga gccggggctg    1500 caaggggggga tggaggccag cgcccagccc cccacctcag aggctgcagt gaaccaaatg    1560
gagcctccgt tggccatggc agtcacagag atgttgggca gtggccagag ccggagcccc    1620
```

```
tgggctgatc tgaccaatga ggtggatatg cctggagctg gttctgctgg tggcaagagc   1680
tcccccagagc cctggctgtg gcccccctacc atggtcccac ccagcatctc aggccacagc   1740
agggcccctg tcctggagct agagaaagcc gagggcccca gtgccaggcc agccaccccca  1800
gacctgtttt ggtcccccctt ggaggccact gtctcagctc ccagccctgc ccctgggag   1860
gcattccctg tggccacctc cccagatctc cctatgatgg ccatgctgcg tggtcccaaa   1920
gagtggatgc taccacaccc caccccccatc tccaccgagg ccaatagagt tgaggcacat  1980
ggtgaggcca ccgccacggc tccaccctcc cctgctgcag agaccaaggt gtattccctg   2040
cctctctctt tgaccccaac aggacagggt ggagaggcca tgcccacaac acctgagtcc   2100
cccagggcag acttcagaga aactggggag accagccctg ctcaggtcaa caaagctgag   2160
cactccagct ccagcccatg gccttctgta acaggaatg tggctgtagg ttttgtcccc   2220
actgagactg ccactgagcc aacgggcctc aggggtatcc cggggtctga gtctggggtc   2280
ttcgacacag cagaaagccc cacttctggc ttgcaggcca ctgtagatga ggtgcaggac   2340
ccctggccct cagtgtacag caaagggctg gatgcaagtt ccccatctgc cccctgggg   2400
agccctggag tcttcttggt acccaaagtc accccaaatt tggagccttg ggttgctaca   2460
gatgaaggac ccactgtgaa tcccatggat tccacagtca cgccggcccc cagtgatgct   2520
agtggaatttt gggaacctgg atcccaggtg tttgaagaag ccgaaagcac caccttgagc   2580
cctcaggtgg ccctggatac aagcattgtg acgcccctca cgaccctgga cagggggac   2640
aaggttggag ttccagccat gtctacactg ggctcctcaa gctcccaacc ccacccagag   2700
ccagaggatc aggtggagac ccagggaaca tcaggagctt cagtgcctcc gcatcagagc   2760
agtcccctag ggaaaccggc tgttcctcct gggacaccga ctgcagccag tgtgggcgag   2820
tctgcctcag tttcctcagg ggagcctacg gtaccgtggg acccctccag caccctgctg   2880
cctgtcaccc tgggcataga ggacttcgaa ctggaggtcc tggcagggag cccgggtgta   2940
gagagcttct gggaggaggt ggcaagtgga gaggagccag ccctgccagg gaccccctatg  3000
aatgcaggtg cggaggaggt gcactcagat ccctgtgaga caaccccttg tcttcatgga   3060
gggacatgta atgccaatgg caccatgtat ggctgtagct gtgatcaggg cttcgccggg   3120
gagaactgtg agattgacat tgatgactgc ctctgcagcc cctgtgagaa tggaggcacc   3180
tgtattgatg aggtcaatgg ctttgtctgc ctttgcctcc ccagctatgg gggcagcttt   3240
tgtgagaaag acaccgaggg ctgtgaccgc ggctggcata agttccaggg ccactgttac   3300
cgctattttg cccaccggag ggcatgggaa gatgccgaga aggactgccg ccgccgctcc   3360
ggccacctga ccagcgtcca ctcaccggag gaacacagct tcattaatag ctttgggcat   3420
gaaaacacgt ggatcggcct gaacgacagg atcgtggaga gagatttcca gtggacggac   3480
aacaccgggc tgcaatttga gaactggcga gagaaccagc cggacaattt cttcgcgggt   3540
ggcgaggact gtgtggtgat ggtggcgcat gaaagcgggc gctggaacga tgtcccctgc   3600
aactacaacc tacccctatgt ctgcaagaag gcacagtgc tctgtggtcc ccctccggca   3660
gtggagaatg cctcactcat cggtgcccgc aaggccaagt acaatgtcca tgccactgta   3720
aggtaccagt gcaatgaagg atttgcccag caccatgtgg ccaccattcg atgccggagc   3780
aatggcaagt gggacaggcc ccaaattgtc tgcaccaaac ccagacgttc acatcggatg   3840
cggcgacacc accaccacca ccaacaccac caccagcatc accaccacaa atcccgcaag   3900
gagcgcagaa aacacaagaa acacccaacg gaggactggg agaaggacga agggaatttc   3960
tgctga                                                              3966
```

<210> SEQ ID NO 23
<211> LENGTH: 2736
<212> TYPE: DNA
<213> ORGANISM: Homo sapiens

<400> SEQUENCE: 23

| | | | | | |
|---|---|---|---|---|---|
| atgcccagc | tgttcctgcc | cctgctggca | gccctggtcc | tggcccaggc | tcctgcagct | 60 |
| ttagcagatg | ttctggaagg | agacagctca | gaggaccgcg | cttttcgcgt | gcgcatcgcg | 120 |
| ggcgacgcgc | cactgcaggg | cgtgctcggc | ggcgccctca | ccatcccttg | ccacgtccac | 180 |
| tacctgcggc | caccgccgag | ccgccgggct | gtgctgggct | ctccgcgggt | caagtggact | 240 |
| ttcctgtccc | ggggccggga | ggcagaggtg | ctggtggcgc | ggggagtgcg | cgtcaaggtg | 300 |
| aacgaggcct | accggttccg | cgtggcactg | cctgcgtacc | cagcgtcgct | caccgacgtc | 360 |
| tccctggcgc | tgagcgagct | cgcccccaac | gactcaggta | tctatcgctg | tgaggtccag | 420 |
| cacggcatcg | atgacagcag | cgacgctgtg | gaggtcaagg | tcaaggggt | cgtctttctc | 480 |
| taccgagagg | gctctgcccg | ctatgctttc | tccttttctg | gggcccagga | ggcctgtgcc | 540 |
| cgcattggag | cccacatcgc | caccccggag | cagctctatg | ccgcctacct | tgggggctat | 600 |
| gagcaatgtg | atgctggctg | gctgtcggat | cagaccgtga | ggtatcccat | ccagacccca | 660 |
| cgagaggcct | gttacggaga | catggatggc | ttccccgggg | tccggaacta | tggtgtggtg | 720 |
| gacccggatg | acctctatga | tgtgtactgt | tatgctgaag | acctaaatgg | agaactgttc | 780 |
| ctgggtgacc | tccagagaaa | gctgacattg | gaggaagcac | gggcgtactg | ccaggagcgg | 840 |
| ggtgcagaga | ttgccaccac | gggccaactg | tatgcagcct | gggatggtgg | cctggaccac | 900 |
| tgcagcccag | ggtggctagc | tgatggcagt | gtgcgctacc | ccatcgtcac | acccagccag | 960 |
| cgctgtggtg | ggggcttgcc | tggtgtcaag | actctcttcc | tcttcccaa | ccagactggc | 1020 |
| ttccccaata | agcacagccg | cttcaacgtc | tactgcttcc | gagactcggc | ccagccttct | 1080 |
| gccatccctg | aggcctccaa | cccagcctcc | aacccagcct | ctgatggact | agaggctatc | 1140 |
| gtcacagtga | cagagaccct | ggaggaactg | cagctgcctc | aggaagccac | agagagtgaa | 1200 |
| tcccgtgggg | ccatctactc | catccccatc | atggaggacg | gaggaggtgg | aagctccact | 1260 |
| ccagaagacc | cagcagaggc | cctaggacg | ctcctagaat | ttgaaacaca | atccatggta | 1320 |
| ccgcccacgg | ggttctcaga | gaggaaggt | aaggcattgg | aggaagaaga | gaaatatgaa | 1380 |
| gatgaagaag | agaaagagga | ggaagaagaa | gaggaggagg | tggaggatga | ggctctgtgg | 1440 |
| gcatggccca | gcgagctcag | cagcccgggc | cctgaggcct | ctctcccac | tgagccagca | 1500 |
| gcccaggagg | agtcactctc | ccaggcgcca | gcaagggcag | tcctgcagcc | tggtgcatca | 1560 |
| ccacttcctg | atggagagtc | agaagcttcc | aggcctccaa | gggtccatgg | accacctact | 1620 |
| gagactctgc | ccactcccag | ggagaggaac | ctagcatccc | catcaccttc | cactctggtt | 1680 |
| gaggcaagag | aggtggggga | ggcaactggt | ggtcctgagc | tatctggggt | ccctcgagga | 1740 |
| gagagcgagg | agacaggaag | ctccgagggt | gcccctccc | tgcttccagc | cacacgggcc | 1800 |
| cctgagggta | ccagggagct | ggaggcccc | tctgaagata | attctggaag | aactgcccca | 1860 |
| gcagggacct | cagtgcaggc | ccagccagtg | ctgcccactg | acagcgccag | ccgaggtgga | 1920 |
| gtggccgtgg | tccccgcatc | aggtgactgt | gtccccagcc | cctgccacaa | tggtgggaca | 1980 |
| tgcttggagg | aggaggaagg | ggtccgctgc | ctatgtctgc | ctggctatgg | ggggacctg | 2040 |
| tgcgatgttg | gcctccgctt | ctgcaacccc | ggctgggacg | ccttccaggg | cgcctgctac | 2100 |

-continued

```
aagcactttt ccacacgaag gagctgggag gaggcagaga cccagtgccg gatgtacggc    2160
gcgcatctgg ccagcatcag cacacccgag gaacaggact tcatcaacaa ccggtaccgg    2220
gagtaccagt ggatcggact caacgacagg accatcgaag gcgacttctt gtggtcggat    2280
ggcgtccccc tgctctatga gaactggaac cctgggcagc ctgacagcta cttcctgtct    2340
ggagagaact gcgtggtcat ggtgtggcat gatcagggac aatggagtga cgtgccctgc    2400
aactaccacc tgtcctacac ctgcaagatg gggctggtgt cctgtgggcc gccaccggag    2460
ctgcccctgg ctcaagtgtt cggccgccca cggctgcgct atgaggtgga cactgtgctt    2520
cgctaccggt gccgggaagg actggcccag cgcaatctgc cgctgatccg atgccaagag    2580
aacggtcgtt gggaggcccc ccagatctcc tgtgtgccca aagacctgcc ccgagctctg    2640
cacccagagg aggacccaga aggacgtcag gggaggctac tgggacgctg gaaggcgctg    2700
ttgatccccc cttccagccc catgccaggt ccctag                              2736
```

<210> SEQ ID NO 24
<211> LENGTH: 2047
<212> TYPE: DNA
<213> ORGANISM: Homo sapiens

<400> SEQUENCE: 24

```
atgaataact tgaatgtgaa accagctttc tacacatgcg tggaagtcac tgctggaaac      60
aggttatttt atcacattgt tgattcagat gaagtcagca cgaagatttt aatggagttt     120
aataaaatga atcttcctgg agaggttact tttctgcctc ttaacaagtt agatgtcagg     180
gatacagcct atcctgaaac caatgatgct attcctatga tcagcaaact gaggtacaat     240
cccagatttg acaaagcttt caaacatgtg tttggaaaga ctcttatttg tcgtagcatg     300
gaagtttcaa cccagctggc ccgtgctttc actatggact gtattacttt ggaaggtgac     360
caagtcagcc atcggggtgc tctaactggg ggttattatg acacaaggaa gtctcgactt     420
gaattgcaaa aagatgttag aaaagcagaa gaagaactag gtgaacttga agcaaagctc     480
aatgaaaacc tgcgcagaaa tattgaaagg attaataatg aaattgatca gttgatgaac     540
caaatgcaac agatcgagac ccagcaaagg aaatttaaag catctagaga tagcatatta     600
tcagaaatga gatgctaaa agagaagagg cagcagtcag agaaaacctt catgcctaag     660
caacgtagct tacagagttt ggaggcaagc ttgcatgcta tggagtctac cagagagtca     720
ttgaaagcag aactgggaac tgatttgctt tctcaactga gtttggaaga tcagaagaga     780
gtagatgcac tgaatgatga gattcgtcaa cttcagcagg aaaacagaca gttgctaaat     840
gaaagaatta aattagaagg tattattact cgagtagaga cttatctcaa tgagaatctg     900
agaaaacgct ggaccaagt agaacaggaa cttaatgagc tgagagagac agaaggggggt     960 actgttctca cagccacaac atcagaactt gaagccatca taaaagagt aaaagacact    1020 atggcacgat cagaagattt ggacaattcc attgataaaa cagaagctgg aattaaggag    1080
cttcagaaga gtatggagcg ctggaaaaat atggaaaaag aacatatgga tgctataaat    1140
catgatacta agaactgga aaagatgaca atcggcaag gcatgctatt gaagaagaaa    1200
gaagagtgta tgaagaaaat tcgagaactt ggatcacttc cccaggaagc atttgaaaag    1260
taccagacac tgagcctcaa acagttgttt cgaaaacttg agcagtgcaa cacagaatta    1320
aagaagtaca gccatgttaa caaaaggct ttggatcagt ttgtaaattt ctccgagcag    1380
aaagaaaagt taataaagcg tcaagaagag ttagataggg gttacaaatc gatcatggaa    1440
ctgatgaatg tacttgaact tcggaaatat gaagctattc agttaacttt caaacaggta    1500
```

| | |
|---|---|
| tctaagaact tcagtgaagt attccagaag ttagtacctg gtggcaaagc tactttggtg | 1560 |
| atgaagaaag gagatgtgga gggcagtcag tctcaagatg aaggagaagg gagtggtgag | 1620 |
| agtgagaggg gttctggctc acaaagcagt gtcccatcag ttgaccagtt tactggagtt | 1680 |
| ggaattaggg tgtcatttac aggaaaacaa ggtgaaatga gagaaatgca acagctttca | 1740 |
| ggtggacaga atccttggt agcccttgct ctgattttg ccattcagaa atgtgacccg | 1800 |
| gctccatttt acttgtttga tgaaattgac caggctctgg atgctcagca cagaaaggct | 1860 |
| gtgtcagata tgattatgga acttgctgta catgctcagt ttattacaac tacttttagg | 1920 |
| cctgaactgc ttgagtcagc tgacaaattc tatggtgtaa agttcagaaa taaggttagt | 1980 |
| catattgatg tgatcacagc agagatggcc aaagactttg tagaagatga taccacacat | 2040 |
| ggttaat | 2047 |

<210> SEQ ID NO 25
<211> LENGTH: 7038
<212> TYPE: DNA
<213> ORGANISM: Homo sapiens

<400> SEQUENCE: 25

| | |
|---|---|
| atgaataact ttgaatgtga accagctttc tacacatgcg tggaagtcac tgctggaaac | 60 |
| aggttatttt atcacattgt tgattcagat gaagtcagca cgaagatttt aatggagttt | 120 |
| aataaaatga atcttcctgg agaggttact tttctgcctc ttaacaagtt agatgtcagg | 180 |
| gatacagcct atcctgaaac caatgatgct attcctatga tcagcaaact gaggtacaat | 240 |
| cccagatttg acaaagcttt caaacatgtg tttggaaaga ctcttatttg tcgtagcatg | 300 |
| gaagtttcaa cccagctggc ccgtgctttc actatggact gtattacttt ggaaggtgac | 360 |
| caagtcagcc atcggggtgc tctaactggg ggttattatg acacaaggaa gtctcgactt | 420 |
| gaattgcaaa aagatgttag aaaagcagaa gaagaactag tgaacttga agcaaagctc | 480 |
| aatgaaaacc tgcgcagaaa tattgaaagg attaataatg aaattgatca gttgatgaac | 540 |
| caaatgcaac agatcgagac ccagcaaagg aaatttaaag catctagaga tagcatatta | 600 |
| tcagaaatga gatgctaaa agagaagagg cagcagtcag agaaaacctt catgcctaag | 660 |
| caacgtagct acagagtttt ggaggcaagc ttgcatgcta tggagtctac cagagagtca | 720 |
| ttgaaagcag aactgggaac tgatttgctt tctcaactga gtttggaaga tcagaagaga | 780 |
| gtagatgcac tgaatgatga gattcgtcaa cttcagcagg aaaacagaca gttgctaaat | 840 |
| gaaagaatta aattagaagg tattattact cgagtagaga cttatctcaa tgagaatctg | 900 |
| atggccggcc ggtcccaccc gggcccgctg cggccgctgc tgccgctcct tgtggtggcc | 960 |
| gcgtgcgtcc tgcccggagc cggcgggaca tgcccggagc gcgcgctgga gcggcgcgag | 1020 |
| gaggaggcga acgtggtgct caccgggacg gtggaggaga tcctcaacgt ggacccggtg | 1080 |
| cagcacacgt actcctgcaa ggttcgggtc tggcggtact tgaagggcaa agacctggtg | 1140 |
| gcccgggaga gcctgctgga cggcggcaac aaggtggtga tcagcggctt tggagacccc | 1200 |
| ctcatctgtg acaaccaggt gtccactggg gacaccagga tcttctttgt gaaccctgca | 1260 |
| cccccatacc tgtggccagc ccacaagaac gagctgatgc tcaactccag cctcatgcgg | 1320 |
| atcaccctgc ggaacctgga ggaggtggag ttctgtgtgg aagataaacc cgggacccac | 1380 |
| ttcactccag tgcctccgac gcctcctgat gcgtgccggg gaatgctgtg cggcttcggc | 1440 |
| gccgtgtgcg agcccaacgc ggaggggccg ggccgggcgt cctgcgtctg caagaagagc | 1500 |

```
ccgtgcccca gcgtggtggc gcctgtgtgt gggtcggacg cctccaccta cagcaacgaa    1560
tgcgagctgc agcgggcgca gtgcagccag cagcgccgca tccgcctgct cagccgcggg    1620
ccgtgcggct cgcgggaccc ctgctccaac gtgacctgca gcttcggcag cacctgtgcg    1680
cgctcggccg acgggctgac ggcctcgtgc ctgtgccccg cgacctgccg tggcgccccc    1740
gaggggaccg tctgcggcag cgacggcgcc gactacccccg gcgagtgcca gctcctgcgc    1800
cgcgcctgcg cccgccagga gaatgtcttc aagaagttcg acggcccttg tgaccctgt    1860 cagggcgccc tccctgaccc gagccgcagc tgccgtgtga acccgcgcac gcggcgccct    1920
gagatgctcc tacggcccga gagctgccct gcccggcagg cgccagtgtg tggggacgac    1980
ggagtcacct acgaaaacga ctgtgtcatg ggccgatcgg gggccgcccg gggtctcctc    2040
ctgcagaaag tgcgctccgg ccagtgccag ggtcgagacc agtgcccgga gcctgccgg    2100 ttcaatgccg tgtgcctgtc ccgccgtggc cgtccccgct gctcctgcga ccgcgtcacc    2160
tgtgacgggg cctacaggcc cgtgtgtgcc caggacgggc gcacgtatga cagtgattgc    2220
tggcggcagc aggctgagtg ccggcagcag cgtgccatcc ccagcaagca ccagggcccg    2280
tgtgaccagg ccccgtcccc atgcctcggg gtgcagtgtg catttggggc gacgtgtgct    2340
gtgaagaacg ggcaggcagc gtgtgaatgc ctgcaggcgt gctcgagcct ctacgatcct    2400
gtgtgcggca cgacggcgt cacatacggc agcgcgtgcg agctggaggc cacggcctgt    2460
accctcgggc gggagatcca ggtggcgcgc aaaggaccct gtgaccgctg cgggcagtgc    2520
cgctttggag ccctgtgcga ggccgagacc gggcgctgcg tgtgcccctc tgaatgcgtg    2580
gctttggccc agcccgtgtg tggctccgac gggcacacgt accccagcga gtgcatgctg    2640
cacgtgcacg cctgcacaca ccagatcagc ctgcacgtgg cctcagctgg accctgtgag    2700
acctgtggag atgccgtgtg tgcttttggg gctgtgtgct ccgcagggca gtgtgtgtgt    2760
ccccggtgtg agcacccccc gcccggcccc gtgtgtggca cgacggtgt cacctacggc    2820 agtgcctgcg agctacggga agccgcctgc ctccagcaga cacagatcga ggaggcccgg    2880
gcagggccgt gcgagcaggc cgagtgcggt tccggaggct ctggctctgg ggaggacggt    2940
gactgtgagc aggagctgtg ccggcagcgc ggtggcatct gggacgagga ctcggaggac    3000
gggccgtgtg tctgtgactt cagctgccag agtgtcccag gcagcccggt gtgcggctca    3060 gatgggtca cctacagcac cgagtgtgag ctgaagaagg ccaggtgtga gtcacagcga    3120
gggctctacg tagcgcccca gggagcctgc cgaggcccca ccttcgcccc gctgccgcct    3180 gtggcccct tacactgtgc ccagacgccc tacggctgct gccaggacaa tatcaccgca    3240
gcccggggcg tgggcctggc tggctgcccc agtgcctgcc agtgcaaccc ccatggctct    3300 tacgcggca cctgtgaccc agccacaggc cagtgctcct gccgcccagg tgtgggggc    3360 ctcaggtgtg accgctgtga gcctggcttc tggaacttc gaggcatcgt caccgatggc    3420
cggagtggct gtacaccctg cagctgtgat ccccaaggcg ccgtgcggga tgactgtgag    3480
cagatgacgg ggctgtgctc gtgtaagccc ggggtggctg gacccaagtg tgggcagtgt    3540
ccagacggcc gtgccctggg ccccgcggc tgtgaagctg acgcttctgc gcctgcgacc    3600
tgtgcggaga tgcgctgtga gttcggtgcg cggtgcgtgg aggagtctgg ctcagcccac    3660
tgtgtctgcc cgatgctcac ctgtccagag gccaacgcta ccaaggtctg tgggtcagat    3720
ggagtcacat acggcaacga gtgtcagctg aagaccatcg cctgccgcca gggcctgcaa    3780
atctctatcc agagcctggg cccgtgccag gaggctgttg ctcccagcac tcacccgaca    3840
tctgcctccg tgactgtgac cacccccaggg ctcctcctga gccaggcact gccggccccc    3900
```

-continued

```
cccggcgccc tccccctggc tcccagcagt accgcacaca gccagaccac ccctccgccc    3960
tcatcacgac ctcggaccac tgccagcgtc cccaggacca ccgtgtggcc cgtgctgacg    4020
gtgcccccca cggcaccctc ccctgcaccc agcctggtgg cgtccgcctt tggtgaatct    4080
ggcagcactg atggaagcag cgatgaggaa ctgagcgggg accaggaggc cagtgggggt    4140
ggctctgggg ggctcgagcc cttggagggc agcagcgtgg ccaccctgg gccacctgtc     4200
gagagggctt cctgctacaa ctccgcgttg ggctgctgct ctgatgggaa gacgccctcg    4260
ctggacgcag agggctccaa ctgccccgcc accaaggtgt tccagggcgt cctggagctg    4320
gagggcgtcg agggccagga gctgttctac acgcccgaga tggctgaccc caagtcagaa    4380
ctgttcgggg agacagccag gagcattgag agcaccctgg acgacctctt ccggaattca    4440
gacgtcaaga aggattttcg gagtgtccgc ttgcgggacc tggggcccgg caaatccgtc    4500
cgcgccattg tggatgtgca ctttgacccc accacagcct tcaggcacc cgacgtggcc     4560
cgggccctgc tccggcagat ccaggtgtcc aggcgccggt ccttgggggt gaggcggccg    4620
ctgcaggagc acgtgcgatt tatgactttt gactggtttc ctgcgtttat cacgggggcc    4680
acgtcaggag ccattgctgc gggagccacg gccagagcca ccactgcatc gcgcctgccg    4740
tcctctgctg tgacccctcg ggccccgcac cccagtcaca caagccagcc cgttgccaag    4800
accacggcag cccccaccac acgtcggccc cccaccactg cccccagccg tgtgcccgga    4860
cgtcggcccc cggcccccca gcagcctcca aagccctgtg actcacagcc ctgcttccac    4920
gggggggacct gccaggactg ggcattgggc ggggcttca cctgcagctg cccggcaggc    4980
aggggaggcg ccgtctgtga aaggtgctt ggcgcccctg tgccggcctt cgagggccgc    5040
tccttcctgg ccttccccac tctccgcgcc taccacacgc tgcgcctggc actggaattc    5100
cgggcgctgg agcctcaggg gctgctgctg tacaatggca acgcccgggg caaggacttc    5160
ctggcattgg cgctgctaga tggccgcgtg cagctcaggt ttgacacagg ttcggggccg    5220
gcggtgctga ccagtgccgt gccggtagag ccgggccagt ggcaccgcct ggagctgtcc    5280
cggcactggc gccggggcac cctctcggtg gatggtgaga cccctgttct gggcgagagt    5340
cccagtggca ccgacggcct caacctggac acagacctct tgtgggcgg cgtacccgag    5400
gaccaggctg ccgtggcgct ggagcggacc ttcgtgggcg ccggcctgag ggggtgcatc    5460
cgtttgctgg acgtcaacaa ccagcgcctg gagcttggca ttgggccggg ggctgccacc    5520
cgaggctctg gcgtgggcga gtgcgggac caccctgcc tgcccaaccc ctgccatggc     5580
ggggcccat gccagaacct ggaggctgga aggttccatt gccagtgccc gcccggccgc    5640
gtcggaccaa cctgtgccga tgagaagagc ccctgccagc ccaaccctg ccatgggcg     5700
gcgccctgcc gtgtgctgcc cgagggtggt gctcagtgcg agtgccccct ggggcgtgag    5760
ggcaccttct gccagacagc ctcggggcag gacggtctg gcccttcct ggctgacttc     5820
aacggcttct cccacctgga gctgagaggc ctgcacacct ttgcacggga cctggggag     5880
aagatggcgc tggaggtcgt gttcctggca cgaggcccca gcggcctcct gctctacaac    5940
gggcagaaga cggacggcaa gggggacttc gtgtcgctgg cactgcggga ccgccgcctg    6000
gagttccgct acgacctggg caaggggca gcggtcatca ggagcaggga gccagtcacc     6060
ctgggagcct ggaccagggt ctcactggag cgaaacggcc gcaagggtgc cctgcgtgtg    6120
ggcgacggcc ccgtgtgttt gggggagtcc ccggttccgc acaccgtcct caacctgaag    6180
gagccgctct acgtaggggg cgctcccgac ttcagcaagc tggcccgtgc tgctgccgtg    6240
```

```
tcctctggct tcgacggtgc catccagctg gtctccctcg gaggccgcca gctgctgacc    6300
ccggagcacg tgctgcggca ggtggacgtc acgtcctttg caggtcaccc ctgcacccgg    6360
gcctcaggcc acccctgcct caatgggggcc tcctgcgtcc cgagggaggc tgcctatgtg    6420
tgcctgtgtc ccgggggatt ctcaggaccg cactgcgaga aggggctggt ggagaagtca    6480 gcggggacg tggatacctt ggcctttgac gggcggacct ttgtcgagta cctcaacgct    6540
gtgaccgaga gcgagaaggc actgcagagc aaccactttg aactgagcct gcgcactgag    6600
gccacgcagg ggctggtgct ctggagtggc aaggccacgg agcgggcaga ctatgtggca    6660
ctggccattg tggacgggca cctgcaactg agctacaacc tgggctccca gcccgtggtg    6720
ctgcgttcca ccgtgcccgt caacaccaac cgctggttgc gggtcgtggc acatagggag    6780
cagagggaag gttccctgca ggtgggcaat gaggcccctg tgaccggctc ctccccgctg    6840
ggcgccacgc agctggacac tgatggagcc ctgtggcttg ggggcctgcc ggagctgccc    6900
gtgggcccag cactgcccaa ggcctacggc acaggctttg tgggctgctt gcgggacgtg    6960
gtggtgggcc ggcacccgct gcacctgctg gaggacgccg tcaccaagcc agagctgcgg    7020
ccctgcccca ccccatga                                                 7038

<210> SEQ ID NO 26
<211> LENGTH: 477
<212> TYPE: DNA
<213> ORGANISM: Homo sapiens

<400> SEQUENCE: 26
atgatgcaga agctactcaa atgcagtcgg cttgtcctgg ctcttgccct catcctggtt      60
ctggaatcct cagttcaagg ttatcctacg cggagagcca ggtaccaatg ggtgcgctgc     120
aatccagaca gtaattctgc aaactgcctt gaagaaaaag gaccaatgtt cgaactactt     180
ccaggtgaat ccaacaagat cccccgtctg aggactgacc tttttccaaa gacgagaatc     240
caggacttga atcgtatctt cccactttct gaggactact ctggatcagg cttcggctcc     300
ggctccggct ctggatcagg atctgggagt ggcttcctaa cggaaatgga acaggattac     360
caactagtag acgaaagtga tgctttccat gacaacctta ggtctcttga caggaatctg     420
ccctcagaca gccaggactt gggtcaacat ggattagaag aggattttat gttataa       477

<210> SEQ ID NO 27
<211> LENGTH: 45
<212> TYPE: DNA
<213> ORGANISM: Homo sapiens

<400> SEQUENCE: 27
atggggtggc gggcgccggg cgcgctgctg ctggcgctgc tgctg                     45
```

WOUND AND CUTANEOUS INJURY HEALING WITH A NUCLEIC ACID ENCODING A PROTEOGLYCAN POLYPEPTIDE

CROSS-REFERENCE TO RELATED APPLICATIONS

This is a continuation-in-part of U.S. patent application Ser. No. 11/604,633, filed Nov. 27, 2006, now U.S. Pat. No. 7,488,719, issued Feb. 20, 2009, which is a continuation of U.S. patent application Ser. No. 10/420,270, filed Apr. 22, 2003, now U.S. Pat. No. 7,141,551, issued Nov. 28, 2006, which claims benefit of U.S. Provisional Patent Application No. 60/374,553, filed Apr. 22, 2002.

FIELD OF THE DISCLOSURE

The present disclosure relates to biomolecules involved in wound healing and repair and methods of using and delivering such biomolecules in would healing and repair.

BACKGROUND

Proteoglycans are molecules that contain both a protein portion (which may be referred to as the protein core) and glycosaminoglycan portion. Glycosaminoglycans are the most widely present polysaccharides in the animal kingdom and are mainly found in the connective tissues. Glycosaminoglycans are biological polymers made up of linear disaccharide units containing an uronic acid and a hexosamine and are attached to the core proteins via a linking tetrasaccharide moiety. The major glycosaminoglycans are hyaluronic acid, chondroitin sulfates, heparan sulfate, dermatan sulfate and keratan sulfate.

Physiochemical properties such as, but not limited to, solvation and interaction with biological tissues and structures are related to, at least in part, the presence of carboxylic acid and/or sulfuric groups within the glycosaminoglycan chains. The glycosaminoglycan chains can impart a substantial negative charge to the proteoglycan proteins. The aligned sulfated glycosaminoglycans chains can sequester water through hydrogen bonding, holding many times their weight in water. Such properties determine, in part, the biological activity of the glycosaminoglycans in extracellular matrices. Glycosaminoglycans also help to maintain a favorable environment for cell growth. Because of these characteristics, glycosaminoglycans are used in many clinical and medical applications. The use of glycosaminoglycans in cosmetics is also due to their physicochemical and biological properties linked to their molecular weight and their water retaining capacity (Gagnieu, et al., Peau Seche et Hydratation, Lyon, France, Journees Internationales de Dermocosmetologie de Lyon, 1998). The hydrating potential of recombinantly expressed proteoglycans has also been published (Huc, et al., Peau Seche et Hydration, Lyon, France, 1988).

Proteins that are membrane bound become either integral membrane proteins, with a transmembrane domain, or glycosylphosphotidylinositol (GPI) linked to the lipid bilayer. Within an integral membrane protein, a transmembrane helix is a segment that is alpha-helical in structure, roughly 20 amino acids in length, and is said to "span" the membrane.

Glycosaminoglycan chains are synthesized via similar routes involving the stepwise addition of four monosaccharides to serine residues followed by co-polymerization of disaccharide units. It has been shown that serine followed by glycine residues are heavily favored acceptors for xylosyltransferase, the key enzyme in the initial step of glycosaminoglycan glycosylation. The priming of glycosaminoglycan synthesis as well as determining the type of glycosylation is in part encoded by the core protein. The formation of heparan sulfate over chondroitin sulfate, for example, is favored when the core protein contains 2 or more serine-glycine (SG)-consensus sequences in close proximity to each other, a cluster of acidic amino acids is located nearby, and a tryptophan residue immediately follows the (SG) glycosaminoglycan attachment sites. However, acidic clusters are also found in chondroitin sulfate proteoglycans and thus seem to be necessary but not sufficient for the priming of heparan sulfate glycosylation. Therefore, while the sites for glycosaminoglycan attachment are known to some extent, the rules governing the type and extent of glycosaminoglycan modification are still not clear. The GAG attachment sites are known for a number of proteoglycans, including perlecan (Dolan et al, J. Biol. Chem., Vol. 272, p. 4316-4322, 1997), collagen XVIII (Dong et al., J. Biol. Chem., Vol. 278, p. 1700-1707, 2003), syndecan-1 (Zhang et al., J. Biol. Chem., Vol. 270, p. 27127-27135, 1995), glypican (Chen et al., J. Biol. Chem., Vol. 276, p. 7507-7517, 2001) and agrin (Winzen et al., J. Biol. Chem., Vol. 278, p. 30106-30114, 2003).

Chronic sun exposure induces numerous changes in exposed skin; the most striking histopathologic change is the massive accumulation of material with the staining characteristics of elastin, termed solar elastosis, in the superficial dermis. Recently, the large chondroitin sulfate proteoglycan, versican, has been identified in the dermis in association with elastic fibers, and the smaller chondroitin sulfate proteoglycan, decorin, has been shown to codistribute with collagen fibers. Evidence was published for the close association of versican with elastic fibers and decorin with collagen fibers, even in the situation of abnormal fiber deposition occurring in photodamaged skin (Bernstein, et al., *Lab Invest* 72(6): 662-9, 1995). In addition, changes in versican and decorin immunostaining were accompanied by similar alterations in gene expression. In another study, the effect of UVB exposure on the distribution and synthesis of dermal proteoglycans was measured in the skin of mice (Margelin, et al., *Photochem Photobiol* 58(2): 211-8, 1993). The results demonstrated that chronic doses of UVB altered proteoglycan metabolism through both quantitative and qualitative changes.

Numerous articles have been published about the necessity of moisturizers for patients with dermatological damage, such as dryness caused by rosacea, and the ability of moisturizers to hydrate the skin and reduce transepidermal water loss (TEWL), further improving the vigor of the stratum corneum (Draelos, *Dermatol Clin* 18(4): 597-607, 2000; Bikowski, *Cutis* 68(5 Suppl): 3-11, 2001; Rawlings, et al., *Dermatol Ther* 17 Suppl 1: 49-56, 2004; Draelos, *Cutis* 76(6 Suppl): 19-25, 2005). Such moisturizers may contain proteoglycans. Although these moisturizers have been shown to improve patient skin health and appearance, they are presently only delivered as pre-synthesized proteoglycans and so limited in their effectiveness.

Despite the widespread use and acceptance of proteoglycans and glycosaminoglycans in pharmaceuticals, the use of proteoglycans when delivered as polynucleotides has only been described for the proteoglycans decorin and biglycan in the scientific literature, and for decorin (U.S. Pat. No. 6,524, 573) and perlecan (U.S. Pat. No. 7,141,551) in the patent literature. In addition, a patent has been issued describing in-situ delivery of nucleic acid encoding syndecan intracellular sequences as a fusion transmembrane protein that is expressed as a cell-bound molecule (U.S. Pat. No. 7,029, 668). This is substantially different in scope and meaning from the present disclosure, which discloses a polynucleotide encoding a secreted proteoglycan. In managing skin homeostasis, secreting the proteoglycan into the extracellular matrix is an important aspect of the present invention and has not been demonstrated as obvious to experts in the field.

Due to their propensity to sequester water, the delivery of proteoglycan polypeptides to the sites of wounds or cutaneous injury caused by age, sun exposure, skin ailments, or trauma will visibly reduce wrinkling or surface irregularities as the sequestered water hydrates the area and cause conditions favorable for treatment and/or prevention of wounds and/or cutaneous injury. In addition, more highly hydrated skin should function better, possibly allowing for increased blood flow and elasticity, further improving appearance, and increasing patient health by allowing nutrients to be distributed more readily.

The present disclosure provides nucleic acid constructs encoding one or more polypeptides containing one or more sites for glycation by glycosaminoglycan chain, such as proteoglycan polypeptides, and methods for delivering to the site of a wound or cutaneous injury at least one nucleic acid construct encoding one or more such polypeptides, such that the expressed polypeptide is decorated by glycosaminoglycan chains through the normal physiological processes of the subject at the site of administration to produce a polypeptide for the healing of the wound or other cutaneous injury. The delivered nucleic acid construct is transcribed, translated to produce a polypeptide, which is subsequently post-translationally modified by the addition of glycosaminoglycan chains (referred herein as "decoration" or "glycation") to produce a polypeptide. The glycated polypeptide is then secreted from the cell in which it was produced as directed by a sequence that is sufficient for secretion. During the secretion process, all or a portion of such sequence may be cleaved. After secretion, the glycated polypeptide is available to provide treatment of wounds and/or cutaneous injury in the subject and/or prevention of cutaneous injury in a subject. As a result, the glycated polypeptide released is decorated optimally by the normal physiological process of the subject to provide one or more glycosaminoglycan containing polypeptides based on the conditions prevailing at the site of administration in a particular subject. In a particular embodiment, the glycosaminoglycan containing polypeptide is a proteoglycan polypeptide.

BRIEF DESCRIPTION OF DRAWINGS

FIG. 1A shows a 96-well dot-blot of 100 µl of the solubilized residual cell matrix samples and 100 µl of the conditioned medium (presented as duplicate samples). Immunoreactivity was assessed using the anti-D1 mAb A71. Columns 1 and 2 are solubilized residual cell matrix from primary human endothelial cells cultures following 9 days of culture after infection with perlecanD1-Ad and control RevD1-Ad, respectively. Columns 3 and 4 are conditioned medium from primary human endothelial cells cultures following removed following 5 days of culture after infection with perlecanD1-Ad and control RevD1-Ad, respectively. Columns 5 and 6 are conditioned medium from primary human endothelial cells cultures removed following 6-9 days of culture after infection with perlecanD1-Ad and control RevD1-Ad, respectively.

FIG. 1B shows a 96-well dot-blot of 100 µl of the solubilized residual cell matrix samples and 100 µl of the conditioned medium (presented as duplicate samples). Immunoreactivity was assessed using the anti-D5 mAb A74. Columns 1 and 2 are solubilized residual cell matrix from primary human endothelial cells cultures following 9 days of culture after infection with perlecanD1-Ad and control RevD1-Ad, respectively. Columns 3 and 4 are conditioned medium from primary human endothelial cells cultures following removed following 5 days of culture after infection with perlecanD1-Ad and control RevD1-Ad, respectively. Columns 5 and 6 are conditioned medium from primary human endothelial cells cultures following removed following 6-9 days of culture after infection with perlecanD1-Ad and control RevD1-Ad, respectively.

DETAILED DESCRIPTION

Figure 1A:
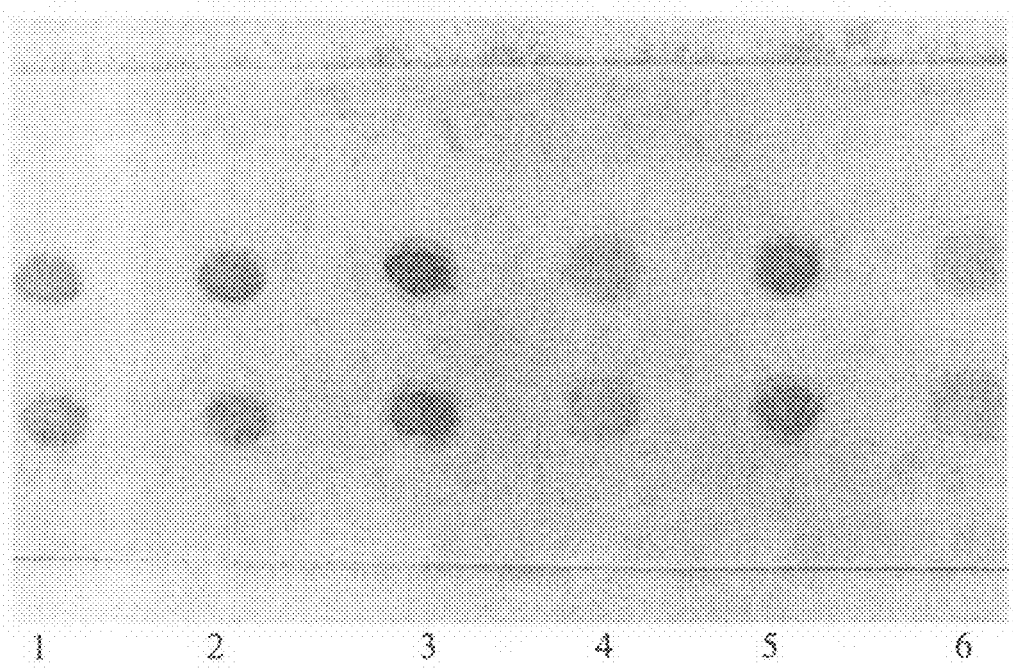
FIGS. 1A and 1B demonstrate that proteoglycan polypeptides comprising a signal sequence are secreted from fibroblast and endothelial cells.

The present disclosure provides nucleic acid encoding a proteoglycan polypeptide and methods for delivering to the site of a wound or cutaneous injury at least one nucleic acid encoding a proteoglycan polypeptide, such that the expressed polypeptide is decorated by glycosaminoglycan chains through the normal physiological processes of the subject at the site of administration to produce a functional glycated polypeptide for the healing of the wound or other cutaneous injury. In one embodiment, at least one of the one or more polypeptides is a proteoglycan polypeptide. Furthermore, in one embodiment, such nucleic acid construct may further comprise a sequence sufficient for excretion as described below. The delivered nucleic acid construct is transcribed, translated and post-translationally modified by the addition of glycosaminoglycan chains (referred herein as "decoration" or "glycation") to produce a glycated polypeptide. The glycated polypeptide is then secreted from the cell in which it was produced as directed by a sequence that is sufficient for secretion. During the secretion process, all or a portion of such sequence may be cleaved. After secretion, the glycated polypeptide is available to provide treatment and/or prevention of wounds and/or cutaneous injury. As a result, the polypeptide released is glycated optimally by the normal physiological process of the subject to provide one or more glycosaminoglycan containing polypeptide molecules based on the conditions prevailing at the site of administration in a particular subject.

Approximately 30 proteoglycan polypeptides have been identified with sizes ranging from 10 to >500 kDa and the number of attached glycosaminoglycan chains ranging from 1 to >100. Exemplary proteoglycans are discussed in more detail below. Aggrecan is a large core protein decorated with numerous chondroitin sulfate and keratan sulfate chains (>100) and will likely sequester the most water per molecule of the discussed proteoglycans. Aggrecan is also known to interact with hyaluronic acid in cartilage, providing for the high water content in joints and increasing the osmotic swelling in the joint. The core protein is 225 kDa with 2162 amino acids. After addition of the 130 to more than 200 carbohydrate chains, the molecular weight is considerably higher with highly charged, hydrophilic moieties that could conceivably hold up to 75% of its weight in water. The keratan sulfate chains are generally localized to the N-terminus while the chondroitin sulfate chains are located more in the C-terminus section. Fragments of the aggrecan proteoglycan protein may be advantageously used since their production would be less energetically costly to produce and would still provide the beneficial physiochemical properties without the need for the full length protein.

Versican is a large proteoglycan of about 265 KDa with 12-15 chondroitin sulfate chains attached. This protein is a major component of the dermal layer of skin, and interacts with hyaluronan in the extracellular matrix through N-terminal contacts. Versican also interacts with numerous other signaling molecules through C-terminal contacts. The central domain of versican contains the glycosaminoglycan attachment points, but differential splicing in various tissues leads to a variety of glycosaninoglycan attachments and sulfation patterns, further yielding an assortment of glycosaminoglycan chain interactions with other molecules. In addition, since versican is known to interact with hyaluronan, increased versican production may increase hyaluronan production.

In addition to versican, dermis contains several small leucine-rich proteoglycans (SLRPs) such as decorin, biglycan and lumican. SLRPs seem to play an important role in the regulation of cell activity and in the organization and functional properties of skin connective tissue. A modification of their repartition might be involved in the alterations which occur in skin aging. It was shown that lumican expression decreased during aging whereas decorin expression tended to increase, resulting in a strong alteration of the decorin to lumican ratio. On the other hand, biglycan expression was not modified during aging. Alterations of SLRPs expression could be implicated in the functional impairment which affect aged skin (Vuillermoz, et al., *Mol Cell Biochem* 277(1-2): 63-72, 2005).

Lumican has a 38 KDa protein core that contains two keratan sulfate GAG attachment sites, and has been shown to affect the integrity of the extracellular matrix and skin structure. For instance, knockout mice that could not express lumican displayed abnormal collagen assembly and brittle skin, suggesting lumican plays a large role in ECM maintenance and in skin health (Wegrowski et al., *Mol Cell Biochem* 205 (1-2): 125-31, 2000; Vuillermoz, et al., *Mol Cell Biochem* 277(1-2): 63-72, 2005). Periodontal health is also affected by lumican removal due to its interactions with collagen (Matheson, et al., *J Periodontal Res* 40(4): 312-24, 2005). In addition, Roughley et. al. indicated a role for lumican and other SLRPs in protecting collagen from degradation by collagenases, further suggesting a role for lumican in ECM maintenance and prevention of ECM degradation (Geng, et al., *Matrix Biol.*, 25(8):484-91 2006). Further, Vuillermoz et. al. showed that lumican expression decreased in skin fibroblasts with increased age, suggesting a possible role of lumican in age-related damage to skin. In addition, several studies have suggested that lumican plays a role in corneal health, as decreased or knocked-out lumican expression resulted in poor corneal formation (Chakravarti, *Glycoconj J* 19(4-5): 287-93, 2002), further supporting a role in collagen fibril formation, but, also, purified lumican has been shown to promote corneal epithelial wound healing (Yeh, et al. *Opthalmol Vis Sci* 46(2): 479-86, 2005). Therefore, it is likely that delivery of lumican encoding nucleic acids to skin as described in the present disclosure would facilitate collagen fibril formation and increase the water content due to the charge and hydrophilicity of the glycosaminoglycan chains, thereby increasing skin health and appearance. Other known proteoglycans include syndecans 1-4, glypicans 1-5, betaglycan, NG2/CSPG4, CD44/epican, fibromodulin, PRELP, keratocan, osteoadherin/osteomodulin, epiphycan, osteoglycin/mimecan, neurocan/CSPG3, brevican, bamacan, agrin, and serglycin.

In a first embodiment, the present disclosure provides an isolated nucleic acid molecule encoding one or more proteoglycan polypeptides. Such isolated nucleic acid molecule may be a part of a suitable vector for expression in a target cell of a subject. Alternatively, the isolated nucleic acid molecules may be delivered as naked nucleic acid.

In a second embodiment, the present disclosure provides for a composition comprising one or more of the nucleic acids of the first embodiment.

In a third embodiment, the present disclosure provides for a composition consisting essentially of one or more of the nucleic acids of the first embodiment.

In a fourth embodiment, the present disclosure provides for a composition consisting of one or more of the nucleic acids of the first embodiment.

The compositions, of the second through fourth embodiments may be pharmaceutical compositions and may further contain a pharmaceutically acceptable carrier and/or accessory agents. Such compositions may be used in the treatment and prevention methods of the fifth and sixth embodiments.

In a fifth embodiment, the present disclosure describes a method for the effective treatment of a wound or a cutaneous injury in a subject in need of such treatment by administering to a site of the wound or cutaneous injury a composition of the present disclosure, such as, but not limited to, the compositions described in the second through fourth embodiments above. Such administration to the site may be achieved by local administration or systemic administration. The at least one nucleic acid molecule encoding one or more proteoglycan polypeptides may be delivered using a vector or as naked nucleic acid, or other methods as are known in the art. In such treatment methods encompassed by the fifth embodiment, the composition is administered so as to deliver a therapeutically effective amount of the nucleic acid encoding one or more proteoglycan polypeptides to treat the wound or cutaneous injury.

In a sixth embodiment, the present disclosure describes a method for the effective prevention of a cutaneous injury in a subject in need of such prevention by the administering to a site where it is desired to prevent such cutaneous injury a composition of the present disclosure, such as, but not limited to, the compositions described in the second through fourth embodiments above. Such administration to the site may be achieved by local administration or systemic administration. The at least one nucleic acid molecule encoding one or more proteoglycan polypeptides may be delivered using a vector or as naked nucleic acid, or other methods as are known in the art. In such prevention methods encompassed by the sixth embodiment, the composition is administered so as to deliver a therapeutically effective amount of the nucleic acid encoding one or more proteoglycan polypeptides to prevent the cutaneous injury.

In the treatment and prevention methods of the fifth and sixth embodiments, the delivery of the at least one isolated nucleic acid molecule encoding one or more proteoglycan polypeptides allows the normal physiological processes of the subject at the site of administration to decorate the proteoglycan polypeptides with the appropriate glycosaminoglycan chains and release the glycated proteoglycan polypeptides from the cell. Because the glycation of the proteoglycan polypeptide with glycosaminoglycan elements proceeds in a differential manner depending on the site of the wound or cutaneous injury and/or the physiological environment at a particular site (which may change over time as a result of different environmental stressors, physiological process occurring at the site and/or the nature of the wound or cutaneous injury), the nature of the fully decorated proteoglycan molecule may change over time. The treatment and prevention methods of the fifth and sixth embodiments allows for the optimal glycosaminoglycan modification (i.e., glycation) to occur, resulting in one or more glycosaminoglycans with variations, such as, but not limited to, the extent of sulfation and the chain length of the glycosaminoglycan elements, that are optimal based on the conditions prevailing at the site of administration in a particular subject. Therefore, the specific nature of the expressed proteoglycan polypeptide is dictated by the normal physiological process of the subject at a particular time in response to a particular need (such as, but not limited to, wound healing or cutaneous injury).

Therefore, those methods of the prior art that apply a pre-manufactured proteoglycan molecule to the site of a wound or cutaneous injury may produce no or unsatisfactory results. Furthermore, delivery of the fully decorated proteoglycan molecules through the layers of the skin is difficult due to the size and charged nature of the proteoglycan molecules. Also, the likelihood of nucleic acid expression in the deeper layers of the skin has been demonstrated, which is a significant improvement upon the penetration of pre-synthesized, exogenous proteoglycans applied to the skin in current cosmetic formulations.

In addition, using the treatment and prevention methods of the fifth and sixth embodiments, the delivery of at least one nucleic acid molecule encoding one or more proteoglycan polypeptides provides for an extended production of decorated proteoglycan molecules as described above as the delivered nucleic acid molecules will have a particular half-life in the subject. Another important aspect of the present disclosure, that is also a significant difference and improvement upon the current state of the art, lies in the fact that delivery of recombinant nucleic acid encoding proteoglycans for treatment and prevention of wounds and cutaneous injury will result in extended production of the recombinant proteoglycan polypeptide for several days, until expression dwindles and another application of the invention would be required for further expression.

When using the compositions and/or methods of the first through sixth embodiments, a number of advantages are obtained. As discussed above, the methods of the present disclosure provide for the delivery of at least one nucleic acid molecule encoding one or more proteoglycan polypeptides, thereby allowing the normal physiological processes of the subject at the site of administration to glycate the expressed proteoglycan polypeptides with the appropriate glycosaminoglycan chains and release the decorated proteoglycan polypeptides from the cell. Therefore, the proteoglycan polypeptide released is synthesized by the normal physiological process of the subject to provide one or more proteoglycan polypeptides that are optimal based on the conditions prevailing at the site of administration in a particular subject. Such an application is not possible when administering pre-synthesized proteoglycan molecules. Furthermore, as the features of the proteoglycan core molecules that dictate the number and nature of glycosaminoglycan molecules are not completely understood, modification of a particular pre-synthesized proteoglycan molecule for a particular physiological requirement is not possible given the state of the art.

In addition, the delivery of at least one nucleic acid molecule encoding one or more proteoglycan polypeptides by the methods disclosed allows the ultimately produced proteoglycan molecules to be produced in a wider number of cell types. The methods of the present disclosure allow the proteoglycan polypeptides to be expressed at virtually any desired location.

Furthermore, using the methods of the present disclosure, an extended production of the desired proteoglycan molecules is realized since the at least one nucleic acid molecule encoding a proteoglycan polypeptide will allow for production of multiple proteoglycan polypeptides over time. Such advantages are impossible to realize using pre-synthesized proteoglycan molecules.

Definitions

As used herein, the terms "prevent", "preventing", "prevention", "suppress", "suppressing" and suppression as used herein refer to administering a nucleic acid or composition of the present disclosure prior to the onset of cutaneous injury so as to prevent any symptom, aspect or characteristic of the cutaneous injury. Such preventing and suppressing need not be absolute to be useful.

As used herein, the terms "treat", "treating" and treatment as used herein refers to administering a nucleic acid or composition of the present disclosure after the onset of cutaneous injury or appearance of a wound so as to reduce or eliminate any symptom, aspect or characteristic of the cutaneous injury or condition associated with the wound. In one embodiment, the treatment provides healing of the wound or cutaneous injury. Such treating need not be absolute to be useful.

As used herein, the term "in need of treatment" as used herein refers to a judgment made by a caregiver that a patient requires or will benefit from treatment. This judgment is made based on a variety of factors that are in the realm of a caregiver's expertise.

As used herein, the term "in need of prevention" as used herein refers to a judgment made by a caregiver that a patient requires or will benefit from prevention. This judgment is made based on a variety of factors that are in the realm of a caregiver's expertise.

As used herein, the terms "subject", "individual" or "patient" as used herein refers to any animal, including mammals, such as, but not limited to, mice, rats, other rodents, rabbits, dogs, cats, swine, cattle, sheep, horses, or primates, or humans. The term may specify male or female or both, or exclude male or female.

As used herein, the term "therapeutically effective amount", in reference to the treating, preventing or suppressing of a disease state/condition, refers to an amount of a compound either alone or as contained in a pharmaceutical composition that is capable of having any detectable, positive effect on any symptom, aspect, or characteristics of the disease state/condition. Such effect need not be absolute to be beneficial.

As used herein, the term "glycosaminoglycan" is meant to be broadly defined and includes known and, as yet, unknown glycosaminoglycans; exemplary glycosaminoglycans include, but are not limited to, hyaluronic acid, chondroitin sulfates, heparan sulfate, dermatan sulfate and keratan sulfate.

As used herein, the term "vector" means any mechanism for the transfer of a nucleic acid into a host cell of a subject. The term vector includes both viral and non-viral mechanisms for introducing the nucleic acid into a cell of a subject in vitro, ex vivo, or in vivo. Non-viral vectors include but are not limited to plasmids, liposomes, electrically charged lipids (such as cytofectins), DNA-protein complexes, and biopolymers. Viral vectors include but are not limited to vectors derived from adenoviral vectors, retroviral vectors, lentiviral vectors, bovine papilloma viruses, Epstein-Barr virus, adenoassociated, viruses, pox viruses, baculovirus, vaccinia virus, herpes simplex virus, and hybrids of two or more viral vector types. A vector may contain regulatory sequences required for expression of the nucleic acid encoding at least one proteoglycan polypeptide, such as, but not limited to, promoters and the like. The regulatory sequences may be optimized based on a particular cell type or tissue. In addition, a vector may contain one or more regulatory regions, and/or selectable markers useful in selecting, measuring, and monitoring nucleic acid transfer results (transfer to which cells, duration of expression, etc.).

As used herein, the term "secreted" or "secretion" refers to the release, export or excretion of a polypeptide from a cell.

As used herein, the terms "nucleic acid encoding a proteoglycan polypeptide" or "nucleic acid encoding one or more proteoglycan polypeptides" refers to a nucleic acid construct that comprises a first nucleic acid sequence encoding a sequence that is sufficient for secretion and a second nucleic acid sequence encoding a polypeptide having one or more sequences for the attachment of a glycosaminoglycan chain and lacking a transmembrane domain (or like domain). Alternatively, the term "nucleic acid encoding a proteoglycan polypeptide" may refer to a nucleic acid construct that consists essentially of or consists of the first and second nucleic acid sequences.

As stated above, the nucleic acid encoding a proteoglycan polypeptide include a first nucleic acid sequence encoding a sequence sufficient for secretion. Such sequences sufficient for secretion include, but are not limited to, leader sequences, export sequences, signal peptide signal sequences and other sequences that direct the secretion of a protein or polypeptide from a cell (collectively referred to as a signal sequence). The signal sequence usually contains 13-36 amino acids, which are predominantly hydrophobic in nature. The signal sequence is recognized by a multi-protein complex termed the signal recognition particle (SRP). This signal sequence is removed, at least partially, following passage through the endoplasmic reticulum membrane.

Any such signal sequence known in the art may be used as the signal sufficient for secretion. The sequence sufficient for secretion may be normally associated with the proteoglycan polypeptide in the subject or may be a recombinant or heterologous sequence not normally associated with that proteoglycan polypeptide in the subject. In a particular embodiment, the sequence sufficient for secretion is derived from the perlecan nucleic acid sequence and is as follows: atgggtgcgggcgccgggcgcgctgctgctggcgctgctgctg (SEQ ID NO: 27). Other sequences sufficient for secretion are known to those of ordinary skill in the art. All or a part of the translated sequence sufficient for secretion may be removed during the secretion process.

In one embodiment, the polypeptide having one or more sequences for the attachment of a glycosaminoglycan chain is a polypeptide designed by the mind of man and the second nucleic acid sequence encodes such polypeptide; such a polypeptide may be a combination of segments from 1 or more naturally occurring proteoglycan polypeptides. Such a polypeptide may be designed to have particularly desired property/properties. In an additional embodiment, the polypeptide having one or more sequences for the attachment of a glycosaminoglycan chain is a proteoglycan polypeptide and the second nucleic acid sequence encodes one or more proteoglycan polypeptides. The term "proteoglycan polypeptide" is meant to be broadly defined and includes known and, as yet, unknown proteoglycans, proteoglycans created de novo and fragments of the foregoing, provided such proteoglycans created de novo, and fragments have at least one glycosaminoglycan chain. Therefore, the proteoglycan polypeptide may be a full length proteoglycan protein, or a fragment thereof that is naturally occurring. Exemplary proteoglycan proteins include, but are not limited to, aggrecan, versican, lumican, syndecan 1-4, glypican 1-5, betaglycan, NG2/CSPG4, CD44/Epican, fibromodulin, PRELP, keratocan, osteoadherin/osteomodulin, epiphycan, osteoglycin/mimecan, neurocan/CSPG3, brevican, bamacan, agrin and serglycin. The nucleic acid sequences for such proteoglycans are provided, in SEQ ID NOS: 1-26, respectively. In one embodiment, such proteoglycan polypeptide does not include decorin or biglycan. In an alternate embodiment, such proteoglycan polypeptide does not include perlecan. The term "fragment" is meant to refer to any nucleic acid comprising at least 30 contiguous nucleic acid residues, provided that such fragment encodes for at least one site for glycosaminoglycan attachment. The nucleic acid encoding a proteoglycan polypeptide may be natural and synthetic. In an alternate embodiment, the second nucleic acid sequence is chimeric and contains nucleic acid encoding portions from more than one proteoglycan protein.

In a further embodiment, the second nucleic acid sequence can vary from the nucleic acid encoding the naturally occurring proteoglycan protein of fragment thereof, provided that the modified nucleic acid encodes a protein or polypeptide that functions to effect the healing of a wound or cutaneous injury as the naturally occurring proteoglycan protein or fragment thereof. These altered sequences include those caused by point mutations (referred to herein as mutants), those due to the degeneracies of the genetic code (referred to herein as degenerate variants) or naturally occurring allelic variants (referred to herein as allelic variants), and further modifications that have been introduced by genetic engineering (referred to herein as variants). A variant or mutant includes, but is not limited to, those species engineered to have more or less sites for glycosaminoglycan attachment. The activity of the protein or polypeptide encoding such mutants, degenerate variants, allelic variants and variants may be assessed by the methods disclosed herein and as known in the art. All such modifications to the nucleic acid coding for a proteoglycan polypeptide are encompassed by this disclosure.

Techniques for introducing changes in a nucleic acid coding for a proteoglycan polypeptide such that the expressed proteoglycan polypeptide is different from a naturally occurring proteoglycan protein or fragment thereof are well known in the art. Such modifications include the deletion, insertion or substitution of bases which result in changes in the amino acid sequence. Changes may be made to increase the activity, to increase its biological stability or half-life, to change its glycosylation pattern, confer temperature sensitivity or to alter the expression pattern and the like.

In the present disclosure, the delivery of the glycosaminoglycan chains to the site of a wound or cutaneous injury may be desired. As such the exact structure of the protein/polypeptide may not be as critical as in other applications (such as receptor binding and the like). Therefore, the present disclosure contemplates that the various changes may be made in the nucleic acid encoding a proteoglycan polypeptide without appreciable loss of the ability of the expressed polypeptide to effectively deliver the glycosaminoglycan chains to the site of a wound or cutaneous injury and as such the modifications to the nucleic acid encoding a proteoglycan polypeptide are within the scope of the disclosure. In one embodiment, the site of glycosaminoglycan attachment is not altered.

Conservative substitutions of amino acids are well-known and may be made generally without altering the biological activity of the resulting protein or polypeptide. For example, such conservative substitutions are generally made by interchanging within the groups of polar residues, charged residues, hydrophobic residues, small residues, and the like. For example, certain amino acids may be substituted for other amino acids in a protein/polypeptide structure without appreciable alteration of the protein/polypeptide structure. In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein/polypeptide, which in part defines the activity of the protein/polypeptide.

Each amino acid has been assigned a hydropathic index on the basis of its hydrophobicity and charge characteristics (Kyte and Doolittle, 1982) as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein/polypeptide with similar structure and/or biological activity. In making such changes, the hydropathic indices of the substituted amino acids are within +/−2, +/−1 or +/−0.5.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of a protein/polypeptide. The following hydrophilicity values have been assigned to amino acid residues: arginine (+3.0); lysine (+3.0); aspartate (+3.0.+−0.1); glutamate (+3.0.+−0.1); serine (.+−.0.3); asparagine (+0.2); glutamine (+0.2) glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still result in a protein/polypeptide with similar structure and/or biological activity. In making such changes, the hydrophilicity values of the substituted amino acids are within +/−2, +/−1 or +/−0.5.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The second nucleic acid sequence may optionally contain and be operatively associated with one or more sequences necessary or desirable for expression. Alternatively, the nucleic acid encoding a proteoglycan polypeptide may be a part of a vector as described herein and the vector may contain such sequences. Such sequences include, but are not limited to, a promoter, enhancer, transcription factor binding site and other gene expression regulatory sequences (referred to collectively as "expression elements"). The expression elements of these vectors may vary in their strength and specificity. Depending on the host and/or vector utilized, any one of a number of suitable expression elements may be used. The expression elements may be normally associated with the nucleic acid in the subject. Alternatively, the expression elements may be recombinant or heterologous elements that are not normally associated with that nucleic acid in the subject. In any event, the expression element(s) is/are "operably linked" to the nucleic acid, which refers to the situation of an expression element in such a manner as to influence the expression of the proteoglycan polypeptide from the nucleic acid encoding the proteoglycan polypeptide. Examples are: tissue specific expression elements, including distinct promoter and enhancer sequences that are derived from different sources and engineered to produce an expression element to regulate the expression of the transferred DNA in specific cell types. Expression elements isolated from the genome of viruses that grow in mammalian cells, (e.g., RSV, vaccinia virus 7.5K, SV40, HSV, adenoviruses MLP, MMTV LTR and CMV promoters) may be used, as well as promoters produced by recombinant DNA or synthetic techniques.

In some instances, the expression elements may be constitutive or inducible and can be used under the appropriate conditions to direct high level or regulated expression of the nucleic acid encoding a proteoglycan polypeptide. Specific initiation signals are also required for sufficient translation of the nucleic acid encoding a proteoglycan polypeptide. These signals include, but are not limited to, the ATG initiation codon and adjacent sequences. In cases where the entire coding sequence of a proteoglycan protein, including the initiation codon and adjacent sequences, are used (either alone or in combination with a vector), no additional translational control signals may be needed. However, in cases where only a portion of the coding sequence of a proteoglycan protein (such as a fragment or a synthesized nucleic acid) is used, exogenous translational control signals, including, but not limited to, the ATG initiation codon may be provided. Furthermore, the initiation codon must be in phase with the reading frame of the coding sequences to ensure translation of the entire insert. These exogenous translational control signals and initiation codons can be of a variety of origins, both natural and synthetic. The efficiency and control of expression may be enhanced by the inclusion of transcription attenuation sequences, enhancer elements, and the like.

As used herein, the term "proteoglycan polypeptide" refers to a polypeptide expressed from a nucleic acid encoding a proteoglycan polypeptide that is secreted from a cell where said proteoglycan polypeptide is produced; as such a proteoglycan polypeptide has one or more attached glycosaminoglycan chains. The proteoglycan polypeptide may be a full length proteoglycan protein, or a fragment thereof. A proteoglycan polypeptide may contain one or more than one attached glycosaminoglycan chains; furthermore, it should be noted that the nature, identity and number of attached glycosaminoglycan chains can vary, even for the same proteoglycan polypeptide, depending on the post-translational glycation of the proteoglycan by the subject.

Compositions

Useful compositions comprising the nucleic acids of the present disclosure may be formulated according to methods known in the art. In one embodiment, such compositions are pharmaceutical compositions. The compositions disclosed may comprise one or more of the nucleic acids of the present disclosure, such as those nucleic acids of the first embodiment, in combination with a pharmaceutically acceptable carrier. Examples of such carriers and methods of formulation may be found in Remington: The Science and Practice of Pharmacy (20$^{th}$ Ed., Lippincott, Williams & Wilkins, Daniel Limmer, editor). To form a pharmaceutically acceptable composition suitable for effective administration, such compositions will contain an effective amount of disclosed proteoglycan nucleic acid, and other protein, nucleic acid, or modulator compounds. The nucleic acid molecules may be used in combination with a suitable vector as described herein and the described compositions may comprise such vector.

The pharmaceutical compositions of the disclosure may be used in the treatment and prevention methods of the present disclosure. Such compositions are administered to a subject in amounts sufficient to deliver a therapeutically effective amount of the contained nucleic acids so as to be effective in the treatment and prevention methods disclosed herein. The therapeutically effective amount may vary according to a variety of factors such as, but not limited to, the subject's condition, weight, sex and age. Other factors include the mode and site of administration. The pharmaceutical compositions may be provided to the subject in any method known in the art. Exemplary routes of administration include, but are not limited to, subcutaneous, intravenous, topical, epicutaneous, oral, intraosseous, and intramuscular. The compositions of the present disclosure may be administered only one time to the subject or more than one time to the subject. Furthermore, when the compositions are administered to the subject more than once, a variety of regimens may be used, such as, but not limited to, one per day, once per week, once per month or once per year. The compositions may also be administered to the subject more than one time per day. The therapeutically effective amount of the nucleic acid molecules and appropriate dosing regimens may be identified by routine testing in order to obtain optimal activity, while minimizing any potential side effects. In addition, co-administration or sequential administration of other agents may be desirable.

The compositions of the present disclosure may be administered systemically, such as by intravenous administration, or locally such as by subcutaneous injection or by application of a paste or cream. The production of proteoglycan polypeptides by the cells may be verified by sampling the tissues and measuring expression by conventional means, such as Northern blotting or Western blotting.

The compositions of the present disclosure may further comprise agents which improve the solubility, half-life, absorption, etc. of the nucleic acid molecules or the proteoglycan peptide molecules, either before or after secretion. Furthermore, the compositions of the present disclosure may further comprise agents that attenuate undesirable side effects and/or or decrease the toxicity of the nucleic acid molecules or produced proteoglycan peptides. Examples of such agents are described in a variety of texts, such a, but not limited to, Remington: The Science and Practice of Pharmacy (20$^{th}$ Ed., Lippincott, Williams & Wilkins, Daniel Limmer, editor).

The compositions of the present disclosure can be administered in a wide variety of dosage forms for administration. For example, the compositions can be administered in forms, such as, but not limited to, tablets, capsules, sachets, lozenges, troches, pills, powders, granules, elixirs, tinctures, solutions, suspensions, elixirs, syrups, ointments, creams, pastes, emulsions, or solutions for intravenous administration or injection. Other dosage forms include administration transdermally, via patch mechanism or ointment. Any of the foregoing may be modified to provide for timed release and/or sustained release formulations.

In the present disclosure, the pharmaceutical compositions contain at least one nucleic acid molecule encoding one or more proteoglycan polypeptides as an active ingredient, and are typically administered with a pharmaceutically acceptable carrier. The nucleic acid molecule may be administered with or as a part of a vector of the present disclosure. Such pharmaceutically acceptable carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, for oral administration in solid form, such as but not limited to, tablets, capsules, sachets, lozenges, troches, pills, powders, or granules, the nucleic acid molecules of the present disclosure may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

For oral liquid forms, such as but not limited to, tinctures, solutions, suspensions, elixirs, syrups, the nucleic acid molecules of the present disclosure can be dissolved in diluents, such as water, saline, or alcohols. Furthermore, the oral liquid forms may comprise suitably flavored suspending or dispersing agents such as the synthetic and natural gums, for example, tragacanth, acacia, methylcellulose and the like. Moreover, when desired or necessary, suitable and coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The nucleic acid molecules of the present disclosure can be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkylbeta-aminopropionates, and 2-alkylimidazoline quaternary ammonium salts, and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight.

Topical dosage forms, such as, but not limited to, ointments, creams, pastes, emulsions, containing the nucleic acid molecule of the present disclosure, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery or may be applied to a bandage or dressing for delivery directly to the site of a wound or cutaneous injury.

The compounds of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The compounds of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Methods of Treatment and Prevention

In one embodiment, the teachings of the present disclosure provide for the use of the nucleic acids and compositions of the present disclosure in a method of treating a wound or cutaneous injury. The method of treatment comprises the steps of providing such nucleic acid or composition containing such nucleic acid and administering the same in a therapeutically effective amount to effectively treat the wound or cutaneous injury in a subject in need of such treatment.

In one embodiment, the teachings of the present disclosure provide for use of such nucleic acids and compositions in a method of preventing a wound or cutaneous injury. The method of preventing or suppressing comprises the steps of providing such nucleic acid or composition containing such nucleic acid and administering the same in a therapeutically effective amount to effectively prevent the wound or cutaneous injury in a subject in need of such prevention.

Nucleic Acid Delivery Methods

A variety of methods are currently known to enable delivery of the nucleic acid molecules of the present disclosure to a target cell in a subject. Any such methods may be used. It has long been an accepted idea that nucleic acid molecules can not be delivered across the stratum corneum. However, studies in the last 10 years have shown that plasmid DNA can be delivered across the skin barrier and cause measurable protein expression through the use of a variety of lipid vesicles (Raghavachari, et al., *J Pharm Sci* 91(3): 615-22, 2002; Patil, et al., *Aaps J* 7(1): E61-77, 2005). In addition, virus incorporating the DNA of choice successfully transfects cells of many different tissue types and expresses the desired polypeptide (Patil, et al., *Aaps J* 7(1): E61-77, 2005). Viral infection of skin cells has been successful by subcutaneous injection (Setoguchi, et al., *J Invest Dermatol* 102(4): 415-21, 1994), through the use of gene guns or pressure delivery devices (Gaffal, et al., *Eur J. Cell Biol.*, e-publication, Aug. 21, 2006), and by direct application after light abrasion (Shi, et al., *J Virol* 75(23): 11474-82, 2001). Delivery of nucleic acids through the stratum corneum has recently become a feasible and viable method for numerous therapies and vaccination techniques. These techniques are discussed to demonstrate applicability of the present invention.

The present disclosure envisions the delivery of the nucleic acid molecules of the present disclosure to living cells in a subject, such as, but not limited to, the cells of the epithelium. Such cell types include, but are not limited to, epidermal keratinocyte (differentiating epidermal cell), epidermal basal cell (stem cell), keratinocyte of fingernails and toenails, nail bed basal cell (stem cell), medullary hair shaft cell, cortical hair shaft cell, cuticular hair shaft cell, cuticular hair root sheath cell, hair root sheath cell of Huxley's layer, hair root sheath cell of Henle's layer, external hair root sheath cell, hair matrix cell (stem cell), prokaryotic cell (bacteria), eukaryotic cells (plant and animal cell), surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, urinary epithelium cell (lining urinary bladder and urinary ducts), salivary gland mucous cell (polysaccharide-rich secretion), salivary gland serous cell (glycoprotein enzyme-rich secretion), Von Ebner's gland cell in tongue (washes taste buds), mammary gland cell (milk secretion), lacrimal gland cell (tear secretion), ceruminous gland cell in ear (wax secretion), eccrine sweat gland dark cell (glycoprotein secretion), eccrine sweat gland clear cell (small molecule secretion), apocrine sweat gland cell (odoriferous secretion, sex-hormone sensitive), gland of Moll cell in eyelid (specialized sweat gland), sebaceous gland cell (lipid-rich sebum secretion), Bowman's gland cell in nose (washes olfactory epithelium), Brunner's gland cell in duodenum (enzymes and alkaline mucus), seminal vesicle cell (secretes seminal fluid components, including fructose for swimming sperm), prostate gland cell (secretes seminal fluid components), bulbourethral gland cell (mucus secretion), Bartholin's gland cell (vaginal lubricant secretion), gland of Littre cell (mucus secretion), uterus endometrium cell (carbohydrate secretion), isolated goblet cell of respiratory and digestive tracts (mucus secretion), stomach lining mucous cell (mucus secretion), gastric gland zymogenic cell (pepsinogen secretion), gastric gland oxyntic cell (hydrochloric acid secretion), pancreatic acinar cell (bicarbonate and digestive enzyme secretion), paneth cell of small intestine (lysozyme secretion), type II pneumocyte of lung (surfactant secretion), Clara cell of lung, anterior pituitary cells, somatotropes, lactotropes, thyrotropes, gonadotropes, corticotropes, intermediate pituitary cell, secreting melanocyte-stimulating hormone, magnocellular neurosecretory cells, secreting oxytocin, secreting vasopressin, gut and respiratory tract cells secreting serotonin, secreting endorphin, secreting somatostatin, secreting gastrin, secreting secretin, secreting cholecystokinin, secreting insulin, secreting glucagon, secreting bombesin, thyroid gland cells, thyroid epithelial cell, parafollicular cell, parathyroid gland cells, parathyroid chief cell, oxyphil cell, adrenal gland cells, chromaffin cells, secreting steroid hormones (mineralcorticoids and glucocorticoids), Leydig cell of testes secreting testosterone, theca interna cell of ovarian follicle secreting estrogen, corpus luteum cell of ruptured ovarian follicle secreting progesterone, kidney juxtaglomerular apparatus cell (renin secretion), macula densa cell of kidney, peripolar cell of kidney, mesangial cell of kidney, intestinal brush border cell (with microvilli), exocrine gland striated duct cell, gall bladder epithelial cell, kidney proximal tubule brush border cell, kidney distal tubule cell, ductulus efferens non-ciliated cell, epididymal principal cell, epididymal basal cell, hepatocyte (liver cell), white fat cell, brown fat cell, liver lipocyte, type I pneumocyte (lining air space of lung), pancreatic duct cell (centroacinar cell), nonstriated duct cell (of sweat gland, salivary gland, mammary gland, etc.), kidney glomerulus parietal cell, kidney glomerulus podocyte, loop of Henle thin segment cell (in kidney), kidney collecting duct cell, duct cell (of seminal vesicle, prostate gland, etc.), blood vessel and lymphatic vascular endothelial fenestrated cell, blood vessel and lymphatic vascular endothelial continuous cell, blood vessel and lymphatic vascular endothelial splenic cell, synovial cell (lining joint cavities, hyaluronic acid secretion), serosal cell (lining peritoneal, pleural, and pericardial cavities), squamous cell (lining perilymphatic space of ear), squamous cell (lining endolymphatic space of ear), columnar cell of endolymphatic sac with microvilli (lining endolymphatic space of ear), columnar cell of endolymphatic sac without microvilli (lining endolymphatic space of ear), dark cell (lining endolymphatic space of ear), vestibular membrane cell (lining endolymphatic space of ear), stria vascularis basal cell (lining endolymphatic space of ear), stria vascularis marginal cell (lining endolymphatic space of ear), cell of Claudius (lining endolymphatic space of ear), cell of Boettcher (lining endolymphatic space of ear), choroid plexus cell (cerebrospinal fluid secretion), pia-arachnoid squamous cell, pigmented ciliary epithelium cell of eye, non-pigmented ciliary epithelium cell of eye, corneal endothelial cell, respiratory tract ciliated cell, oviduct ciliated cell (in female), uterine endometrial ciliated cell (in female), rete testis ciliated cell (in male), ductulus efferens ciliated cell (in male), ciliated ependymal cell of central nervous system (lining brain cavities), ameloblast epithelial cell (tooth enamel secretion), planum semilunatum epithelial cell of vestibular apparatus of ear (proteoglycan secretion), organ of Corti interdental epithelial cell (secreting tectorial membrane covering hair cells), loose connective tissue fibroblasts, corneal fibroblasts, tendon fibroblasts, bone marrow reticular tissue fibroblasts, other nonepithelial fibroblasts, pericyte, nucleus pulposus cell of intervertebral disc, cementoblast/cementocyte (tooth root bonelike cementum secretion), odontoblast/odontocyte (tooth dentin secretion), hyaline cartilage chondrocyte, fibrocartilage chondrocyte, elastic cartilage chondrocyte, osteoblast/osteocyte, osteoprogenitor cell (stem cell of osteoblasts), hyalocyte of vitreous body of eye, stellate cell of perilymphatic space of ear, red skeletal muscle cell (slow), white skeletal muscle cell (fast), intermediate skeletal muscle cell, nuclear bag cell of muscle spindle, nuclear chain cell of muscle spindle, satellite cell (stem cell), heart muscle cell, nodal heart muscle cell, purkinje fiber cell, smooth muscle cell (various types), myoepithel al cell of iris, myoepithelial cell of exocrine glands, red blood cell, erythrocyte (red blood cell), megakaryocyte (platelet precursor), monocyte, connective tissue macrophage (various types), epidermal Langerhans cell, osteoclast (in bone), dendritic cell (in lymphoid tissues), microglial cell (in central nervous system), neutrophil granulocyte, eosinophil granulocyte, basophil granulocyte, mast cell, helper T cell, suppressor T cell, cytotoxic T cell, B cells, natural killer cell, reticulocyte, stem cells and committed progenitors for the blood and immune system (various types), auditory inner hair cell of organ of Corti, auditory outer hair cell of organ of Corti, basal cell of olfactory epithelium (stem cell for olfactory neurons), cold-sensitive primary sensory neurons, heat-sensitive primary sensory neurons, merkel cell of epidermis (touch sensor), olfactory receptor neuron, pain-sensitive primary sensory neurons (various types), photoreceptor rod cell of eye, photoreceptor blue-sensitive cone cell of eye, photoreceptor green-sensitive cone cell of eye, photoreceptor red-sensitive cone cell of eye, proprioceptive primary sensory neurons (various types), touch-sensitive primary sensory neurons (various types), type I carotid body cell (blood pH sensor), type II carotid body cell (blood pH sensor), type I hair cell of vestibular apparatus of ear (acceleration and gravity), type II hair cell of vestibular apparatus of ear (acceleration and gravity), type I taste bud cell, cholinergic neural cell (various types), adrenergic neural cell (various types), peptidergic neural cell (various types), inner pillar cell of organ of Corti, outer pillar cell of organ of Corti, inner phalangeal cell of organ of Corti, outer phalangeal cell of organ of Corti, border cell of organ of Corti, hensen cell of organ of Corti, vestibular apparatus supporting cell, type I taste bud supporting cell, olfactory epithelium supporting cell, schwann cell, satellite cell (encapsulating peripheral nerve cell bodies), enteric glial cell, astrocyte (various types), neuron cells (large variety of types, still poorly classified), oligodendrocyte, spindle neuron, anterior lens epithelial cell, crystallin-containing lens fiber cell, karan cells, melanocyte, retinal pigmented epithelial cell, oogonium/oocyte, spermatid, spermatocyte, spermatogonium cell (stem cell for spermatocyte), spermatozoon, ovarian follicle cell, Sertoli cell (in testis), and thymus epithelial cell. Such cells are typically mammalian cells and in one embodiment, human cells. Therefore, the vectors chosen for such delivery must be suitable for delivery of the nucleic acid molecules of the present disclosure to living cells of mammalian origin.

Vectors encompassed by the present disclosure are meant to include a broad range of mechanisms. Vectors include both viral and non-viral vectors. Non-viral vectors include, but are not limited to, plasmids, liposomes, electrically charged lipids (such as cytofectins), DNA-protein complexes, and biopolymers. Such non-viral vectors may be transferred into cells using any of the methods known in the art, including calcium phosphate coprecipitation, lipofection, protoplast fusion, receptor-mediated gene delivery, naked DNA injection, electroporation and bioballistic or particle acceleration.

Suitable plasmids for use as vectors include, but are not limited to, pcDNA3, pMC1neo, pXT1, pSG5, EBO-pSV2, pBPV-1, pBPV-MMTneo, pRSVgpt, pRSVneo, pSV2-dhfr, pUCTag, IZD35, pHB-Apr-1-neo, EBO-pcD-XN, pcDNA1/amp, pcDNA1/neo, pRc/CMV, pSV2gpt, pSV2neo, pSV2dhfr, pTk2, pMSG, pSVT7, pKoneo and pHyg. Such plasmids may contain an origin of replication for autonomous replication in host cells, selectable markers, a number of useful restriction enzyme sites, a potential for high copy number, and promoters active in a particular cell type. A promoter is defined as a nucleic acid sequence that directs RNA polymerase to bind to the nucleic acid and initiate RNA synthesis.

Viral vectors may be transferred into cells using any method known in the art, including infection and transfection.

Viral vectors that may be used in the present invention include, but are not limited to, vectors derived from adenoviral vectors, retroviral vectors, lentiviral vectors, bovine papilloma viruses, Epstein-Barr virus, adeno-associated viruses pox viruses, baculovirus, vaccinia virus, herpes simplex virus, and hybrids of two or more viral vector types.

Adenoviruses are eukaryotic DNA viruses that can be modified to efficiently deliver nucleic acid to a variety of cell types. Various serotypes of adenovirus exist, including type 2 and type 5 human adenoviruses and adenoviruses of animal origin. In one embodiment, the adenovirus is replication defective and comprises the LTRs, an encapsidation sequence, and a nucleic acid molecule of the present disclosure. In, a particular embodiment, at least the E1 region of the adenoviral vector is nonfunctional. Other regions may also be modified, including the E3 region (see WO95/02697), the E2 region (see WO94/28938), the E4 region (see WO94/28152, WO94/12649, and WO 95/02697), or in any of the late genes L1-L5.

Adenovirus vectors can be prepared by techniques known to a person skilled in the art. In particular they can be prepared by homologous recombination between an adenovirus and a plasmid which carries a nucleic acid molecule of the present disclosure. Homologous recombination is effected following cotransfection of the adenovirus and plasmid into an appropriate cell line. The cell line employed should be transformable by said components and contain sequences which are able to complement the defective regions in the replication defective adenovirus (if a replication defective adenovirus is used). Examples of cell lines which may be used are the human embryonic cell line 293 (Graham et al., J. Gen. Virol. 36, 59 (1977)) which contains the left-hand portion of the genome of an Ad5 adenovirus (12%) integrated into its genome, and cell lines which are able to complement the E1 and E4 functions, as described in WO94/26914 and WO95/02697. Recombinant adenoviruses are recovered and purified using standard biological techniques which are well known to those having ordinary skill in the art.

One class of useful adenovirus vectors may be prepared according to Bett et al., Proc. Natl. Acad. Sci. (USA) 91:8802-6 (1994), which describes a system for construction of adenovirus vectors with insertions or deletions in the E1 and E3 regions.

Adenoviral vectors can be produced at high titers (e.g. $10^{10}$-$10^{12}$ infectious units per ml), and can be used to transiently express the desired proteoglycan polypeptides in infected target cells in vitro or in vivo.

Retroviruses are integrating viruses which generally infect dividing cells. Lentiviruses are a type of retrovirus that is also capable of infecting non-dividing cells. The following discussion is applicable generally to retroviruses, including lentiviruses. The retrovirus genome includes two long terminal repeats (LTRs), an encapsidation sequence and three coding regions (gag, pol and env). The construction of recombinant retroviral vectors is known to those of skill in the art.

In recombinant retroviral vectors, the gag, pol, and env genes are generally deleted, in whole or in part, and replaced with a heterologous nucleic acid sequence of interest. These vectors can be constructed from different types of retrovirus, such as M-MuLV, MSV (murine Moloney sarcoma virus), HaSV (Harvey sarcoma virus), SNV (spleen necrosis virus), RSV (Rous sarcoma virus) and Friend virus.

In general, in order to construct recombinant retroviruses containing a nucleic acid molecule of the present disclosure, a plasmid is constructed which contains the LTRs, the encapsidation sequence and the coding sequence of a nucleic acid molecule of the present disclosure. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art. In particular the cell line PA317 (U.S. Pat. No. 4,861,719), the PsiCRIP cell line (WO90/02806), and the GP+envAm-12 cell line (WO89/07150) may be used. Recombinant retroviral vectors are purified by standard techniques known to those having ordinary skill in the art.

Retroviral vectors derived from lentiviruses such as HIV-1, HIV-2, and SIV can be used for delivery to nondividing cells. These viruses can be pseudotyped with the surface glycoproteins of other viruses, such as M-MuLV or vesicular stomatitis virus (VSV). The production of high titer HIV-1 pseudotyped with VSV glycoprotein has been disclosed by Bartz and Vodicka, Methods 12(4):337-42 (1997), and multiply attenuated lentiviral vectors have been disclosed by Zufferey et al., Nature Biotechnology 15:871-75 (1997). Such lentiviral vectors can infect nondividing cells, have a broad host range, and can be concentrated to high titers by ultracentrifugation.

Chimeric adenoviral/retroviral vector systems can also be used to achieve efficient gene delivery and long term expression. A chimeric viral system in which adenoviral vectors are used to produce transient retroviral producer cells in vivo, such that progeny retroviral particles infect neighboring cells, has been described by Feng et al., Nature Biotechnology 15:866-70 (September 1997).

Vectors encoding proteoglycan polypeptides of the present disclosure can be generated in several ways using standard techniques of molecular biology. The vector should be suitable for stable, high-level expression in mammalian cells. Retroviral vectors containing strong viral promoters, such as the immediate-early human cytomegalovirus (CMV)/enhancer, to drive the expression of the inserted nucleic acid, may be used.

Vectors encoding expression of the proteoglycan polypeptides of the present disclosure are administered to a subject as described herein.

Effective amounts may be determined by the physician or by another qualified medical professional. Recombinant viruses are generally formulated and administered in the form of doses of from about $10^4$ to about $10^{14}$ pfu, from about $10^6$ to about $10^9$, or from about $10^6$ to about $10^8$.

In carrying out the nucleic acid manipulations described herein, many techniques for manipulating and modifying nucleic acids may be used. Merely exemplifying such techniques are the following: *Gene Probes for Bacteria* (Macario and De Marcario, editors, Academic Press Inc., 1990); *Genetic Analysis, Principles Scope and Objectives* (John R. S. Ficham, Blackwell Science Ltd., 1994); *Recombinant DNA Methodology II* (Ray Wu, editor, Academic Press, 1995); *Molecular Cloning. A Laboratory Manual* (Maniatis, Fritsch, and Sambrook, editors, Cold Spring Harbor Laboratory, 1982); *PCR (Polymerase Chain Reaction)*, (Newton and Graham, editors, Bios Scientific Publishers, 1994). Each of the foregoing references cited herein are incorporated by reference as if fully set forth in this disclosure.

The following examples illustrate certain embodiments of the present disclosure without, however, limiting the same thereto.

EXAMPLES

Example 1

Exemplary Production of a Nucleic Acid Sequence Encoding a Secreted Proteoglycan Polypeptide The isolated nucleic acid molecule encoding one or more proteoglycan polypeptides comprises a first nucleic acid sequence encoding a sequence that is sufficient for secretion and a second nucleic acid sequence encoding a polypeptide having one or more sequences for the attachment of a glycosaminoglycan chain and lacking a transmembrane domain (or like domain). The proteoglycan polypeptide produced after transcription, translation and glycosylation is secreted from the cell in which it is produced due to the presence of the signal sufficient for excretion.

The signal sufficient for excretion may be any sequence that directs the secretion of a protein or polypeptide from a cell. As a specific example, the signal sequence from the perlecan proteoglycan may be used. The signal sequence from the perlecan proteoglycan has the sequence atggggtggcgggcgccgggcgcgctgctgctggcgctgctgctg (SEQ ID NO. 27). This signal sequence, as well as others known in the art, can be incorporated into the isolated nucleic acid molecule encoding one or more proteoglycan polypeptides by methods known in the art. The signal sequence is generally placed on the 5' end of the nucleic acid (the $NH_2$-terminus of the proteoglycan polypeptide). Proteoglycan polypeptides having the signal sequence set forth in SEQ ID NO: 27 were secreted by fibroblasts and endothelial cells when expressed in these cell types.

The design and construction of an exemplary nucleic acid of the present disclosure is provided below to further illustrate the concepts of the disclosure. For the exemplary proteoglycan perlecan, a 20-mer antisense 3' perlecan domain 1 (D1) primer was made extending to base 639 of the NM 005529 GenBank sequence. Reverse transcription from total dermal microvascular endothelial cell mRNA was performed, and the resulting cDNA was amplified by PCR with an upstream 19-mer primer extending from base 38 of the NM 005529 sequence and included the signal sequence for secretion from cell. Subsequently, a Bgl2 restriction enzyme site was synthesized to extend from the 5' end of the 38 and 639 primers. PCR was repeated on the original D1 amplification product, and the PCR product was Bgl2 digested, producing the D1Bgl2 transgene. This product was subsequently ligated into the Bgl2 cloning site of the adenoviral expression system (Adenovator, Qbiogene) resulting in a forward perlecanD1-Ad clone. By this method, a recombinant perlecan D1 expression product (rD1) was generated. A control RevD1-Ad clone with the D1 insert in reverse orientation relative to the CMV-5 promoter was also produced.

Primary human endothelial cells or dermal fibroblasts were seeded on plastic and infected with the perlecanD1-Ad or control RevD1-Ad. Infections were performed 16-24 h after seeding in DMEM, with 10% FBS with varying infectious doses inoculated into either 50 µl or 250 µl medium in 96-well or 24-well culture plates, respectively. Infections were allowed to proceed with constant rocking for 16-24 h at 37° C., 5% $CO_2$, at which time, media was changed to DMEM supplemented with F12 with, or without, 1% serum. Infected cell cultures were incubated for various time periods.

After several days of incubation, conditioned medium was removed and separated from any loose cell debris by centrifuge then saved frozen for assay. The residual cell and accumulated subcellular matrix were washed once in PBS, then either fixed with cold methanol, or solubilized with either 50 or 200 μl 0.1% SDS in water containing protease inhibitor cocktail (Product # P 2714, Sigma Aldrich Corp, St. Louis, Mo.), in 96-well or 24-well assays, respectively.

Figure 1B:
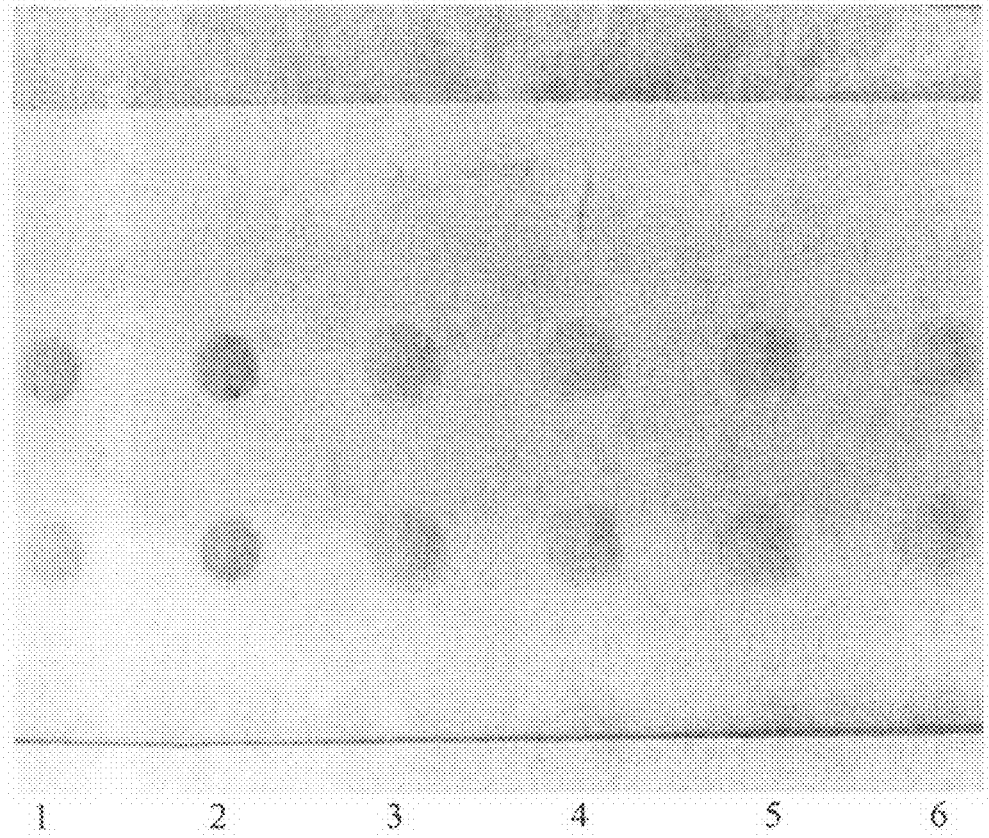

The solubilized residual cell matrix samples and conditioned media samples were stained with anti-D1 monoclonal antibody (mAb) A71 (FIG. 1A) or the anti-D5 mAb A74 (FIG. 1B). For each of FIGS. 1A and 1B, 100 μl of the solubilized residual cell matrix samples and 100 μl of the conditioned medium were applied to nitrocellulose in duplicate wells in a 96-well dot-blot format. The nitrocellulose was blocked with PBS containing Tween-20 detergent, 0.1% (PBS/Tween), and primary antibody was applied at 1 μg/ml. After overnight incubation with primary antibody, 1 μg/ml secondary anti-mouse AP conjugate was applied in PBS/Tween for 2 hours and the blots developed with BCIP. Columns 1 and 2 are solubilized residual cell matrix from primary human endothelial cells cultures following 9 days of culture after infection with perlecanD1-Ad and control RevD1-Ad, respectively. Columns 3 and 4 are conditioned medium from primary human endothelial cells cultures removed following 5 days of culture after infection with perlecanD1-Ad and control RevD1-Ad, respectively. Columns 5 and 6 are conditioned medium from primary human endothelial cells cultures removed following 6-9 days of culture after infection with perlecanD1-Ad and control RevD1-Ad, respectively.

In the solubilized residual cell matrix samples, there was some detectable mAb A71 immunoreactivity (FIG. 1A) from the infected cells (col. 1), and slightly more immunoreactivity in the control samples (col. 2), suggesting that this background was native perlecan, and that none of the recombinant had been retained in cell or subcellular matrix. Immunoreactivity of mAb A74 (FIG. 1B), which binds domain 5 (D5) of native perlecan, confirmed that the probable source of mAb A71 immunoreactivity was from native perlecan since it was of equal or greater intensity than the mAb A71 signal. Similar results were obtained with the fibroblast cultures (data not shown). Immunofluorescent analysis of fixed cells supported the evidence for the lack of accumulated rD1 in experimental wells, as neither the D1 or D5 signal was above background (not presented).

Using mAb A71 (FIG. 1A), the perlecanD1-Ad clone clearly accumulated immunoreactive product in the endothelial cell conditioned medium during 5 days of culture (col. 3), while no immunoreactivity above background was present in conditioned medium from the cultures infected with the control RevD1-Ad (col. 4). Similar results were seen in conditioned medium collected between the $5^{th}$ and $9^{th}$ day of culture (cols. 5-6). Background levels of anti-D5 immunoreactivity in conditioned medium with mAb A74 are shown in FIG. 1B cols. 3-6.

Figure 2:
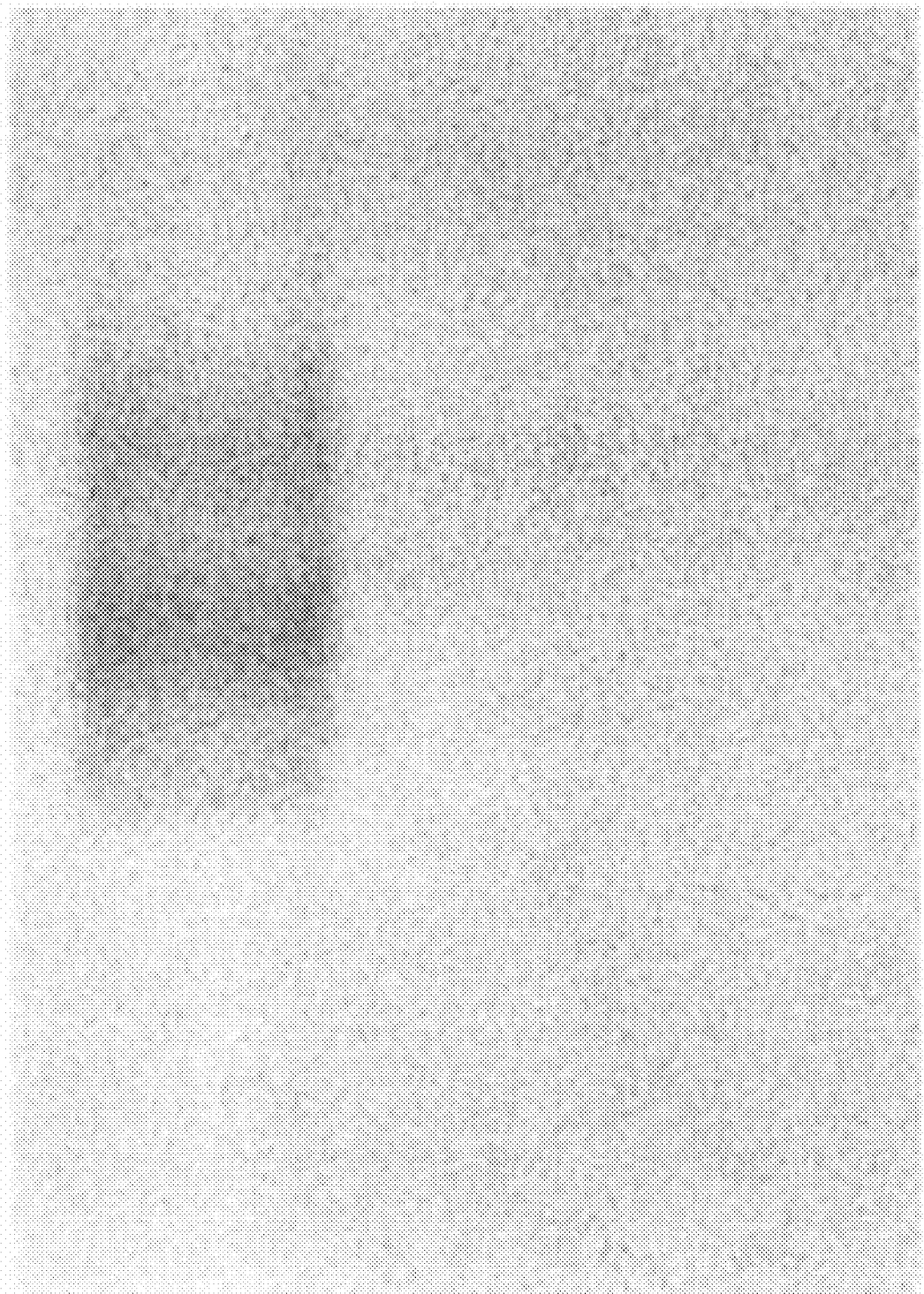
FIG. 2 shows a Western blot of fibroblast conditioned medium of perlecanD1-Ad and RevD1-Ad infected cells after 8 days of serum-free culture visualized using anti-D1 mAb A71. Lane 1 represents conditioned medium from fibroblast cultures infected with perlecanD1-Ad, and lane 2 represents control conditioned medium from fibroblast cultures infected with the RevD1-Ad. Immunoreactive material in lane 1 extends from 32 kDa to 42 kDa with the dominant band at 35 kDa.

Conditioned medium from endothelial cells infected with perlecanD1-Ad or the control RevD1-Ad was subjected to SDS-PAGE on a 4-10% gradient gel, then transferred to nitrocellulose for Western blot analysis. Antibody concentrations and manipulations were as described in FIGS. 1A and 1B. The anti-D1 A71 antibody demonstrated a broad multimeric region of staining ranging from 32-42 apparent kDa in the perlecanD1-Ad sample (FIG. 2 lane 1), but no such species in the control sample (FIG. 2, lane 2), confirming dot blot results (FIGS. 1A and 1B), and suggesting that the rD1 is probably modified with at least 11-21 kDa of GAG chains attached.

The nucleic acid manipulations can be repeated with any suitable signal sequence and the leader sequences identified may be utilized with any desired nucleic acid sequence coding for a proteoglycan polypeptide to produce a recombinant proteoglycan polypeptide for use as described herein.

The design and construction of another exemplary nucleic acid of the present disclosure is provided below to further illustrate the concepts of the disclosure. For the exemplary proteoglycan lumican, human lumican cDNA, accession number U18728, is cloned first into the CMV-5 driven mammalian expression vector pcDNA3.1/V5-His (Invitrogen) and then into the CMV-5 driven adenoviral transfer vector (AdenoVator, Qbiogene). For cloning into the adenovirus transfer vector the necessary restriction enzyme site, Bgl2, will be cloned into the ends of the lumican-V5-His transgene by PCR utilizing primers as described above for the exemplary proteoglycan perlecan.

Example 2

Figure 3A:
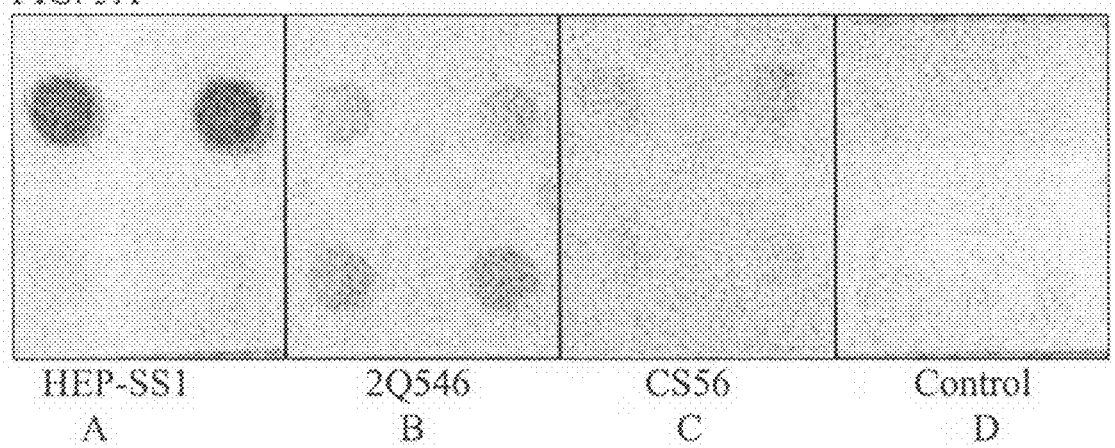
FIG. 3A shows immunoblotting (dot blot) of conditioned medium from perlecan D1-Ad infected primary human endothelial cells using a panel of antibodies that recognize variations of sulfation within heparan sulfate glycosaminoglycan chains and an antibody that recognizes chondroitin sulfate. The 2Q546 anti-heparan sulfate mAbs recognize a highly sulfated heparan sulfate, while the Hep-SS1 antibody recognizes a low sulfated heparin sulfate. The mAb CS56 recognizes chondroitin sulfate. The top row of the dot blot contains a standard heparin sulfate proteoglycan as a control, while the bottom row is conditioned medium from perlecan D1-Ad infected primary human endothelial cells. The primary antibodies used were Hep-SS1 (panel A), 2Q546 (panel B), CS-56 (panel C), and none (panel D).

Exemplary Production of a Heparan Sulfate Glycated Proteoglycan Polypeptide Generated from a Nucleic Acid Sequence Encoding a Secreted Polypeptide The endothelial conditioned medium produced as set forth in Example 1 above was subject to immunoblotting (dot blot) using a panel of antibodies that recognize variations of sulfation within heparan sulfate glycosaminoglycan chains (FIG. 3A). The 2Q546 anti-heparan sulfate mAbs recognize a highly sulfated heparan sulfate, while the Hep-SS1 antibody recognizes a low sulfated heparan sulfate. The mAb CS56 recognizes, chondroitin sulfate. The top row of the dot blot contains a standard heparan sulfate proteoglycan as a control, while the bottom row is conditioned medium from perlecan D1-Ad infected primary human endothelial cells. The primary antibodies used were Hep-SS1 (panel A), 2Q546 (panel B), CS-56 (panel C), and none (panel D); a secondary anti-mouse IgM-AP conjugate followed by BCIP was used for visualization. The procedure was performed as described for FIGS. 1A and 1B.

Conditioned medium from the perlecanD1-Ad infected endothelial cell cultures (FIG. 3A, bottom row) was poorly immunoreactive with the Hep-SS1 antibodies (panel A), relative to the strong signal from a standard aliquot of murine heparan sulfate proteoglycan 2. To the contrary, immunoreactivity of the conditioned medium with the 2Q546 antibodies (FIG. 3A, panel B) was strong relative to immunoreactivity with the standard HSPG.

Figure 3B:
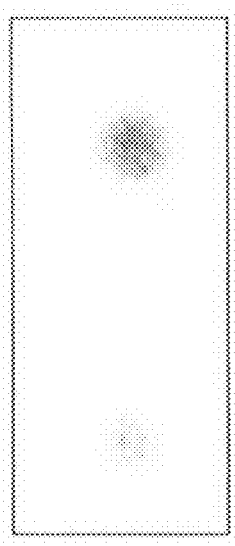
FIG. 3B shows immunoblotting (dot blot) of conditioned medium from perlecanD1-Ad (top) and RevD1-Ad (bottom) infected primary human endothelial cells after staining using mAB 2Q546.

FIG. 3B shows immunoblotting of perlecanD1-Ad (top) paired with control conditioned medium (bottom) visualized with mAb 2Q546; antibody concentrations and manipulations were as described in FIG. 3A. Given that the control conditioned medium contained significantly lower levels of immunoreactivity with the 2Q546 antibody (FIG. 3B), these data suggested that the rD1 expressed from endothelial cells in vitro was decorated with heparan sulfate which had been modified to a highly sulfated and charged state.

Figure 4:
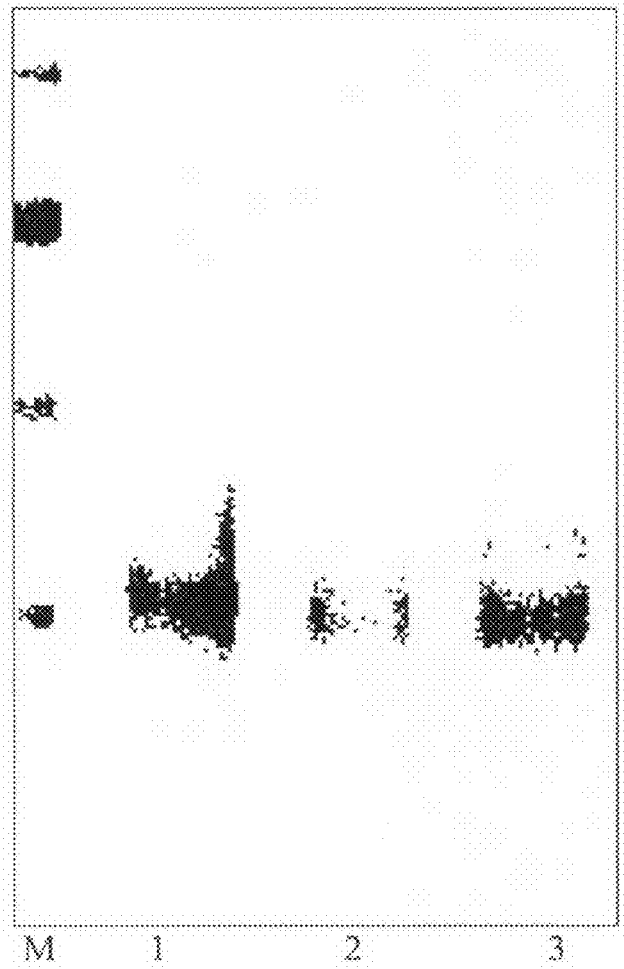
FIG. 4 shows a Western blot rD1 from conditioned medium after to enzyme degradation 1 mU of heparatinase I (lane 2), which degrades regions of heparan sulfate which have low sulfate density, or with 20 mU of chonclroitinase abc (lane 1), which removes chondroitin sulfate chains, or with only buffer (lane 3).

Immunoreactivity of the blotted conditioned medium with an anti-CS monoclonal antibody CS56 (FIG. 3A, panel C) showed slight reactivity (lower row) beyond background (panel D). However, the slight CS56 reactivity detected in the conditioned medium was at the background level also found in the control conditioned medium (data not shown). These data suggested that the rD1 from in vitro endothelial cell culture conditioned medium was not decorated with chondroitin sulfate.

rD1 from conditioned medium was subject to enzyme degradation to further determine the nature of the glycosaminoglycan chains (FIG. 4). Enzyme digestion of the rD1 with either 1 mU of heparatinase I (lane 2), which degrades regions of heparan sulfate which have low sulfate density, or with 20 mU of chondroitinase abc (lane 1), which removes chondroitin sulfate chains, or with only buffer (lane 3) was performed on the conditioned medium from perlecanD1-Ad infected endothelial cell cultures. Western blot analysis was performed on the samples after incubation at 37° C. for 1 hour (FIG. 4). Using threshold image analysis of the blot it was clear that heparatinase digestion of the sample in conditioned medium (FIG. 4, lane 2) resulted in a significant loss of immunoreactive rD1 relative to the conditioned medium with buffer incubation (lane 3). Chondroitinase abc digestion of the rD1 (FIG. 4, lane 1) resulted in no less immunoreactive rD1. These data taken together suggest that the rD1 is decorated primarily by heparan sulfate and little, if any, chondroitin sulfate. Incomplete heparan sulfate digestion can be attributable to the substrate specificity of the heparatinase I that was used, which supports the data suggesting the rD1 is highly sulfated.

Example 3

Effective Wound Healing by Delivery of a Nucleic Acid Sequence Encoding a Secreted Proteoglycan Polypeptide The effect of expressing a delivered nucleic acid encoding a secreted proteoglycan polypeptide on wound healing was evaluated using the acute calvarial wound model. Two defects were created bilaterally on the calvaria of Balb C mice with a slowly rotating round 3 mm diamond bur and copious saline drip. Brief pressure was applied for hemostasis then approximately 15 µl of a hydroxyapatite (HA) slurry pre-loaded with either the perlecanD1-Ad, or the control RevD1-Ad, was applied to opposite paired defects in each mouse. Approximately $1.6 \times 10^7$ viral particles of perlecanD1-Ad and $5.2 \times 10^6$ viral particles of RevD1-Ad per defect were delivered in the slurry of HA (calculated as approximately equal infectious doses). Crystals were lightly packed into the defect with a spatula and the defect was covered by replacing and securing the skin flap. After 18 or 22 days the animals were sacrificed and the calvarium removed for fixation in HistoChoice (Amresco, Solon, Ohio) for 24 hours, decalcification in 10% w/v EDTA for 6 days, and paraffin embedding. Deparaffinized sections were trichrome stained for collagen and bone.

Figure 5:
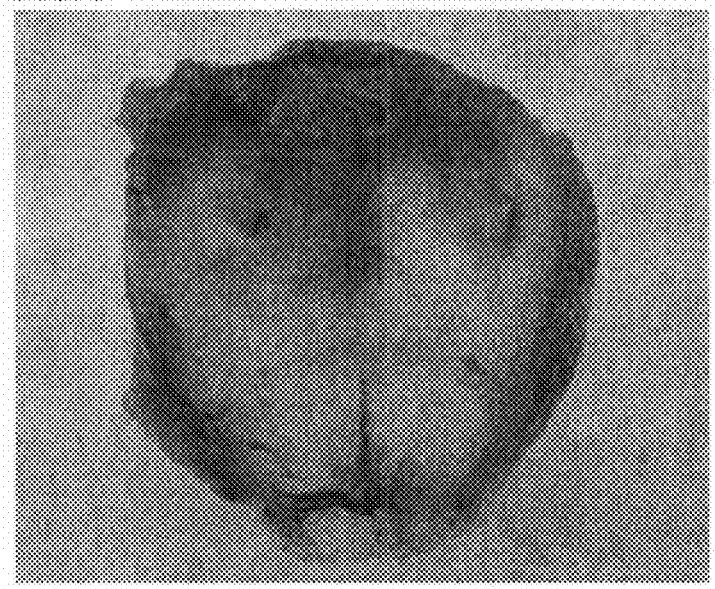
FIG. 5 shows the effect of recombinant perlecan D1 expression on wound healing as evaluated using the acute calvarial wound model. Excised calvarium from mouse 18 days after bilateral osseous defects were created and grafted with a gelatin gel containing HA particles and either perlecanD1-Ad (left side) or control RevD1-Ad (right side). Prior to flap closure, the grafts were covered with a 3 mm diameter barrier membrane (Biomend, a bovine collagen used in guided tissue regeneration).

A group of 8 mice were sacrificed at day 18. By gross observation of the collected calvaria, it was clear to a naïve observer which sites had received the proteoglycan construct, perlecanD1-Ad, and which sites were treated with the control delivery construct (RevD1-Ad); seven of the eight experimental sites were correctly identified, while the eighth was scored as even. FIG. 5 shows one example of the collected calvaria where the top left defect received the perlecanD1-Ad and the top right defect received the control adenovirus (RevD1-Ad). A greater level of vascularity appears in the center of the defect treated with perlecanD1-Ad and the borders surrounding the experimental graft are significantly denser.

Figure 6:
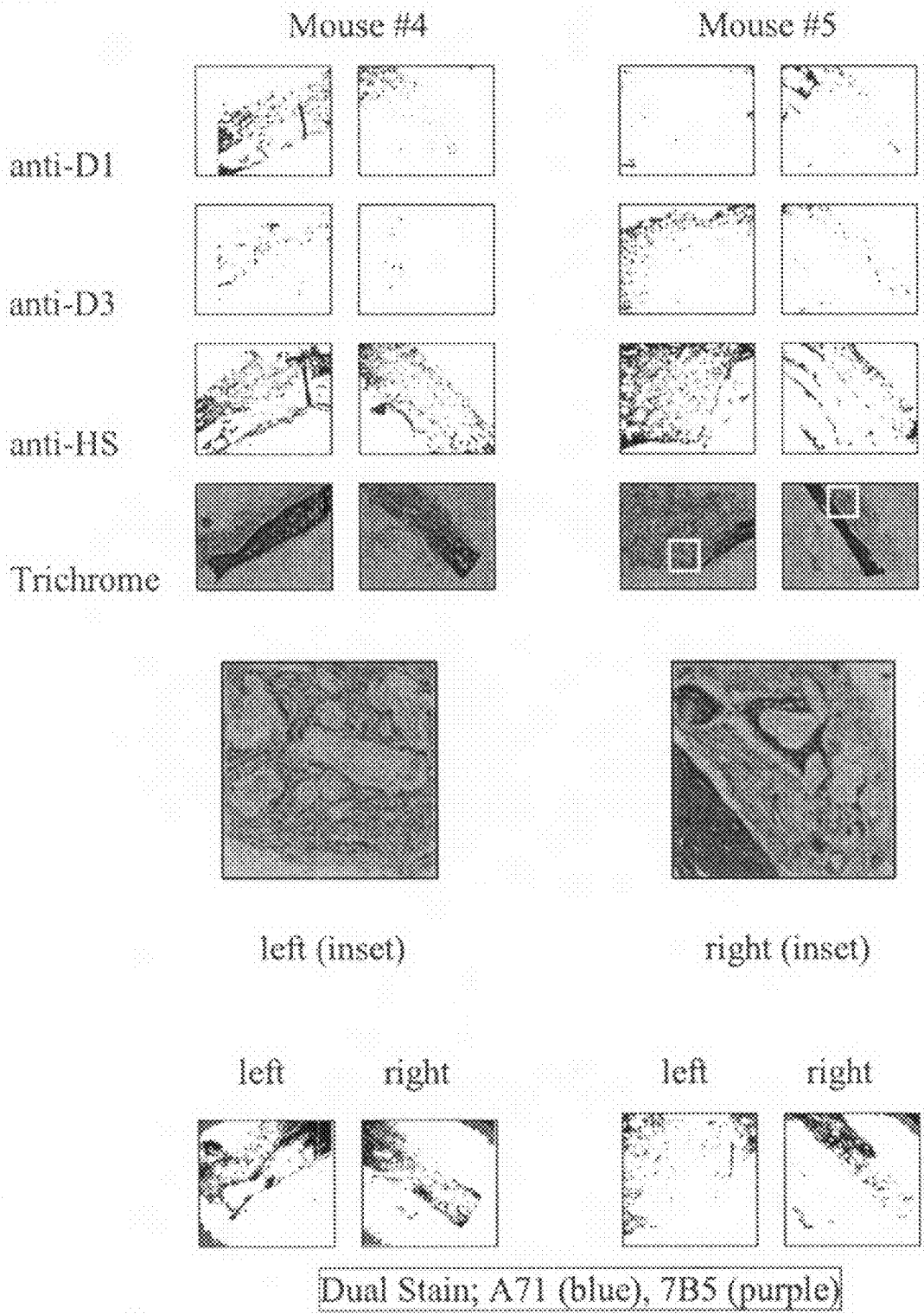
FIG. 6 shows histological analysis of calvarial bone sections by immunochemistry and Masson's trichrome.

Recombinant perlecan D1 expression was associated with accelerated regional new bone growth in the acute calvarial wound model. Adjacent deparaffinized sections of the calvarial bone allowed to heal for 22 days were incubated overnight with 20 µg/ml of either the anti-D1 mAb A71, or the anti-domain 3 (D3) mAb7B5 as a control. After washing and applying an AP-conjugated anti-mouse IgG antibody, BCIP visualization revealed significantly more perlecan D1 in the connective tissue associated with new bone growth (FIG. 6, anti-D1) than in the non-regenerating defect (anti-D1; mean pixel density mouse #4: 54±19 vs. 15±5, respectively; p=0.02). At the same time, the perlecan D3 signal was relatively equal on either side of the calvarium (FIG. 6, anti-D3). Control sections (secondary antibody only) were blank (data not shown). Ratio of anti-D1 to anti-D3 signal for the regenerative vs. the non-regenerative sides of mice #4 and #5 indicated that approximately 7 fold (±5 fold) more rD1 than endogenous D1 was evident in the more fully regenerated graft site vs the lesser regenerated graft site at the 22 day time point.

Heparan sulfate was localized using the monoclonal antibody 2Q546, which recognizes highly charged regions of heparan sulfate. This antibody had the greatest affinity for the heparan sulfate-decorated recombinant in vitro, demonstrated above. In mouse #4, a greater density of heparan sulfate immunoreactivity was evident in association with higher levels of perlecan D1, and new bone (FIG. 6, anti-HBS).

A dual stain with mAb A71 (blue) and mAb 7B5 (purple) was performed, and contrast-enhanced images highlight the greater abundance and intensity of blue signal from regions of bone regeneration than on the non-regenerating osseous defects (FIG. 6). These data suggested that recombinant perlecan D1 was expressed and accumulated in association with more rapid and complete bone regeneration of the calvarial defects. Further, by trichrome staining, the amount of new bone associated with the expressed recombinant perlecan D1 was striking (FIG. 6).

PROPHETIC EXAMPLES

Example 1

Use of Nucleic Acid Encoding a Secreted Proteoglycan Polypeptide in Bone Wounds

The present disclosure contemplates a variety of mechanisms and vectors to deliver a nucleic acid encoding a proteoglycan polypeptide. In one embodiment, a nucleic acid encoding a proteoglycan polypeptide is delivered to a bone wound. In this embodiment, the nucleic acid encoding the proteoglycan polypeptide, such as a cDNA, would be ligated into a replication-incompetent, E1/E3-defective human adenovirus serotype 5-derived vector under the transcriptional control of the human cytomegalovirus early promoter as described previously (Shi, et al., *J Virol* 75(23): 11474-82, 2001). For in situ proteoglycan expression, $10^2$ to $10^9$ adenovirus particles would be delivered per $cm^2$ of wound surface area, or per $cm^3$ of a surgical grafting site.

For delivery, surgical grafting materials or implant materials would be pre-treated with this vector delivery system, preferably in a sterile buffer such as phosphate buffer, pH 7.4. The pre-treatment may be performed during surgery, or at any time prior to the surgery provided the coated surgical implant material is not subject to denaturing temperatures at any time after pre-treatment, and would involve immersion in the pre-treatment solution for a short period of time. The pre-treated grafting material or implant would then be surgically placed. Various growth factors may also be incorporated into the solution for incorporation into, and absorption onto, the grafting materials and surgical implants. Once prepared, the grafting materials and surgical implants would be used according to standard procedures.

The adenoviral vector system delivers the nucleic acid to the site of the wound and the adenoviral vector system infects a plurality of target cells at the site of the wound. The nucleic acid encoding the proteoglycan polypeptide is then transcribed, translated, and the resulting polypeptide is then glycated with at least one glycosaminoglycan chain by the target cell. As the nucleic acid encoding the proteoglycan polypeptide contains a sequence sufficient for excretion, the produced proteoglycan polypeptide is secreted from the target cell and is available for effective treatment of the wound as discussed herein.

Example 2

Use of Nucleic Acid Encoding a Proteoglycan Polypeptide for Treatment of Cutaneous Injury In an alternate embodiment, a nucleic acid of the present disclosure encoding a proteoglycan polypeptide is delivered to a site of cutaneous injury. In this embodiment, the nucleic acid encoding the proteoglycan polypeptide, such as a cDNA, would be ligated into a replication-incompetent, E1/E3-defective human adenovirus serotype 5-derived vector as described above or used in combination with another vector, such as but not limited to, a liposome.

For a 2 cm$^2$ area of cutaneous injury, the adenovirus or liposome vector system would be applied in a small volume (such as <50 µL) and allowed to dry after application. Adenovirus would be delivered in a phosphate buffered saline solution containing 10% glycerol as a thickening agent to aid in application and at an infectious dose of between $10^2$-$10^9$ VP/ml. If the nucleic acid encoding the proteoglycan polypeptide is delivered across the stratum corneum as plasmid DNA, lipid vesicles will be used which have been shown to allow plasmid DNA to cross the stratum corneum, and transfect cells (Alexander, et al., *Hum Mol Genet* 4(12): 2279-85, 1995; Raghavachari, et al, *J Pharm Sci* 91(3): 615-22, 2002). Cationic lipids DOTAP (Avanti Polar Lipids) may be used as a lipid vesicle constituent of the liposomes. The ratio of DNA to liposome can vary from 1:1 to 1:100. The vector systems containing the nucleic acid encoding the proteoglycan polypeptide could be applied multiple times if required.

The vector system delivers the nucleic acid to the site of the cutaneous injury and the vector system infects a plurality of target cells at the site of the cutaneous injury. The nucleic acid encoding the proteoglycan polypeptide is the transcribed, translated and the resulting polypeptide is glycated with at least one glycosaminoglycan chain by the target cell. As the nucleic acid encoding the proteoglycan polypeptide contains a sequence sufficient for excretion, the produced proteoglycan polypeptide is secreted from the target cell and is available for effective treatment of the cutaneous injury as discussed herein.

Example 3

Creating a Nucleic Acid Encoding a Novel Secreted Proteoglycan

As discussed above, the present disclosure provides for a nucleic acid encoding a proteoglycan polypeptide. The nucleic acid encoding a proteoglycan polypeptide is delivered to a target, is transcribed, translated, and the resulting polypeptide is glycated with appropriate glycosaminoglycan chains as dictated by the physiological state of the target cell. The produced proteoglycan polypeptide is then secreted from the target cell. The definition of proteoglycan polypeptide is broad, covering proteoglycan proteins that are naturally occurring or that are synthesized de novo and which may not be naturally occurring, fragments of the foregoing, and modifications to the foregoing that have been altered to include new glycosaminoglycan attachment sites hence creating novel proteoglycans. Such proteoglycan polypeptides may be produced by modifying the nucleic acid encoding a proteoglycan polypeptide as discussed herein. An example is provided below.

Figure 7:
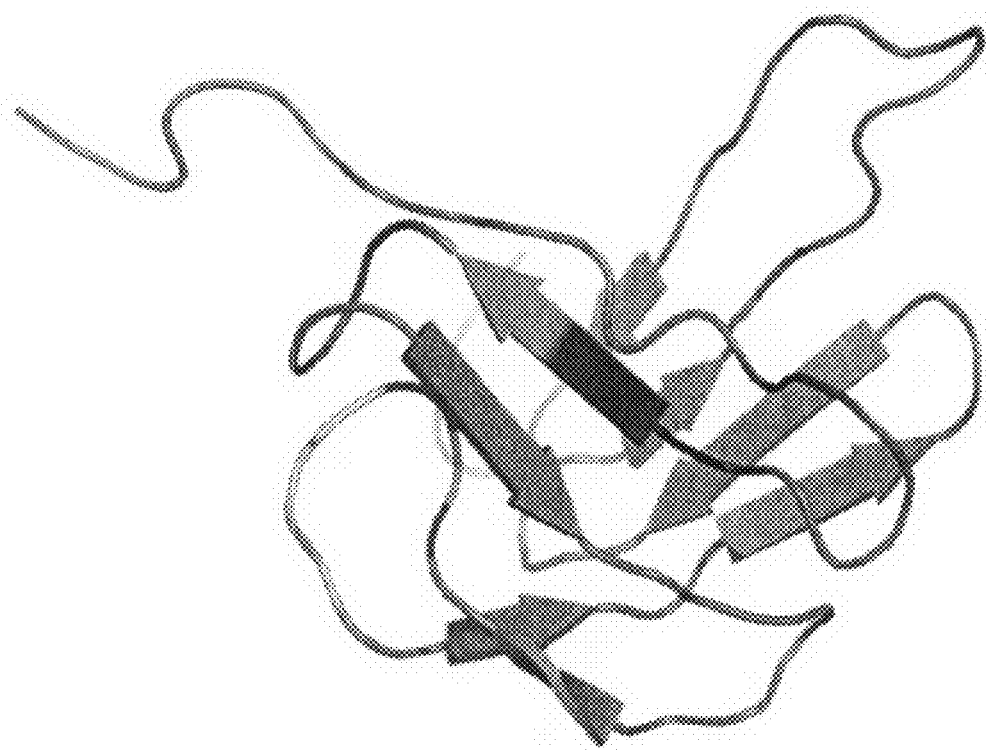
FIG. 7 shows a predicted model of perlecan D1.

An example of how any nucleic acid sequence could be utilized to establish new glycosylation sites is as follows. Using the proteoglycan perlecan as an example again, domain 1 (D1) usually is observed to contain 3 glycosaminoglycan chains, most often heparan sulfate. Currently, no structural data exists for perlecan, or for perlecan D1. Computational modeling of perlecan D1 is somewhat problematic as the 21 kDa protein does not exhibit greater than 25% sequence identity with any known protein structures. The 25% cut-off for most modeling programs does not allow for modeling of the full protein. However, Geno3D allows for modeling of partial sections of the protein when the sequence identity is high enough (Combet, et al., *Bioinformatics* 18(1): 213-4, 2002). Perlecan D1 was modeled with Geno3D against the pdb 1MDC, an insect fatty acid binding protein, which displayed the highest sequence identity of the database at 24%. The predicted model of amino acids 53 to 144 suggested a β-sheet structure and encompassed the three glycosaminoglycan chain attachment sites, which are shown in FIG. 7 by arrow 1 (S65, G66, D67), arrow 2 (S71, G72, D73), and arrow 3 (S76, G77, D78). A β-sheet structure would allow the glycosaminoglycan chains to project away from the protein core tertiary structure and possibly allow growth factors, such as but not limited to, FGF to bind the heparan sulfate chains on one face of the protein while the other face binds the FGF receptor for presentation of FGF. Additional sites for heparan sulfate attachment that are engineered on the same side of the protein as the natural attachment sites are likely to increase growth factor binding either in number or in affinity. Creating mutations that contain amino acids with similar physical properties reduces the possibilities of structural disruption due to the inclusion of the mutations as discussed herein. In addition, including the mutations in proposed loop regions would reduce the probability of structure disruption and allow for glycosaminoglycan chain flexibility for growth factor binding. Therefore, the two chosen mutation sites are L87S, V88G, N89D and S97, P98G, Q99D, also shown in FIG. 7. The two amino acid triads were replaced with an SGD glycosylation sequence. These two sites are close to the three natural sites for glycosylation, and the amino acid changes are conservative enough to allow for proper structure formation. These mutations were made by site-directed mutagenesis in a single round of PCR for each site.

Similar approaches could be used for other proteoglycan protein/polypeptide structures.

The foregoing description illustrates and describes the nucleic acids, compositions, methods and other teachings of the present disclosure. Additionally, the disclosure shows and describes only certain embodiments of the nucleic acids, compositions, methods and other teachings disclosed, but, as mentioned above, it is to be understood that the teachings of the present disclosure are capable of use in various other combinations, modifications, and environments, and is capable of changes or modifications within the scope of the teachings as expressed herein, commensurate with the skill and/or knowledge of a person having ordinary skill in the relevant art. The embodiments described hereinabove are further intended to explain best modes known of practicing the methods and other teachings of the present disclosure and to enable others skilled in the art to utilize the teachings of the present disclosure in such, or other, embodiments and with the various modifications required by the particular applications or uses. Accordingly, the nucleic acids, compositions, methods and other teachings of the present disclosure are not intended to limit the exact embodiments and examples disclosed herein.

The invention claimed is:

1. A method for effective treatment of a wound or a cutaneous injury in a subject in need of such treatment via delivery of a glycosaminoglycan-decorated proteoglycan polypeptide, the method comprising administering via local delivery to a target cell at a site of the wound or cutaneous injury in the subject a composition comprising a vector and a nucleic acid encoding a proteoglycan polypeptide, said nucleic acid comprising a first nucleic acid sequence encoding a sequence sufficient for secretion and a second nucleic acid sequence encoding a polypeptide having one or more sites for the attachment of a glycosaminoglycan chain, whereby a glycosaminoglycan-decorated polypeptide is generated in the target cell by the subject and subsequently secreted from the target cell to deliver an effective amount of glycosaminoglycan to the wound or the cutaneous injury resulting in an improvement in effective treatment of the wounds or the cutaneous injury in the subject, said nucleic acid being delivered in therapeutically effective amount.

2. The method of claim 1 where the proteoglycan polypeptide is a naturally occurring proteoglycan polypeptide.

3. The method of claim 2 where the naturally occurring proteoglycan polypeptide is selected from the group consisting of aggrecan, versican, lumican, syndecan 1-4, glypican 1-5, betaglycan, NG2/CSPG4, CD44/Epican, fibromodulin, PRELP, keratocan, osteoadherin/osteomodulin, epiphycan, osteoglycin/mimecan, neurocan/CSPG3, brevican, bamacan, agrin, perlecan, decorin, biglycan and serglycin.

4. The method of claim 2 where the naturally occurring proteoglycan polypeptide is selected from the group consisting of aggrecan, versican, lumican, syndecan 1-4, glypican 1-5, betaglycan, NG2/CSPG4, CD44/Epican, fibromodulin, PRELP, keratocan, osteoadherin/osteomodulin, epiphycan, osteoglycin/mimecan, neurocan/CSPG3, brevican, bamacan, agrin, and serglycin.

5. The method of claim 2 where the proteoglycan polypeptide is a degenerate variant or an allelic variant of a naturally occurring proteoglycan polypeptide.

6. The method of claim 2 where the proteoglycan polypeptide is a mutant or a variant of a naturally occurring proteoglycan polypeptide.

7. The method of claim 6 where the mutant or variant has been modified to include an additional site for glycosaminoglycan attachment.

8. The method of claim 1 where the proteoglycan polypeptide is not a naturally occurring polypeptide.

9. The method of claim 1 where the sequence sufficient for secretion is a signal sequence.

10. The method of claim 9 where the signal sequence has the sequence of SEQ ID NO. 27.

11. The method of claim 1 where the vector is a viral vector or a non-viral vector.

12. The method of claim 11 where the viral vector is an adenoviral vector, a retroviral vector, a lentiviral vector, a bovine papilloma viral vector, an Epstein-Barr viral vector, an adeno-associated viral vector, a pox viral vector, a baculovirus viral vector, a vaccinia viral vector, a herpes simplex viral vector, or a hybrid of two or more viral vector types.

13. The method of claim 11 where the non-viral vector is a plasmid, a liposome, an electrically charged lipid, a DNA-protein complex or a biopolymer.

14. The method of claim 1 where the composition further comprises a pharmaceutically acceptable carrier.

15. The method of claim 1 where the local delivery is accomplished with a gene gun or a pressure delivery method.

16. The method of claim 1 where said wound is a bone wound.

17. The method of claim 1 where said cutaneous injury is the result of sun exposure or aging.

18. The method of claim 2 where the proteoglycan polypeptide is a fragment of a naturally occurring proteoglycan polypeptide.

* * * * *